(12) United States Patent
Packard et al.

(10) Patent No.: US 10,557,136 B2
(45) Date of Patent: Feb. 11, 2020

(54) IN VIVO DELIVERY OF OLIGONUCLEOTIDES

(71) Applicant: OncoImmunin Inc., Gaithersburg, MD (US)

(72) Inventors: Beverly Packard, Potomac, MD (US); Akira Komoriya, Potomac, MD (US)

(73) Assignee: OncoImmunin Inc., Gaithersburg, MD (US)

( * ) Notice: Subject to any disclaimer, the term of this patent is extended or adjusted under 35 U.S.C. 154(b) by 234 days.

(21) Appl. No.: 14/648,369

(22) PCT Filed: Dec. 12, 2012

(86) PCT No.: PCT/US2012/069294
§ 371 (c)(1),
(2) Date: May 29, 2015

(87) PCT Pub. No.: WO2013/090457
PCT Pub. Date: Jun. 20, 2013

(65) Prior Publication Data
US 2016/0040161 A1 Feb. 11, 2016

Related U.S. Application Data

(60) Provisional application No. 61/630,446, filed on Dec. 12, 2011.

(51) Int. Cl.
*C12N 15/113* (2010.01)

(52) U.S. Cl.
CPC ........ *C12N 15/113* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2003/0224377 A1 | 12/2003 | Wengel et al. | |
| 2005/0142581 A1 | 6/2005 | Griffey et al. | |
| 2009/0203138 A1* | 8/2009 | Kania | A61K 31/7105 435/375 |
| 2009/0325168 A1 | 12/2009 | Packard et al. | |

FOREIGN PATENT DOCUMENTS

| | | |
|---|---|---|
| WO | WO 03/106631 A2 | 12/2003 |
| WO | WO 2009/045536 A2 | 4/2009 |
| WO | WO 2013/090457 A2 | 6/2013 |

OTHER PUBLICATIONS

Collingwood, M.A., et al., "Chemical Modification Patterns Compatible with High Potency Dicer-Substrate Small Interfering RNAs," *Oligonucleotides* 18:187-200, Mary Ann Liebert Inc., United States (2008).
International Search Report for International Application No. PCT/US12/69294, United States Patent and Trademark Office, United States, dated Feb. 22, 2013, 3 pages.
Packard, B.Z. and Komoriya, A., "A Method in Enzymology for Measuring Hydrolytic Activities in Live Cell Environments," in *Methods in Enzymology* 450: 24 pages, Elsevier Inc., United States (2008).
Rudin, C.M., et al., "Phase I Trial of ISIS 5132, an Antisense Oligonucleotide Inhibitor of c-raf-1, Administered by 24-hour Weekly Infusion to Patients with Advanced Cancer," *Clinical Cancer Research* 7:1214-1220, The Association, United States (2001).
Van De Water, F.M., et al., "Intravenously Administered Short Interfering RNA Accumulates in the Kidney and Selectively Suppresses Gene Function in Renal Proximal Tubules," *Drug Metabolism and Disposition* 34;1393-1397, The American Society for Pharmacology and Experimental Therapeutics, United States (2006).
Wang, J., et al., "Delivery of siRNA Therapeutics: Barriers and Carriers," *The AAPS Journal* 12:492-503, American Association of Pharmaceutical Scientists, United States (2010).
Written Opinion for International Application No. PCT/US12/69294, United States Patent and Trademark Office, United States, dated Feb. 22, 2013, 8 pages.
Zimmermann, T.S., et al., "RNAi-mediated gene silencing in non-human primates," *Nature* 441:111-114, Nature Publishing Group, England (2006).
Baker, M.B., "In vitro quantification of specific microRNA using molecular beacons," *Nucleic Acids Research* 40(2):e13, Oxford University Press, England, 12 pages (2011).
Chang, E., et al., "Novel siRNA-based molecular beacons for dual imaging and therapy," *Biotechnology Journal* 2(4):422-425, Wiley-VCH Verlag GmbH & Co. KGaA, Germany (2007).
Extended European Search Report (including listing of searched claims) for EP Application No. 12858522.1, Munich, Germany, dated Aug. 20, 2015, 13 pages.
Harborth, J., et al., "Sequence, chemical, and structural variation of small interfering RNAs and short hairpin RNAs and the effect on mammalian gene silencing," *Antisense & Nucleic Acid Drug Development* 13:83-105, Mary Ann Liebert, Inc., United States (2003).
Juliano, R., et al., "Survey and Summary Mechanisms and strategies for effective delivery of antisense and siRNA oligonucleotides," *Nucleic Acids Research* 36(12):4158-4171, Oxford University Press, England (2008).

(Continued)

*Primary Examiner* — J. E. Angell
(74) *Attorney, Agent, or Firm* — Nixon & Vanderhye P.C.

(57) ABSTRACT

This invention provides a method for the in vivo delivery of oligonucleotides. The invention utilizes the presence of one or plurality of HES linked to an oligonucleotide to deliver a nucleic acid sequence of interest into the cytoplasm of cells and tissues of live organisms. The delivery vehicle is non-toxic to cells and organisms. Since delivery is sequence-independent and crosses membranes in a receptor-independent manner, the delivered oligonucleotide can target complementary sequences in the cytoplasm as well as in the nucleus of live cells. Sequences of bacterial or viral origin can also be targeted. The method can be used for delivery of genes coding for expression of specific proteins, antisense oligonucleotides, siRNAs, shRNAs, Dicer substrates, miRNAs, anti-miRNAs or any nucleic acid sequence in a living organism. The latter include mammals, plants, and microorganisms such as bacteria, protozoa, and viruses.

21 Claims, 5 Drawing Sheets
Specification includes a Sequence Listing.

(56) References Cited

OTHER PUBLICATIONS

Lerga, T.M., et al., "Rapid determination of total hardness in water using fluorescent molecular aptamer beacon," *Analytica Chimica Acta* 610:105-111, Elsevier, B.V., Netherlands (2008).
Shim, M.S. and Kwon, Y.J., "Efficient and targeted delivery of siRNA in vivo," *FEBS Journal* 277(23):4814-4827, Blackwell Publishing, England (2010).
Vijayanathan, V., et al., "Direct measurement of the association constant of HER2/neu antisense oligonucleotide to its target RNA sequence using a molecular beacon," *Antisense & Nucleic Acid Drug Development* 12:225-233, Mary Ann Liebert, Inc., United States (2002).
Watts, J.K. and Corey, D.R., "Silencing disease genes in the laboratory and the clinic," *Journal of Pathology* 226(2):365-379, John Wiley & Sons, Ltd., England (2012).
European Search Opinion for EP Application No. 12858522.1, Munich, Germany, dated Aug. 20, 2015, 5 pages.
Wang, J., et al., "Delivery of siRNA therapeutic: barriers and carriers," *AAPS J.* 12(4):492-503 (2010).
Laufer, S., et al., "Selected Strategies for the Delivery of siRNA In Vitro and In Vivo," RNA Technologies, Springer-Verlag Berlin Heidelberg; pp. 29-57 (2010).

\* cited by examiner

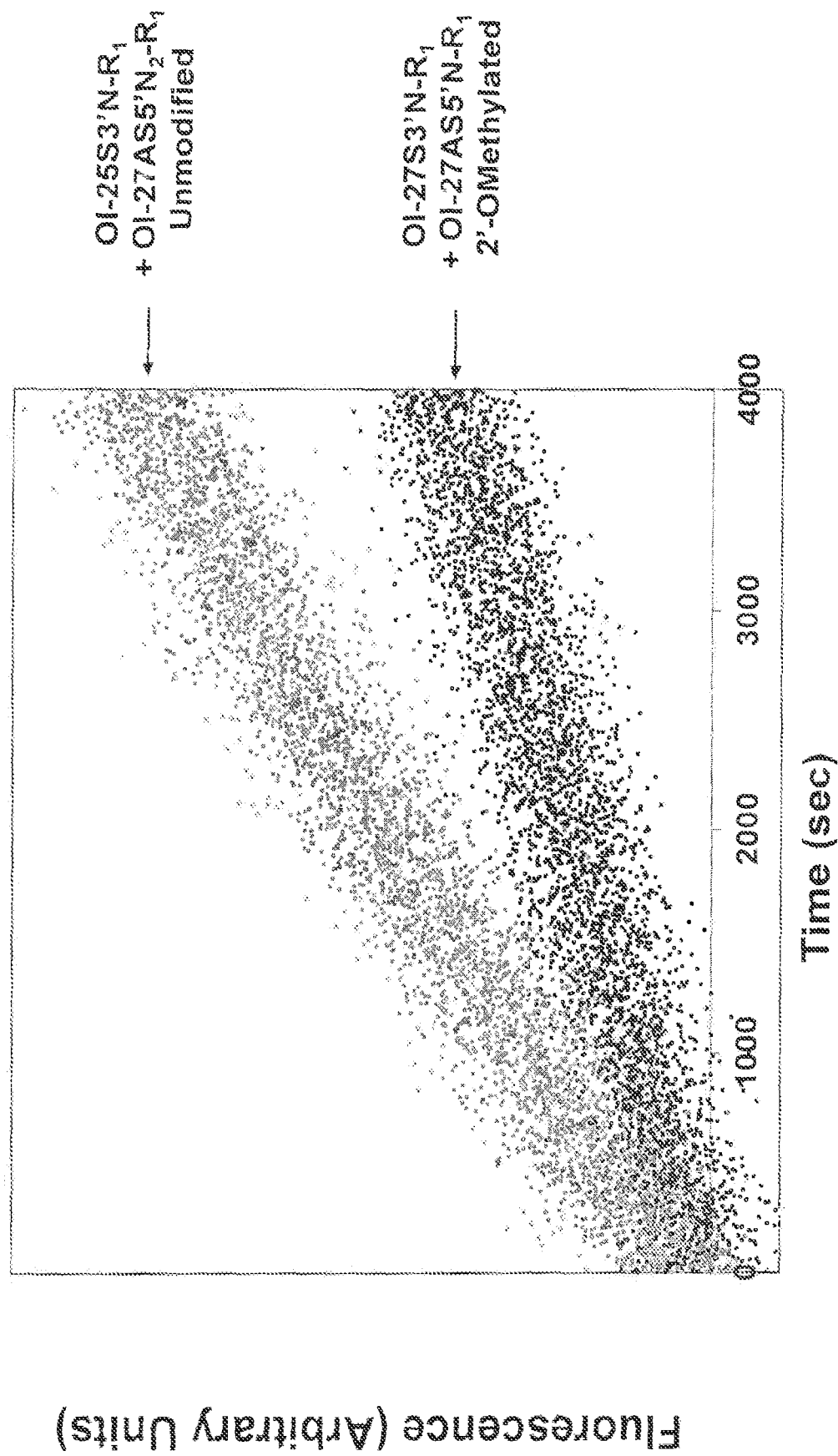

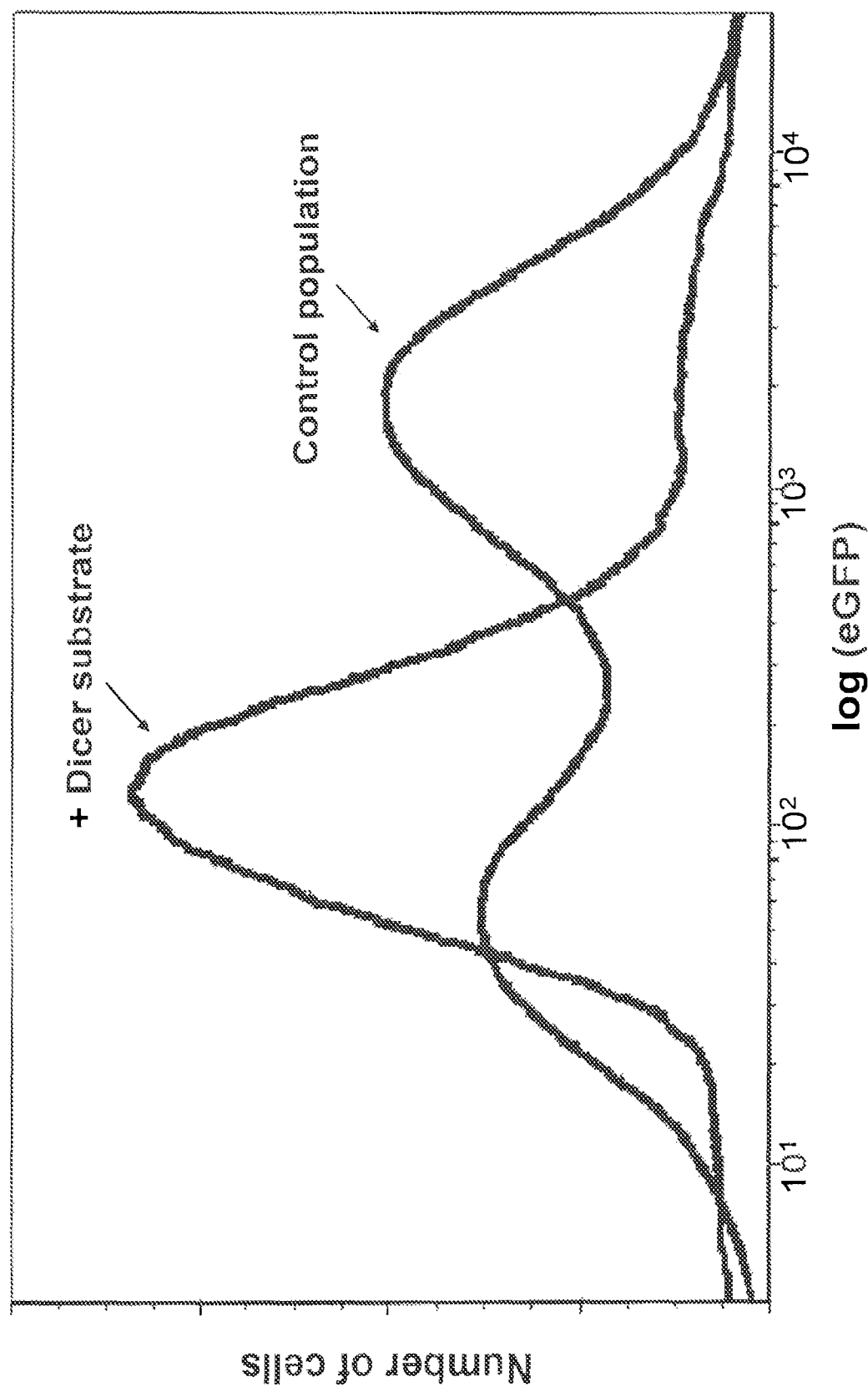

IN VIVO DELIVERY OF OLIGONUCLEOTIDES

BACKGROUND OF THE INVENTION

Field of the Invention

This invention pertains to the field of oligonucleotide therapeutics. In particular, this invention provides improved in vivo delivery for oligonucleotides including modified oligonucleotides and oligonucleotide mimics.

Over the past several decades the use of oligonucleotides as therapeutic agents has been the focus of much interest. Both blockage of the transcription of specific genes and addition of oligonucleotide sequences coding for particular proteins have been attempted as therapies for a plethora of pathologic conditions including cancer, infectious diseases, and neurodegenerative conditions. Moreover, multiple chemical approaches have been developed to address the synthetic, immunogenic, and biophysical properties of potential oligonucleotide-based drugs and drug formulations. However, despite some success in solution and ex vivo systems, delivery of oligonucleotides across biologic barriers such as cell membranes and extracellular matrices present in live organisms as well as structural components of infectious agents such as cell walls has been suboptimal. Thus, accessibility to molecular targets inside cells and tissues in vivo has been limiting development of the oligonucleotide therapeutics field.

In recent efforts to overcome some of the limitations of the delivery of DNA and RNA sequences, delivery vehicles composed of lipids, sugars, and proteins conjugated to or encapsulating oligonucleotide sequences of interest, e.g., liposomes and lipid nanoparticles, cholesterol conjugates, and antibody conjugates, have been developed. However, none of these formulations has enabled delivery of oligonucleotide cargoes for the field of oligonucleotide therapeutics to reach its anticipated role in disease treatment. Accordingly, there is a need for improved in vivo delivery systems of oligonucleotide-based therapeutics.

BRIEF SUMMARY OF THE INVENTION

The invention relates to oligonucleotide complexes containing H-type excitonic structures (HES) and methods of making and using these complexes. The invention is based in part on the important discovery of the inventors that the linkage of one or a plurality of HES to single, double and multiple strand oligonucleotide sequences results in an increased delivery of the HES-oligonucleotide sequences across physiologic boundaries found in in vivo systems.

One of the toughest obstacles limiting the use of RNAi and antisense oligonucleotides, (PNAs) and PMOs in gene expression altering therapy has been the low uptake of these compounds by eukaryotic cells, which with currently available delivery methodologies is compounded by the sequestration and/or degradation of the compounds that actually do enter the cell; the latter is predominantly via endocytosis. As will be immediately apparent to a person of skill in the art, the surprisingly high efficiency with which the non-toxic HES-oligonucleotide complexes of the invention are delivered into cells through sequence independent passive diffusion and the discovery by the inventors that these oligonucleotides do not co-localize with lysozomes within cells, indicate that the HES-oligonucleotide delivery vehicles of the invention have the ability to enter all intracellular spaces/compartments. Thus, there are essentially limitless applications in for example, research, diagnostics and therapeutics arenas. In particular embodiments, the invention pertains to the in vivo delivery of HES-oligonucleotide complexes containing HES and at least one therapeutic oligonucleotide for the treatment or prevention of a disease, disorder or condition.

Moreover, with the currently available delivery methodologies the induction of innate antiviral defenses in mammalian cells to exogenous nucleic acid sequences have likewise significantly limited the development and use of therapeutic oligonucleotides. The inventors have discovered that HES-oligonucleotides have low toxicity (at concentrations greater than 10 fold the determined oligonucleotide in vivo cell loading level) and in fact, have surprisingly found that the chemical linkage of HES oligonucleotides does not induce the interferon response in a host subject (i.e., mouse) compared to that observed with other delivery vehicles. Accordingly, in additional embodiments, the invention encompasses a method of limiting the interferon response to an administered exogenous nucleic acid (e.g., oligonucleotide) in a host, comprising linking 1, 2, 3 or more oligonucleotides with an HES to form an HES-oligonucleotide complex and administering the HES-oligonucleotide complex to a subject.

In some embodiments, an HES-oligonucleotide complex delivery vehicle is used as a diagnostic to identify and/or quantitate the presence of a nucleic acid of interest in vivo. In other embodiments, an HES-oligonucleotide complex delivery vehicle is used to identify the presence of an infectious agent in a host organism such as, a virus or bacterium in a mammalian tissue. In these embodiments the altered fluorescence that results upon the disruption of the HES of the complex can serve as an in vivo marker for binding of one or more HES-oligonucleotide sequences in the complex to a nucleic acid target sequence in a cell. Thus, in some embodiments, the complexes of the invention have both diagnostic and therapeutic-applications. This approach can also be used to quantitate the number of copies of an aberrant gene in a host in vivo.

In further embodiments, the invention provides a method for detecting an altered level of a nucleic acid biomarker for a disease or disorder in vivo comprising, administering to a subject an HES-oligonucleotide containing an oligonucleotide that specifically hybridizes with the nucleic acid biomarker, determining the level of fluorescence in the subject, and comparing the level of fluorescence with that obtained for a control subject that has been administered the HES-oligonucleotide, wherein an altered fluorescence compared to the control indicates that the subject has an altered level of the nucleic acid biomarker. This approach can also be used to quantitate the number of copies of an aberrant gene of host origin in vivo In some embodiments, the disease or disorder is: cancer, fibrosis, a proliferative disease or disorder, a neurological disease or disorder, and inflammatory disease or disorder, a disease or disorder of the immune system, a disease or disorder of the cardiovascular system, a metabolic disease or disorder, a disease or disorder of the skeletal system, or a disease or disorder of the skin or eyes.

In additional embodiments, the methods of the invention are used to identify and/or distinguish between different diseases or disorders. The methods of the invention can likewise be used to determine among other things, altered nucleic acid (e.g., DNA and RNA) profiles that distinguish between normal and diseased (e.g., cancerous) tissue or cells, discriminate between different subtypes of diseased cells (e.g., between different cancers and subtypes of a particular cancer), to discriminate between mutations (e.g., oncogenic mutations) giving rise to or associated with different disease states, and to identify tissues of origin (e.g., in a metastasized tumor).

The invention provides compositions and methods for modulating nucleic acids and protein encoded or regulated by these modulated nucleic acids. In particular embodiments, the invention provides compositions and methods for modulating the levels, expression, processing or function of a mRNA, small non-coding RNA (e.g., miRNA), a gene or a protein. In particular embodiments, the invention provides a method of delivering an oligonucleotide to a cell in vivo by administering to a subject an HES-oligonucleotide complex containing the oligonucleotide. In particular embodiments, the oligonucleotide is a therapeutic oligonucleotide. Moreover, in some embodiments, the oligonucleotides in the HES-oligonucleotides of the invention are therapeutic oligonucleotides, and the destruction or significant loss of HES that results in an increased fluorescence when the therapeutic HES oligonucleotides specifically hybridizes with target nucleic acids indicates that the therapeutic oligonucleotides have been delivered to, and have hybridized with the target nucleic acid. Thus, in some embodiments, the invention provides a method for monitoring and/or quantitating the delivery of a therapeutic oligonucleotide to a target nucleic acid in vivo, comprising administering to a subject, a HES oligonucleotides containing a therapeutic oligonucleotide that specifically hybridizes to the target nucleic acid, and determining the level of fluorescence in a cell or tissue of the subject, wherein an increased fluorescence in the cell or tissue compared to a control cell or tissue indicates that that the therapeutic oligonucleotide has been delivered to and hybridized with the target nucleic acid.

In additional embodiments, the invention is directed to compositions for delivering therapeutic oligonucleotides to a subject, wherein the compositions comprise one or more H-type excitonic structures (HES) operably associated with a therapeutically effective amount of a therapeutic oligonucleotide that specifically hybridizes to a nucleic acid sequence in vivo and modulates the level of a protein encoded or regulated by the nucleic acid. In some embodiments, the therapeutic oligonucleotide is from about 8 nucleotides to about 750 nucleotides in length. In some embodiments, the therapeutic oligonucleotide is from about 10 nucleotides to about 100 nucleotides in length. In some embodiments, the therapeutic oligonucleotide is single stranded. In other embodiments, the therapeutic oligonucleotide is double stranded. In additional embodiments, the HES-oligonucleotide comprises 3 or more fluorophores capable of forming one or more HES. In further embodiments, the therapeutic oligonucleotide is a member selected from: siRNA, shRNA, miRNA, a Dicer substrate, an aptamer, a decoy and antisense. In further embodiments, the antisense oligonucleotide is DNA or a DNA mimic.

In some embodiments, the therapeutic oligonucleotide in an HES-oligonucleotide of the invention is an antisense oligonucleotide that specifically hybridizes to an RNA. In farther embodiments, the antisense oligonucleotide is a substrate for RNAse H when hybridized to the RNA. In particular embodiments, the antisense oligonucleotide is a gapmer. In some embodiments, the antisense oligonucleotide contains one or more modified internucleoside linkages selected from: phosphorothioate, phosphorodithioate, phosphoramide, 3'-methylene phosphonate, O-methylphosphoroamidiate, PNA and morpholino. In additional embodiments, the antisense oligonucleotide contains one or more modified nucleobases selected from C-5 propyne and 5-methyl C. In some embodiments, at least one nucleotide of the antisense oligonucleotide contains a modified sugar moiety comprising a modification at the 2'-position, a PNA motif, or a morpholino motif. In further embodiments, at least one nucleotide of the antisense oligonucleotide contains a modified nucleoside motif selected from: 2'OME, LNA, alpha LNA, 2'-Fluoro (2'F), 2'-O(CH$_2$)$_2$OCH$_3$(2'-MOE) and 2'-OCH$_3$(2'-O-methyl). In some embodiments, the modified nucleoside motif is an LNA or alpha LNA in which a methylene (—CH2-)$_n$ group bridges the 2' oxygen atom and the 4' carbon atom wherein n is 1 or 2. In further embodiments, the LNA or alpha LNA contains a methyl group at the 5' position.

In additional embodiments, the therapeutic oligonucleotide in an HES-oligonucleotide of the invention is an antisense oligonucleotide that specifically hybridizes to an RNA, but the antisense oligonucleotide is not a substrate for RNAse H when hybridized to the RNA. In some embodiments, the antisense oligonucleotide is DNA or a DNA mimic. In some embodiments, the antisense oligonucleotide contains one or more modified internucleoside linkages selected from: phosphorothioate, phosphorodithioate, phosphoramide, 3'-methylene phosphonate, O-methylphosphoroamidiate, PNA and morpholino. In additional embodiments, the antisense oligonucleotide contains one or more modified nucleobases selected from C-5 propyne and 5-methyl C. In some embodiments, at least one nucleotide of the antisense oligonucleotide comprises a modified sugar moiety containing a modification at the 2'-position, a PNA motif, or a morpholino motif. In further embodiments, each nucleoside of the oligonucleotide comprises a modified sugar moiety containing a modification at the 2'-position, a PNA motif, or a morpholino motif. In additional embodiments, the HES-oligonucleotide comprises a modified sugar moiety containing one or more modified nucleoside motifs selected from: 2'OME, LNA, alpha LNA, 2'-Fluoro (2'F), 2'-O(CH$_2$)$_2$OCH$_3$(2'-MOE) and 2'-OCH$_3$(2'-O-methyl). In some embodiments, the modified nucleoside motif is an LNA or alpha LNA in which a methylene (—CH2-)$_n$ group bridges the 2' oxygen atom and the 4' carbon atom wherein n is 1 or 2. In further embodiments, the LNA or alpha LNA contains a methyl group at the 5' position. In further embodiments, each nucleoside of the oligonucleotide comprises a modified nucleoside motifs selected from: 2'OME, LNA, alpha LNA, 2'-Fluoro (2'F), 2'-O(CH$_2$)$_2$OCH$_3$(2'-MOE) and 2'-OCH$_3$(2'-O-methyl).

In further embodiments, the therapeutic oligonucleotide in an HES-oligonucleotide of the invention is an antisense oligonucleotide containing a sequence that specifically hybridizes to: (a) a sequence within 30 nucleotides of the AUG start codon of an mRNA; (b) nucleotides 1-10 of a miRNA; (c) a sequence in the 5' untranslated region of an mRNA; (d) a sequence in the 3' untranslated region of an mRNA; (e) an intron/exon junction of an mRNA; (f) a sequence in a precursor-miRNA (pre-miRNA) or primary-miRNA (pre-miRNA) that when bound by the oligonucleotide blocks miRNA processing; and (g) an intron/exon junction and a region 1 to 50 nucleobases 5' of an intron/exon junction of an RNA.

In another embodiment, the invention is directed to a composition for delivering a therapeutic oligonucleotide to a subject, wherein the composition comprises one or more H-type excitonic structures (HES) operably associated with a therapeutically effective amount of a therapeutic oligonucleotide that specifically hybridizes with a nucleic acid sequence in vivo and modulates the level of a protein encoded or regulated by the nucleic acid through the induction of RNA interference (RNAi). In some embodiments, the therapeutic oligonucleotide is siRNA, shRNA or a Dicer substrate. In further embodiments, the therapeutic oligonucleotide is 18-35 nucleotides in length. In some embodiments, the therapeutic oligonucleotide is a dicer substrate and contains 2 nucleic complementary nucleic acid strands that are each 18-25 nucleotides in length and contain a 2 nucleotide 3' overhang. In some embodiments, the oligonucleotide is dsRNA or a dsRNA mimic that is processed by Dicer enzymatic activity. In additional embodiments, the therapeutic oligonucleotide is single stranded RNA or RNA mimic capable of inducing RNA interference. In some embodiments, the therapeutic oligonucleotide contains one or more modified internucleoside linkages selected from: phosphorothioate, phosphorodithioate, phosphoramide, 3'-methylene phosphonate, O-methylphosphoroamidiate, PNA and morpholino. In additional embodiments, the therapeutic oligonucleotide contains one or more modified nucleobases selected from C-5 propyne and 5-methyl C. In some embodiments, at least one nucleotide of the antisense oligonucleotide contains a modified sugar moiety comprising a modification at the 2'-position, a PNA motif, or a morpholino motif. In further embodiments, at least one nucleotide of the therapeutic oligonucleotide comprising a modified sugar motif selected from: 2'OME, LNA, alpha LNA, 2'-Fluoro (2'F), 2'-O(CH$_2$)$_2$OCH$_3$(2'-MOE) and 2'-OCH$_3$(2'-O-methyl). In some embodiments, the modified nucleoside motif is an LNA or alpha LNA in which a methylene (—CH2-)$_n$ group bridges the 2' oxygen atom and the 4' carbon atom wherein n is 1 or 2. In further embodiments, the LNA or alpha LNA contains a methyl group at the 5' position.

The HES-oligonucleotide complexes of the invention provide a highly efficient in vivo delivery of oligonucleotides into cells, essentially have limitless applications in modulating target nucleic acid and protein levels and activity The HES-oligonucleotide complexes are particularly useful in therapeutic applications.

In some embodiments, the invention the invention provides a method of modulating a target nucleic acid a subject comprising administering an HES-oligonucleotide complex to the subject, wherein an oligonucleotide of the complex comprises a sequence substantially complementary to the target nucleic acid that specifically hybridizes to and modulates levels of the nucleic acid or interferes with its processing or function. In some embodiments, the target nucleic acid is RNA, in further embodiments the RNA is mRNA or miRNA. In further embodiments, the oligonucleotide reduces the level of a target RNA by at least 10%, at least 20%, at least 30%, at least 40% or at least 50% in one or more cells or tissues of the subject. In some embodiments, the target nucleic acid is a DNA.

The invention also provides compositions and methods for modulating nucleic acids and protein encoded or regulated by these modulated nucleic acids. In particular embodiments, the invention provides compositions and methods for modulating the levels, expression, processing or function of a mRNA, small non-coding RNA (e.g., miRNA), a gene or a protein.

In one embodiment, the invention provides a method of inhibiting the activity and/or reducing the expression of a target nucleic acid in a subject, comprising administering to the subject an HES-oligonucleotide complex comprising an oligonucleotide which is targeted to nucleic acids comprising or encoding the nucleic acid and which acts to reduce the levels of the nucleic acid and/or interfere with its function in the cell. In particular embodiments, the target nucleic acid is a small-non coding RNA, such as, a miRNA. In some embodiments, the oligonucleotide comprises a sequence substantially complementary to the target nucleic acid.

In additional embodiments, the invention provides a method of reducing the expression of a target RNA in a subject in need of reducing expression of said target RNA, comprising administering to said subject an antisense HES-oligonucleotide complex. In particular embodiments, an oligonucleotide in the complex is a substrate for RNAse H when bound to said target mRNA. In further embodiments, the oligonucleotide is a gapmer.

In an additional embodiment, the invention provides a method of increasing the expression or activity of a nucleic acid in a subject, comprising administering to the subject an HES-oligonucleotide complex containing an oligonucleotide which comprises or encodes the nucleic acid or increases the endogenous expression, processing or function of the nucleic acid (e.g., by binding regulatory sequences in the gene encoding the nucleic acid) and which acts to increase the level of the nucleic acid and/or increase its function in the cell. In some embodiments, the oligonucleotide comprises a sequence substantially the same as nucleic acids comprising or encoding the nucleic acid.

The invention also encompasses a method of treating a disease or disorder characterized by the overexpression of a nucleic acid in a subject, comprising administering to the subject an HES-oligonucleotide complex containing an oligonucleotide which is targeted to a nucleic acid comprising or encoding the nucleic acid and which acts to reduce the levels of the nucleic acid and/or interfere with its function in the subject. In further embodiments, the invention encompasses a method of treating a disease or disorder characterized by the overexpression of a protein in a subject, comprising administering to the subject an HES-oligonucleotide complex containing an oligonucleotide which is targeted to a nucleic acid encoding the protein or decreases the endogenous expression, processing or function of the protein in the subject. In some embodiments, the nucleic acid is DNA, mRNA or miRNA. In additional embodiments the oligonucleotide is selected from a siRNA, shRNA, miRNA, an anti-miRNA, a dicer substrate, an antisense oligonucleotide, a plasmid capable of expressing a siRNA, a miRNA, a ribozyme and an antisense oligonucleotide.

In an additional embodiment, the invention also encompasses a method of treating (e.g., alleviating) a disease or disorder characterized by the aberrant expression of a protein in a subject, comprising administering to the subject an HES-oligonucleotide complex, containing an oligonucleotide which specifically hybridizes to the mRNA encoding the protein and alter the splicing of the target RNA (e.g., promoting exon skipping in instances where production or overproduction of a particular splice product is implicated in disease). In some embodiments, each nucleoside of the oligonucleotide comprises at least one modified sugar moiety comprising a modification at the 2'-position. In particular embodiments, the modified oligonucleotide is a 2' OME or 2' allyl. In additional embodiments, the modified oligonucleotide is LNA, alpha LNA (e.g., an LNA or alpha LNA containing a steric bulk moiety at the 5' position (e.g., a methyl group). In some embodiments the oligonucleotide is a LNA or phosphorodiamidate morpholino (PMO). In some embodiments, the oligonucleotide sequence specifically hybridizes to a sequence within 30 nucleotides of the AUG start codon, a sequence in the 5' or 3' untranslated region of a target RNA, or a sequence that alters the splicing of a target mRNA. In particular the oligonucleotide specifically hybridizes to a sequence that alters the splicing of target mRNA in Duchenne Muscular Dystrophy (DMD). In further embodiments, the altered splicing results in the "skipping" of exon 51 in the resulting mRNA.

In various embodiments, the invention provides compositions for use in modulating a target nucleic acid or protein in a cell, in vivo in a subject, or ex vivo. The HES-oligonucleotide compostions of the invention have applications in for example, treating a disease or disorder characterized by an overexpression, underexpression and/or aberrant expression of a nucleic acid or protein in a subject in vivo or ex vivo. Uses of the compositions of the invention in treating exemplary diseases or disorders selected from: an infectious disease, cancer, a proliferative disease or disorder, a neurological disease or disorder, and inflammatory disease or disorder, a disease or disorder of the immune system, a disease or disorder of the cardiovascular system, a metabolic disease or disorder, a disease or disorder of the skeletal system, and a disease or disorder of the skin or eyes are also encompassed by the invention.

In additional embodiments, the invention provides a method for cell nuclear reprograming. In some embodiments, an HES-oligonucleotides containing one or more mimics and/or inhibitor of a miRNA or a plurality of miRNAs are administered ex vivo into cells such as, human and mouse somatic cells to reprogram the cells to have one or more properties of induced pluripotent stem cells (iPSCs) or embryonic stem (ES)-like pluripotent cells. The non-toxic and highly efficient HES-oligonucleotide delivery system of the invention provides a greatly increased efficiency of delivery method for reprogramming cells compared to conventional oligonucleotide delivery methods (see, e.g., U.S. Publ. Nos. 2010/0075421, US 2009/0246875, US 2009/0203141, and US 2008/0293143).

Definitions

The following abbreviations are used herein:
The terms "nucleic acid" or "oligonucleotide" refer to at least two nucleotides covalently linked together. A nucleic acid/oligonucleotide of the invention is preferably single-stranded or double-stranded and generally contains phosphodiester bonds, although in some cases, as outlined below, nucleic acid/oligonucleotide analogs are included that have alternate backbones, comprising, for example, phosphoramide (see, e.g., Beaucage et al. (1993) Tetrahedron 49(10): 1925) and references therein; Letsinger (1970) J. Org. Chem. 35:3800; Sprinzl et al. (1977) Eur. J. Biochem. 81:579; Letsinger et al. (1986) Nucl. Acids Res. 14:3587; Sawai et al. (1984) Chem. Lett. 805; Letsinger et al. (1988) J. Am. Chem. Soc. 110:4470; and Pauwels et al. (1986) Chemica Scripta 26:1419, the entire contents of each of which is herein incorporated by reference in its entirety), phosphorathioate (Mag et al. (1991) Nucleic Acids Res. 19:1437; and U.S. Pat. No. 5,644,048, the entire contents of each of which is herein incorporated by reference in its entirety), phosphorodithioate (Briu et al (1989) J. Am. Chem. Soc. 111:2321), O-methylphosphoroamidiate linkages (see, e.g., Eckstein, Oligonucleoetides and Analogues: A Practical Approach, Oxford University Press), and peptide nucleic acid backbones and linkages (see, e.g., Egholm (1992) J. Am. Chem. Soc. 114:1895; Meier et al. (1992) Chem. Int. Ed. Engl. 31:1008; Nielsen (1993) Nature 365: 566; Carlsson et al. (1996) Nature 380:207, the entire contents of each of which is herein incorporated by reference in its entirety). Other analog nucleic acids/oligonucleotides include those with positive backbones (see, e.g., Dempcy et al. (1995) Proc. Natl. Acad. Sci USA 92:6097, the entire contents of each of which is herein incorporated by reference in its entirety); non-ionic backbones (see, e.g., U.S. Pat. Nos. 5,386,023, 5,637,684, 5,602,240, 5,216,141, and 4,469,863; Angew. (1991) Chem. Intl, Ed. English 30:423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4:395; Jeffs et al. (1994) J. Biomolecular NMR 34:17; Tetrahedron Lett. 37:743 (1996), the entire contents of each of which is herein incorporated by reference in its entirety), and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids/oligonucleotides containing one or more carbocyclic sugars are also included within the definition of nucleic acids/oligonucleotides (see, e.g., Jenkins et al. (1995), Chem. Soc. Rev. pp 169-176, the entire contents of each of which is herein incorporated by reference in its entirety). Several nucleic acid/oligonucleotide analogs are described in Rawls, C & E News Jun. 2 1997 page 35, which is herein incorporated by reference in its entirety). These modifications of the ribose-phosphate backbone may be done for example, to facilitate the addition of additional moieties such as labels, or to increase the stability and half-life of such molecules in physiological environments. Nucleic acid/oligonucleotide backbones of oligonucleotides used in the invention range from about 5 nucleotides to about 750 nucleotides. Preferred nucleic acid/oligonucleotide backbones used in this invention range from about 5 nucleotides to about 500 nucleotides, and preferably from about 10 nucleotides to about 100 nucleotides in length. As used herein, the term "about" or "approximately" when used in conjunction with a number refers to any number within 0.25%, 0.5%, 1%, 5% or 10% of the referenced number.

The oligonucleotides in the HES-oligonucleotide complexes of the invention are polymeric structures of nucleoside and/or nucleotide monomers capable of specifically hybridizing to at least a region of a nucleic acid target. As indicated above, HES-oligonucleotides include, but are not limited to, compounds comprising naturally occurring bases, sugars and intersugar (backbone) linkages, non-naturally occurring modified monomers, or portions thereof (e.g., oligonucleotide analogs or mimetics) which function similarly to their naturally occurring counterpart, and combinations of these naturally occurring and non-naturally occurring monomers. As used herein, the term "modified" or "modification" includes any substitution and/or any change from a starting or natural oligomeric compound, such as an oligonucleotide. Modifications to oligonucleotides encompass substitutions or changes to internucleoside linkages, sugar moieties, or base moieties, such as those described herein and those otherwise known in the art.

The term "antisense" as used herein, refers to an oligonucleotide sequence, written in the 5' to 3' direction, comprises the reverse complement of the corresponding region of a target nucleic acid and/or that is able to specifically hybridize to the target nucleic acid under physiological conditions. Thus, in some embodiments, the term antisense refers to an oligonucleotide that comprises the reverse complement of the corresponding region of a small noncoding RNA, untranslated mRNA and/or genomic DNA sequence. In particular embodiments, an antisense HES-oligonucleotide in a complex of the invention, once hybridized to a nucleic acid target, is able to induce or trigger a reduction in target gene expression, target gene levels, or levels of the protein encoded by the target nucleic acid.

"Complementary," as used herein, refers to the capacity for pairing between a monomeric component of an oligonucleotide and a nucleotide in a targeted nucleic acid (e.g., DNA, mRNA, and a non-coding RNA such as, a miRNA). For example, if a nucleotide at a certain position of an oligonucleotide is capable of hydrogen bonding with a nucleotide at the same position of a DNA/RNA molecule, then the oligonucleotide and DNA/RNA are considered to be complementary at that position.

In the context of this application, "hybridization" means the pairing of an oligonucleotide with a complementary nucleic acid sequence. Such pairing typically involves hydrogen bonding, which may be Watson-Crick, Hoogsteen or reversed Hoogsteen hydrogen bonding, between complementary nucleoside or nucleotide bases (nucleobases) of an oligonucleotide and a target nucleic acid sequence (e.g., wherein the oligonucleotide comprises the reverse complementary nucleotide sequence of the corresponding region of the target nucleic acid). In particular embodiments, an oligonucleotide specifically hybridizes to a target nucleic acid. The terms "specifically hybridizes" and specifically hybridizable" are used interchangeably herein to indicate a sufficient degree of complementarity such that stable and specific binding occurs between the oligonucleotide and the target nucleic acid (i.e., DNA or RNA). It is understood that an oligonucleotide need not be 100% complementary to its target nucleic acid sequence to be specifically hybridizable. In particular embodiments, an oligonucleotide is considered to be specifically hybridizable when binding of the oligonucleotide to a target nucleic acid sequence interferes with the normal function of the target nucleic acid and results in a loss or altered utility or expression therefom. In preferred embodiments, there is a sufficient degree of complementarity between the oligonucleotide and target nucleic acid to avoid or minimize non-specific binding of the oligonucleotide to undesired non-target sequences under the conditions in which specific binding is desired (e.g., under physiological conditions in the case of in vivo assays or therapeutic treatment, and in the case of in vitro assays, under conditions in which the assays are performed). It is well within the level of skill of scientists in the oligonucleotide field to routinely determine when conditions are optimal for specific hybridization to a target nucleic acid with minimal non-specific hybridization events. Thus, in some embodiments, oligonucleotides in the complexes of the invention include 1, 2, or 3 base substitutions compared to the corresponding complementary sequence of a region of a target DNA or RNA sequence to which it specifically hybridizes. In some embodiments, the location of a non-complementary nucleobase is at the 5' end or 3' end of an antisense oligonucleotide. In additional embodiments, a non-complementary nucleobase is located at an internal position in the oligonucleotide. When two or more non-complementary nucleobases are present in an oligonucleotide, they may be contiguous (i.e., linked), non-contiguous, or both. In some embodiments, the oligonucleotides in the complexes of the invention have at least 85%, at least 90%, or at least 95% sequence identity to a target region within the target nucleic acid. In other embodiments, oligonucleotides have 100% sequence identity to a polynucleotide sequence within a target nucleic acid. Percent identity is calculated according to the number of bases that are identical to the corresponding nucleic acid sequence to which the oligonucleotide being compared. This identity may be over the entire length of the oligomeric compound (i.e., oligonucleotide), or in a portion of the oligonucleotide (e.g., nucleobases 1-20 of a 27-mer may be compared to a 20-mer to determine percent identity of the oligonucleotide to the oligonucleotide). Percent identity between an oligonucleotide and a target nucleic acid can routinely be determined using alignment programs and BLAST programs (basic local alignment search tools) known in the art (see, e.g., Altschul et al., J. Mol. Biol., 1990, 215, 403-410; Zhang and Madden, Genome Res., 1997, 7, 649-656).

As used herein, the terms "target nucleic acid" and "nucleic acid encoding a target" are used to encompass any nucleic acid capable of being targeted including, without limitation, DNA encoding a given molecular target (i.e., a protein or polypeptide), RNA (including miRNA, pre-mRNA and mRNA) transcribed from such DNA, and also cDNA derived from such RNA. Exemplary DNA functions to be interfered with include replication, transcription and translation. The overall effect of such interference with target nucleic acid function is modulation of the expression of the target molecule. In the context of the present invention, "modulation" means a quantitative change, either an increase (stimulation) or a decrease (inhibition), for example in the expression of a gene. The inhibition of gene expression through reduction in RNA levels is a preferred form of modulation according to the present invention.

A "chromophore" is a group, substructure, or molecule that is responsible for the absorbance of light. Typical chromophores each have a characteristic absorbance spectrum.

A "fluorophore" is a chromophore that absorbs light at a characteristic wavelength and then re-emits the light most typically at a characteristic different wavelength. Fluorophores are well known to those of skill in the art and include, but are not limited to xanthenes and xanthene derivatives, rhodamine and rhodamine derivatives, cyanines and cyanine derivatives, coumarins and coumarin derivatives, and chelators with the lanthanide ion series. A fluorophore is distinguished from a chromophore which absorbs, but does not characteristically re-emit light.

An "H-type excitonic structure" (HES) refers to two or more fluorophores whose transition dipoles are arranged in a parallel configuration resulting in a splitting of the excited singlet state; transitions between a ground state and an upper excited state are considered allowed and transitions between a ground state and lower excited state forbidden. HES formation in connection with certain fluorophores is known in the art and the invention encompasses the attachment of these fluorophores to oligonucleotides (e.g., diagnostic and therapeutic oligonucleotides) and the use of the resulting HES-oligonucleotides according to the methods described herein. Examples of HES forming fluorophores that can be used according to the methods of the invention are disclosed herein or otherwise known in the art and include, but are not limited to, xanthenes and xanthene derivatives, cyanine and cyanine derivatives, coumarins and chelators with the lanthanide ion series.

The term "HES-oligonucleotide" refers to a complex of one or more oligonucleotide strands (e.g., a single strand, double strand, triple strand or a further plurality of strands of linear or circular oligonucleotides containing the same, complementary or distinct oligonucleotide sequences) that contain 2 or more fluorophores that form an HES. The fluorophores of the HES-oligonucleotide may be attached at the 5' and/or 3' terminal backbone phosphates and/or, at another base within an oligonucleotide or in different oligonucleotides so long as the collective HES-oligonucleotide contains one or more HES. The fluorophores are optionally attached to the oligonucleotide via a linker, such as a flexible aliphatic chain.

An HES-oligonucleotide may contain 1, 2, 3, 4, or more HES. Additionally, an HES in an HES-oligonucleotide may contain 2, 3, 4 or more of the same or different fluorophores. See, e.g., Toptygin et al., Chem. Phys. Lett 277:430-435 (1997). In some embodiments, an HES is formed as a consequence of fluorophore aggregates between HES-oligonucleotides of the invention. In some embodiments, an HES is formed as a consequence of fluorophore aggregates between oligonucleotides of the invention that are singly labeled with a fluorophore capable of forming an HES.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a subject (e.g., a mammal such as a mouse, rat, rabbit, or a primate such as a human), without the production of therapeutically prohibitive undesirable physiological effects such as nausea, dizziness, gastric upset and the like.

As used herein, a "pharmaceutical composition comprising an antisense oligonucleotide" refers to a composition comprising an HES-oligonucleotide complex and a pharmaceutically acceptable diluent. By way of example, a suitable pharmaceutically acceptable diluent is phosphate-buffered saline.

A "stabilizing modification" or "stabilizing motif" means providing enhanced stability, in the presence of nucleases, relative to that provided by 2'-deoxynucleosides linked by phosphodiester internucleoside linkages. Thus, such modifications provide "enhanced nuclease stability" to oligonucleotides. Stabilizing modifications include at least stabilizing nucleosides and stabilizing internucleoside linkage groups.

The term "in vivo organism" refers to a contiguous living system capable of responding to stimuli such as reproduction, growth and development, and maintenance of homeostasis as a stable whole. Examples include mammals, plants, and microorganisms such as bacteria, protozoa, and viruses.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The terms "administering" and "administration" as used herein, refer to adding a chemical such as an oligonucleotide to a subject in vivo or ex vivo. Thus, administering encompasses both the addition of an HES-oligonucleotide directly to a subject and also contacting cells with HES-oligonucleotide compositions and then introducing the contacted cells into a subject. In one embodiment, cells removed from a subject are contacted with an HES-oligonucleotide and the contacted cells are then re-introduced to the subject.

The term "contacting" refers to adding a chemical such as an oligonucleotide to an in vivo organism such as a mammal, plant, bacterium, or virus. For mammals, common routes of contacting include peroral (through the mouth), topical (skin), transmucosal (nasal, buccal/sublingual, vaginal, ocular and rectal), inhalation (lungs), intramuscular (muscle) and intravenous (vein). For bacteria and viruses contact may be delivery inside a cell or tissue of a host organism.

"Treating" or "treatment" includes the administration of an HES-oligonucleotide to prevent or delay the onset of the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder. Treatment can be with an HES-oligonucleotide complex containing composition alone, or in combination with 1, 2, 3 or more additional therapeutic agents.

The term "therapeutically effective amount" refers to an amount of an HES-oligonucleotide complex ("therapeutic agent") or other drug effective to achieve a desired therapeutic result and/or to "treat" a disease or disorder in a subject. The term "therapeutically effective amount" may also refer to an amount required to produce a slowing of disease progression, an increase in survival time, and/or an improvement in one or more indicators of disease or the progression of a disease in a subject suffering from the disease. For example, in the case of cancer, a therapeutically effective amount an HES-oligonucleotide complex may: reduce angiogenesis and neovascularization; reduce the number of cancer cells, a therapeutically effective amount an HES-oligonucleotide complex may reduce tumor size, inhibit (i.e., slow or stop) cancer cell infiltration into peripheral organs, inhibit (i.e., slow or stop) tumor metastasis, inhibit or slow tumor growth or tumor incidence, stimulate immune responses against cancer cells and/or relieve one or more symptoms associated with the cancer. In the case of an infectious disease, a therapeutically effective amount an HES-oligonucleotide complex may be associated with a reduced number of the infectious agent (e.g., viral load) and/or in amelioration of one or more symptoms or conditions associated with infection caused by the infectious agent. A "therapeutically effective amount" also may refer to an amount effective, at dosages and for periods of time necessary, to achieve a desired therapeutic result. A therapeutically effective amount of an HES-oligonucleotide complex of the invention may vary according to factors such as, the disease state, age, sex, and weight of the subject, and the ability of the HES-oligonucleotide complex to elicit a desired response in the subject. A therapeutically effective amount is also one in which any toxic or detrimental effects of the HES-oligonucleotide complex are outweighed by the therapeutically beneficial effects.

"Therapeutic index" means the ratio of the dose of an HES-oligonucleotide complex which produces an undesired effect to the dose which causes desired effects. In the context of the present disclosure, an HES-oligonucleotide complex exhibits an "improved therapeutic index" when activity is retained, but undesired effects are reduced or absent. For example, an HES-oligonucleotide complex having an improved therapeutic index retains the ability to inhibit miRNA activity without resulting in undesired effects such as immunostimulatory activity, or, at least, without resulting in undesired effects to a degree that would prohibit administration of the complex.

As used herein a "therapeutic oligonucleotide" refers to an oligonucleotide capable of achieving a desired therapeutic result and/or to "treat" a disease or disorder in a subject or ex vivo when administered at sufficient doses. Such desirable results include for example, a slowing of disease progression, an increase in survival time, and/or an improvement in one or more indicators of disease, disease progression, or disease related conditions in a subject suffering from the disease. Exemplary therapeutic oligonucleotides include an siRNA, an shRNA, a Dicer substrate (e.g., dsRNA), an miRNA, an anti-miRNA, an antisense, a decoy, an aptamer and a plasmid capable of expressing a siRNA, a miRNA, a ribozyme, an antisense oligonucleotide, or a protein coding sequence. Oligonucleotides such as probes and primers that are not able to achieve a desired therapeutic result are not considered therapeutic oligonucleotides for the purpose of this disclosure. On average, less than 1% of mRNA is a suitable target for antisense oligonucleotides. Numerous antisense oligonucleotides suitable for incorporation to the HES-oligonucleotides of the invention are described herein or otherwise known in the art. Likewise, suitable therapeutic oligonucleotides can routinely be designed using guidelines, algorithms and programs known in the art (see, e.g., Aartsma-Rus et al., Mol Ther 17(3) 548-553 (2009) and Reynolds et al., Nat. Biotech. 22(3):326-330 (2004), and Zhang et al., Nucleic Acids Res. 31e72 (2003), the contents of each of which is herein incorporated by reference in its entirety). Suitable therapeutic oligonucleotides can likewise routinely be designed using commercially available programs (e.g., MysiRNA-Designer, AsiDesigner (Bioinformatics Research Center, KRIBB), siRNA Target Finder (Ambion), Block-iT RNAi Designer (Invitrogen), Gene specific siRNA selector (The Wistar Institute), siRNA Target Finder (GeneScript), siDESIGN Center (Dharmacon), SiRNA at Whitehead, siRNA Design (IDT), D: T7 RNAi Oligo Designer (Dudek P and Picard D.), sfold-software, and RNAstructure 4.5); programs available over the internet such as, human splicing finder software (e.g., at ".umd.be/HSF/") and Targetfinder (available at "bioit.org.cn/ao/targetfinde r"); and commercial providers (e.g., Gene Tools, LLC). In certain instances, an HES-oligonucleotide and a therapeutic oligonucleotide may be used interchangeably herein unless the context clearly dictates otherwise.

BRIEF DESCRIPTION OF THE DRAWINGS/FIGURES

FIG. 1 shows fields histograms of blood cells isolated from BALB/C mice three hours after an injection of 200 microliters of buffer (PBS) or a Dicer substrate. The latter contains a sequence for a gene not present in these mice. In Panel a, cells were isolated after a single ip injection of PBS or the Dicer substrate at a concentration of 1.5 mg/kg. In Panel b, cells were isolated after an iv injection of PBS, the Dicer substrate at a concentration of 1.5 mg/kg, or the Dicer substrate at a concentration of 0.75 mg/kg.

FIG. 2 shows (left column) emission spectra and (right column) hplc chromatograms of individual complementary single fluorophore-labeled strands of RNA (top two rows) before and (bottom row) after addition to each other. The middle column of the figure shows the fluorescence intensity of the sense strand alone (between 0 and ca. 80 sec.) followed by quenching upon addition of the antisense strand (at ca. 80 sec.).

FIG. 3 shows the fluorescence intensity of the duplex formed between a labeled sense and labeled antisense strand of RNA as a function of time after addition of the recombinant Dicer enzyme.

FIG. 4 shows fluorescence intensity of single blood cells from mice transgenic for eGFP. Histogram from control cells and superimposed on that of cells exposed to a duplex RNA targeting eGFP.

DETAILED DESCRIPTION OF THE INVENTION

Figure 1A:
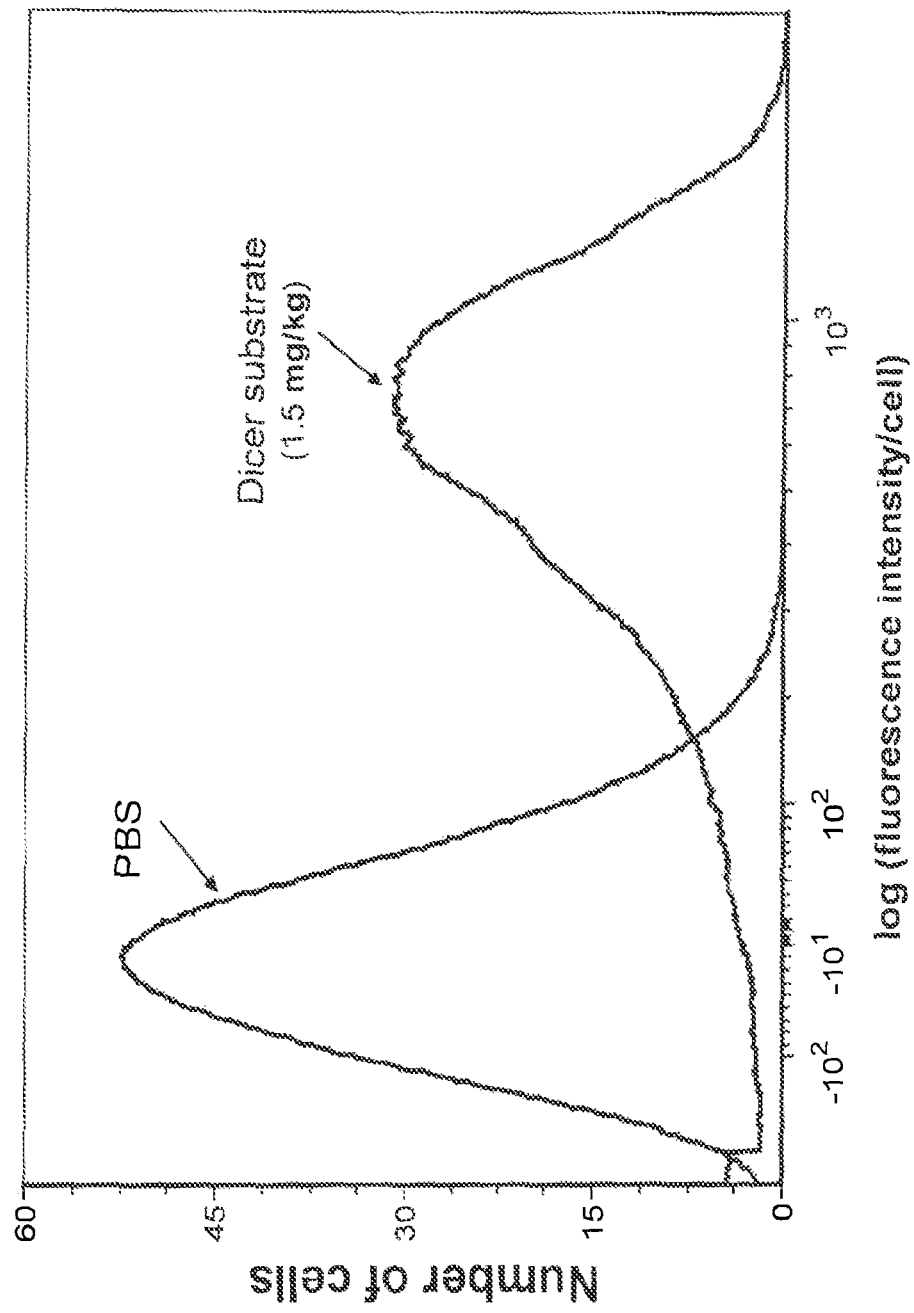

Molecular targets for detection and treatment of pathologic conditions such as cancer, infectious diseases, and neurodegenerative disorders can be unique DNA and RNA sequences. Studies in which binding between such targets and probes containing complementary sequences, a process known as hybridization, have been carried out with high precision and specificity; moreover, these data have provided a basis for optimism for development of treatments not currently available. However, such studies have largely been carried out under nonphysiologic conditions, e.g., in solution or in permeabilized or fixed cells and tissues. Unfortunately, when the same probes have been tried under physiologic conditions, due to the complementary sequences' sizes and charges combined with the presence of permeability barriers, e.g., host cell membranes, extracellular matrices, or cell walls, accessibility to these targets has often been considerably limited resulting in reduced effectiveness. Thus, in the past decade many resources have been directed toward developing methods of delivering oligonucleotide sequences capable of blocking gene transcription and translation in vivo.

Both biologic and chemical approaches have been used to develop delivery methods. For example, a biologic approach has been the construction of several viral vectors with promoter-expressed sequences while chemically-based delivery vehicles have been created by conjugation of nucleic acids with a variety of molecules including cholesterol, sugars, aptamers, and antibodies. However, the most studied chemical in vivo delivery system has utilized nanoparticles wherein nucleic acids are encapsulated in liposomes which are vesicles composed of lipid bilayers. The latter when decorated with polyethylene glycol (PEG) polymer chains for enhanced stability are termed SNALPs and they are sometimes further modified with peptide ligands on the nanoparticle surface for targeting receptors on specific cell types.

Although some success has been achieved with the above approaches, the following problems have been encountered: with viral delivery, there is a high potential for triggering immunogenicity in the host. Additionally, the risk of mutations or aberrant gene expression in the host due to mutations in the viral sequence must be monitored. As for the in vivo chemical delivery vehicles, unfortunately, even with enhanced modifications for specificity, delivery has been shown to be lacking with respect to: (1) Specific uptake by target cells. Rather, cells of the reticuloendothelial system nonspecifically take up nucleic acid constructs, particularly nanoparticles, by a phagocytic-like process. (2) Even when targeting of the desired cell is successful, internalization of the probe with or without the delivery vehicle is often into the cells' endocytic system with the oligonucleotide ending up in lysosomes where the chemical environment, e.g., low pH, can lead to (a) destruction of the nucleic acid or (b) sequestration from the targeted mRNA in the cytoplasm or DNA in the nucleus.

In contrast to the above described delivery vehicles, the present invention provides a highly efficient in vitro and in vivo oligonucleotide delivery system that requires the administration of orders of magnitude of less oligonucleotide to achieve therapeutic effect than that required using conventional delivery technologies. The HES-oligonucleotide delivery vehicles of the invention are sequence independent (e.g., delivery of nucleic acids, modified nucleic acids, PNAs, morpholinos) and exploit passive diffusion to bypass cellular endoctyic systems, thereby providing access to all intracellular environments and increasing the delivery of oligonucleotides (e.g., therapeutic oligonucleotides such as, siRNA, shRNA, Dicer substrates (e.g., dsRNA), miRNA, anti-miRNA, decoys, aptamers and antisense to for example, targeted RNA in the cell cytoplasm or DNA in the nucleus. In particular, in preferred embodiments, the invention uses HES-oligonucleotide complexes comprising an oligonucleotide and 2 or more fluorophores capable of forming an HES to deliver a nucleic acid sequence of interest into the cytoplasm and/or nucleus of cells and tissues of an organism in vivo. The HES-oligonucleotide delivery vehicle is non-toxic to cells and organisms. The superior sequence-independent cell membrane permeability of delivery vehicles of the invention facilitates the ability of oligonucleotides contained in the HES-oligonucleotide complex to cross membranes in a receptor-independent manner and leads to increased delivery and targeting of the oligonucleotide to complementary nucleic acid sequences in the cytoplasm as well as in the nucleus of live cells. HES-oligonucleotide delivery systems of the invention can also be used to target nucleic acid sequences of bacterial or viral origin. Moreover, the HES-oligonucleotide delivery vehicles of the invention have applications in the delivery of a diverse array of diagnostic and functional oligonucleotides to cells in vivo, including but not limited to, antisense oligonucleotides, siRNAs, shRNAs, Dicer substrates, ribozymes, miRNAs, anti-miRNAs, aptamers, decoys, protein coding sequences, or any nucleic acid sequence in a living organism. Such living organisms include, for example, mammals, plants, and microorganisms such as bacteria, protozoa, and viruses.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The fluorophores in the oligonucleotide complexes of the invention can be any fluorophores in the complex that are capable of forming an HES with a homotypic or heterotypic cognate fluorophore(s) in the complex. In some embodiments, the HES-oligonucleotide complex comprises 2 fluorophores capable of forming an H-type excitonic structure. In additional embodiments, the HES-oligonucleotide complex comprises 3, 4, 5 or more fluorophores capable of forming an H-type excitonic structure. In further embodiments, the HES-oligonucleotide complex contains from about 2-20, from about 2-10, from about 2-6, or from about 2-4 fluorophores capable of forming an H-type excitonic structure. In additional embodiments, the HES-oligonucleotide complex comprises 3, 4, 5 or more fluorophores capable of forming an H-type excitonic structure. Two or more fluorophores are said to quench each other in an HES when their aggregate fluorescence is detectably less than the aggregate fluorescence of the fluorophores when they are separated, e.g. in solution at approximately 1 uM or less. The maximum of an HES absorbance spectrum as compared with spectra of the individual fluorophores shows the maximum absorbance wavelength to be shifted to a shorter wavelength, i.e., a blue shift. Fluorescence intensity of H-type Excitonic Structures or aggregates (herein "HES") exhibits an intensity less than those of its components. Either a blue shift in the absorbance spectrum or a decrease in fluorescence intensity behavior of the H-type excitonic structures or aggregates can be utilized as an indicator of a signal reporter moiety. In preferred embodiments two or more fluorophores in the HES-oligonucleotide complex increase or quench by at least 50%, preferably by at least 70%, more preferably by at least 80%, and most preferably by at least 90%, 95% or even at least 99%. Examples of fluorophores that can form H-type excitonic structures include xanthenes, cyanines and coumarins.

In some embodiments, the HES-oligonucleotide complex contains a fluorophore selected from the group consisting of: carboxyrhodamine 110, carboxytetramethylrhodamine, carboxyrhodamine-X, diethylaminocoumarin and a carbocyanine dye. In further embodiments, the HES-oligonucleotide complex contains a fluorophore selected from the group consisting of: Rhodamine Green™ carboxylic acid, succinimidyl ester or hydrochloride; Rhodamine Green™ carboxylic acid, trifluoroacetamide or succinimidyl ester; Rhodamine Green™-X succinimidyl ester or hydrochloride; Rhodol Green™ carboxylic acid, N,O-bis-(trifluoroacetyl) or succinimidyl ester; bis-(4-carboxypiperidinyl) sulfonerhodamine or di(succinimidyl, ester); 5-(and-6)-carboxynaphthofluorescein, 5-(and-6)-carboxynaphthofluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(and-6)-carboxyrhodamine 6G succinimidyl ester; 5-carboxy-2',4',5',7'-tetrabromosulfonefluorescein succinimidyl ester or bis-(diisopropylethyl ammonium) salt; 5-carboxytetramethylrhodamine; 6-carboxytetramethylrhodamine; 5-(and-6)-carboxytetramethylrhodamine; 5-carboxytetra methylrhodamine succinimidyl ester; 6-carboxytetramethylrhodamine succinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)-carboxy-X-rhodamine succinimidyl ester; 5-carboxy-X-rhodamine triethylammonium salt; Lissamine™ rhodamine B sulfonyl chloride; malachite green isothiocyanate; Rhodamine Red™-X succinimidyl ester; 6-(tetramethylrhodamine-5-(and-6)-carboxamido)hexanoic acid succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; X-rhodamine-5-(and-6)-isothiocyanate; and the carbocyanines.

In some embodiments, the HES-oligonucleotide complex contains a hetero-HES composed of different fluorophore. In particular embodiments, the hetero-HES contains a rhodamine or rhodamine derivative and a fluorescein or a fluorescein derivative or two carbocyanines. In further embodiments, the hetero-HES contains a fluorescein or fluorescein derivative selected from: 6-carboxy-4',5'-dichloro-2',7'-dimethoxyfluorescein succinimidyl ester; 5-(and-6)-carboxyeosin; 5-carboxyfluorescein; 6-carboxyfluorescein; 5-(and-6)-carboxyfluorescein; 5-carboxyfluorescein-bis-(5-carboxymethoxy-2-nitrobenzyl)ether, -alanine-carboxamide, or succinimidyl ester; 5-carboxyfluorescein succinimidyl ester; 6-carboxyfluorescein succinimidyl ester, 5-(and-6)-carboxyfluorescein succinimidyl ester; 5-(4,6-dichlorotriazinyl)aminofluorescein; 2',7'-difluorofluorescein; eosin-5-isothiocyanate; erythrosin-5-isothiocyanate; 6-(fluorescein-5-carboxamido) hexanoic acid or succinimidyl ester; 6-(fluorescein-5-(and-6)-carboxamido) hexanoic acid or succinimidyl ester; fluorescein-5-EX succinimidyl ester; fluorescein-5-isothiocyanate; and fluorescein-6-isothiocyanate.

Oligonucleotides

In the context of this invention, the term "oligonucleotide" refers to an oligomer or polymer of ribonucleic acid (RNA), deoxyribonucleic acid (DNA) or mimetics thereof. This term includes oligonucleotides composed of naturally-occurring nucleobases, sugars and covalent internucleoside (backbone) linkages (i.e., "unmodified oligonucleotide), as well as oligomeric compounds having non-naturally-occurring nucleobases, sugars and/or internucleoside linkages and/or analogs of DNA and/or RNA which function in a similar manner (i.e., nucleic acid "mimetics"). Such mimetic oligonucleotide are often preferred over native forms because of desirable properties such as: enhanced affinity for nucleic acid target and increased stability in the presence of nucleases. For example, as used herein, the term "oligonucleotide" includes morpholino (MNO) wherein one or more ribose rings of the nucleotide backbone is replaced with a morpholine ring and phosphorodiamidate morpholino oligomers (PMOs) wherein one or more ribose ring of the nucleotide backbone is replaced with a morpholine ring and the negatively charged intersubunit linkages are replaced by uncharged phosphorodiamidate linkages. Likewise, the term oligonucleotide encompasses PNAs in which one or more sugar phosphate backbone of an oligonucleotide is replaced with an amide containing backbone. For the purposes of this specification, and as sometimes referenced in the art, modified oligonucleotides that do not have a phosphorus atom in their internucleoside backbone can also be considered to be oligonucleosides. Moreover the oligonucleotides may be refers to as oligomers.

The delivery of HES-oligonucleotide vehicles of the invention are sequence independent and accordingly, the oligonucleotides contained in the HES-oligonucleotide vehicles can be any form of nucleic acid or mimetic that is known that would be desirable to be introduced into a cell.

Oligonucleotides in the HES-oligonucleotide vehicles can be in the form of single-stranded, double-stranded, circular or hairpin oligonucleotides. In some embodiments, the oligonucleotides are single-stranded DNA, RNA, or a nucleic acid mimetic (e.g., PMO, MNO, PNA, or oligonucleotides containing one or more modified nucleotides such as a 2'OME and LNA). In some embodiments, the oligonucleotides are double-stranded DNA, RNA, nucleic acid mimetic, DNA/nucleic acid mimetic, DNA-RNA and RNA-nucleic acid mimetic.

The inventors have surprisingly discovered that complexes containing HES-oligonucleotides such as ssDNA and dsRNA display superior sequence independent intracellular delivery that require the administration of orders of magnitude of less oligonucleotides that that required by conventional oligonucleotide delivery vehicles. Examples of single-stranded nucleic acids contained in the complexes of the invention include, but are not limited to, antisense, siRNA, shRNA, ribozymes, miRNA, antimiRNA, triplex-forming oligonucleotides and aptamers.

In some embodiments an oligonucleotide in an HES-oligonucleotide complex is single stranded DNA (ssDNA). In preferred embodiments, at least a portion of the ssDNA oligonucleotide specifically hybridizes with a target RNA to form an oligonucleotide-RNA duplex. In further preferred embodiments, the oligonucleotide-RNA duplex is susceptible to an RNase cleavage mechanism (e.g., RNase H). In some embodiments, a single stranded oligonucleotide in the complex comprises at least one modified backbone linkage, at least one modified sugar, and/or at least one modified nucleobase (e.g., as described herein). In some embodiments, a single stranded oligonucleotide in the complex comprises at least one modified backbone linkage, at least one modified sugar, and/or at least one modified nucleobase (e.g., as described herein) and is capable of forming an oligonucleotide-RNA duplex that is susceptible to an RNase cleavage mechanism. In particular embodiments, the single stranded oligonucleotide is a gapmer (i.e., as described herein or otherwise known in the art). In additional embodiments, an oligonucleotide in the HES-oligonucleotide complex comprises at least one modified backbone linkage, at least one modified sugar, and/or at least one modified nucleobase that decreases the sensitivity of the oligonucleotide to an RNase cleavage mechanism (e.g., as described herein). In particular embodiments, the single stranded oligonucleotide comprises at least one 2'OME, LNA, MNO or PNA motif The inventors have also surprisingly discovered that HES-oligonucleotide complexes containing double stranded oligonucleotides display superior sequence independent intracellular delivery of the double stranded oligonucleotides (also in the nanomolar and mid-micromolar range) over conventional oligonucleotide delivery vehicles. Examples of double-stranded DNA oligonucleotides contained in the complexes of the invention include, but are not limited to, dsRNAi and dicer substrates and other RNA interference reagents, and sequences corresponding to structural genes and/or control and termination regions.

In some embodiments, the oligonucleotide is a linear double-stranded RNA (dsRNA). In preferred embodiments, the ds-RNA is susceptible to an RNase cleavage mechanism (e.g., Dicer and Drosha (an RNase III enzyme)). In additional embodiments, the dsRNA is able to be inserted into the RNA Induced Silencing Complex (RISC) of a cell. In further embodiments, a RNA strand of the dsRNA is able to use the RISC complex to effect cleavage of an RNA target.

In additional embodiments, the HES-oligonucleotide complex contains a double stranded oligonucleotide in which one or both oligonucleotides contain at least one modified backbone linkage, at least one modified sugar, and/or at least one modified nucleobase. In preferred embodiments, the double strand oligonucleotide is susceptible to an RNase cleavage mechanism (e.g., Dicer and Drosha (an RNase III enzyme). In additional embodiments, the double stranded oligonucleotide is able to be inserted into the RNA Induced Silencing Complex (RISC) of a cell. In further embodiments, an oligonucleotide strand of the double stranded oligonucleotide is able to use the RISC complex to effect cleavage of an RNA target.

In further embodiments the HES-oligonucleotide complex contains a triple stranded oligonucleotide. In some embodiments the oligonucleotide is a triple-stranded DNA/RNA chimeric. In some embodiments, the oligonucleotide complex contains at least one oligonucleotide comprising at least one modified backbone linkage, at least one modified sugar and/or at least one modified nucleobase. In particular embodiments, at least one oligonucleotide in the complex comprises at least one 2'OME, LNA, MNO or PNA motif.

Oligonucleotides in the HES-oligonucleotide vehicles are routinely prepared linearly but can be joined or otherwise prepared to be circular and may also include branching. Separate oligonucleotides can specifically hybridize to form double stranded compounds that can be blunt-ended or may include overhangs on one or both termini. In particular embodiments, double stranded oligonucleotides (e.g., dsRNA and double stranded oligonucleotide in which at least one of the oligonucleotide strands is a nucleic acid mimetic) contained in the complexes of the invention are between 21-25 nucleotides in length and have 1, 2, or 3 nucleotide overhangs at either or both ends.

Oligonucleotides in the HES-oligonucleotide complexes of the invention may be of various lengths, generally dependent upon the particular form of nucleic acid or mimetic and its intended use. In some embodiments, nucleic acid/oligonucleotides in the HES-oligonucleotide complexes of the invention range from about 5 nucleotides to about 500 nucleotides, and preferably from about 10 nucleotides to about 100 nucleotides in length.

In some embodiments, an oligonucleotide in the HES-oligonucleotide complex comprises at least 8 contiguous nucleobases that are complementary to a target nucleic acid sequence. In various related embodiments, an oligonucleotide in the HES-oligonucleotide complex is from about 8 to about 100 monomeric subunits (used interchangeably with the term "nucleotides" herein) or from about 8 to about 50 nucleotides in length.

In additional embodiments an oligonucleotide in the HES-oligonucleotide complex ranges in length from about 8 to about 30 nucleotides, from about 15 to about 30 nucleotides, from about 20 to about 30 nucleotides, from about 18 to 26 nucleotides, from about 19 to 25 nucleotides, from about 20 to 25 or from about 21 to 25 nucleotides.

In further embodiments, an oligonucleotide in the HES-oligonucleotide complex is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 subunits (nucleotides) in length. In particular embodiments, the oligonucleotides are 19, 20, 21, 22, 23, 24 or 25 nucleotides in length.

In particular embodiments, the HES-oligonucleotide complex contains a double strand of RNA oligonucleotides of between 21-25 nucleotides in length and have 1, 2, or 3 nucleotide overhangs at either or both ends. In other embodiments, the HES-oligonucleotide complex contains a double strand of oligonucleotides in which at least one of the oligonucleotide strands is a nucleic acid mimetic of between 21-25 nucleotides in length and the double stranded oligonucleotide has a 1, 2, or 3 nucleotide overhang at either or both ends.

Oligonucleotides Containing Modifications

HES-oligonucleotide complexes of the invention preferably include oligonucleotides containing one or more modified internucleoside linkages, modified sugar moieties and/or modified nucleobases. Such modified oligonucleotides (i.e., mimetics) are typically preferred over native forms because of desirable properties including for example, enhanced cellular uptake, enhanced affinity for nucleic acid target, increased stability in the presence of nucleases and/or increased inhibitory activity.

Modified Internucleoside Linkages

The term "oligonucleotide" as used herein, refers to those oligonucleotides that retain a phosphorus atom in their internucleoside backbone as well as those that do not have a phosphorus atom in their internucleoside backbone. In some embodiments, oligonucleotides in the HES-oligonucleotide complexes of the invention comprise one or more modified internucleoside linkages. Modified internucleoside linkages in the oligonucleotides of the invention may include for example, any manner of internucleoside linkages known to provide enhanced nuclease stability to oligonucleotides relative to that provided by phosphodiester internucleoside linkages. Oligonucleotides having modified internucleoside linkages include internucleoside linkages that retain a phosphorus atom as well as internucleoside linkages that do not contain phosphorus. In some embodiments the oligonucleotides comprise modified internucleoside linkages that alternate between modified and unmodified internucleoside linkages. In some embodiments most of the internucleoside linkages in the oligonucleotide are modified. In further embodiments, every internucleoside linkage in the oligonucleotide is modified.

Preferred modified oligonucleotide backbones include, for example, phosphorothioates, chiral phosphorothioates, phosphorodithioates, phosphodiesters, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e., a single inverted nucleoside residue which may be abasic (the nucleobase is missing or has a hydroxyl group in place thereof). Various salts, mixed salts and free acid forms are also included.

In preferred embodiments, the HES-oligonucleotide complexes of the invention include at least one phosphorothioate (PS) internucleoside linkage wherein one of the nonbridging oxygen atoms in the phosphodiester bond is replaced by sulfur. Oligonucleotides containing PS internucleoside linkage form regular Watson-Crick base pairs, activate RNase H, carry negative charges for cell delivery and display other additional desirable pharmacokinetic properties. In some embodiments the at least one modified internucleoside linkage is phosphorothioate. In some embodiments, at least 2, 3, 4, 5, 10 or 15 of the internucleoside linkages contained in the oligonucleotide is a phosphorothioate linkage. In some embodiments, at least 1-10, 1-20, 1-30 of the modified internucleoside linkages is a phosphorothioate linkage. In some embodiments, at least 2, 3, 4, 5, 10 or 15 of the modified internucleoside linkages is a phosphorothioate linkage. In additional embodiments, each internucleoside linkage of an oligonucleotide is a phosphorothioate internucleoside linkage.

Another suitable phosphorus-containing modified internucleoside linkage is the N3'-P5' phosphoroamidates (NPs) in which the 3'-hydroxyl group of the 2'-deoxyribose ring is replaced by a 3'-amino group. Oligonucleotides containing NPs internucleoside linkages exhibit high affinity towards complementary RNA and resistance to nucleases. Since phosphoroamidate do not induce RNase H cleavage of the target RNA, oligonucleotides containing these internucleoside linkages have applications in those instances where RNA integrity needs to be maintained, such as those instances in which the oligonucleotides modulation mRNA splicing. In some embodiments, at least 2, 3, 4, 5, 10 or 15 of the internucleoside linkages contained in the oligonucleotide is a phosphoroamidate linkage. In some embodiments, at least 1-10, 1-20, 1-30 of the modified internucleoside linkages is a phosphoroamidate linkage. In some embodiments, at least 2, 3, 4, 5, 10 or 15 of the modified internucleoside linkages is a phosphoroamidates linkage. In additional embodiments, each internucleoside linkage of an antisense compound is a phosphoroamidate internucleoside linkage.

Numerous modified internucleoside linkages and their method of synthesis are known in the art and encompassed by the modifications that may be contained in the oligonucleotides of the invention. Exemplary U.S. patents that teach the preparation of phosphorus-containing internucleoside linkages include, but are not limited to, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,489,677; 5,453,496; 5,455,233; 5,466,677; 5,476,925; 5,519,126; 5,527,899; 5,536,821; 5,541,306; 5,550,111; 5,563,253; 5,565,555; 5,602,240; 5,571,799; 5,587,361; 5,625,050; 5,646,269; 5,663,312; 5,672,697; 5,677,439; and 5,721,218; each of which is herein incorporated by reference in its entirety.

HES-oligonucleotide complexes containing oligonucleotides that do not include a phosphorus atom are also encompassed by the invention. Examples of such oligonucleotides include those containing backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These modified backbones include, but are not limited to oligonucleotides having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Methods of making oligonucleotides containing backbones that do not include a phosphorous atom are known in the art and include, but are not limited to, those methods and compositions disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,646,269; 5,663,312; 5,633,360; 5,677,437; 5,677,439; 5,792,608; and each of which is herein incorporated by reference in its entirety.

In some embodiments, oligonucleotides of the invention contain one or more modified backbone linkages selected from: 3'-methylene phosphonate, methylene (methylimino) (also known as MMI), morpholino, locked nucleic acid, and a peptide nucleic acid linkage. The modified backbone linkages may be uniform or may be alternated with other linkages, particularly phosphodiester or phosphorothioate linkages, as long as RNAse H cleavage is not supported.

In some embodiments, the HES complexes contain oligonucleotides that are nucleic acid mimetics. The term mimetic as it is applied to oligonucleotides is intended to include oligonucleotides wherein the sugar or both the sugar and the internucleotide linkage are replaced with alternative groups.

In some embodiments, the complexes of the invention contain an oligonucleotide having one or more morpholino linkages. The RNAse and nuclease resistant properties of morpholinos make them particularly useful in regulating transcription in a cell. Accordingly, in some embodiments, a complex containing a morpholino unit is used to modulate gene expression. In some embodiments, morpholino unit is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino. In particular embodiments, each monomeric unit of the oligonucleotide corresponds to a phosphorodiamidate morpholino (PMO). In additional embodiments a complex containing a morpholino oligonucleotide (e.g., PMO) is used to alter mRNA splicing in a subject. In additional embodiments, a complex containing one or more morpholino nucleobases such as a PMO, is used as an antisense agent.

In additional embodiments, an oligonucleotide a complex of the invention is a peptide nucleic acid (PNA). PNAs are nucleic acid mimetics in which the sugar phosphate backbone of an oligonucleotide is replaced with an amide containing backbone. In particular embodiments, the phosphate backbone of an oligonucleotide is replaced with an aminoethylglycine backbone and the nucleobases are bound directly or indirectly to aza nitrogen atoms of the amide portion of the backbone. Numerous PNAs and methods of making PNAs are known in the art (see, e.g., Nielsen et al., Science, 1991, 254, 1497-150 and U.S. Pat. Nos. 5,539,082; 5,714,331; and 5,719,262, each of which is herein incorporated by reference in its entirety. PNA containing oligonucleotides provide increased stability and favorable hybridization kinetics and have a higher affinity for RNA than DNA compared to unsubstituted counterpart nucleic acids and do not activate RNAse H mediated degradation. PNAs encompassed by the invention include PNA analogues including PNAs having modified backbones with positively charged groups and/or one or more chiral constrained stereogenic centers at the C2(alpha), such as a D-amino acid, or C5(gamma), such as an L-amino acid (e.g., L-lysine) position of one or more monomeric units of the oligonucleotide.

The RNAse and nuclease resistant properties of PNA oligonucleotides make them particularly useful in regulating RNA (e.g., mRNA and miRNA) in a cell via a steric block mechanism. In some embodiments, HES-oligonucleotides comprise at least one PNA oligonucleotide. In some embodiments, HES-oligonucleotides comprise at least one PNA oligonucleotide and modulate gene expression by strand invasion of chromosomal duplex DNA. In a further embodiment, HES-oligonucleotides contain at least one PNA oligonucleotide and alter mRNA splicing in a subject. In additional embodiments, HES-oligonucleotides comprise at least one PNA oligonucleotide such as, a PMO, and act as an antisense.

Similarly, the RNAse and nuclease resistant properties of morpholino containing oligonucleotides make these oligonucleotides useful in regulating RNA (e.g., mRNA and miRNA) in a cell via a steric block mechanism. In some embodiments, HES-oligonucleotides comprise at least one morpholino oligonucleotide such as, a PMO, and modulate gene expression by strand invasion of chromosomal duplex DNA. In a further embodiment, HES-oligonucleotides comprise at least one morpholino oligonucleotide such as, a PMO, and alter mRNA splicing in a subject. In additional embodiments, HES-oligonucleotides comprise at least one morpholino oligonucleotide such as, a PMO, and act as an antisense.

Additionally, the RNAse and nuclease resistant properties of bicyclic sugar-containing nucleotides make these oligonucleotides useful in regulating RNA (e.g., mRNA and miRNA) in a cell via a steric block mechanism. In some embodiments, complexes of the invention contain at least one bicyclic sugar containing nucleotide. In some embodiments, the bicyclic sugar containing nucleotide is a locked nucleic acid (LNA). In further embodiments, the LNA has a 2'-hydroxyl group linked to the 3' or 4' carbon atom of the sugar ring. In a further embodiment, the oligonucleotide comprises at least one locked nucleic acid (LNA) in which a methylene (—CH2-)$_n$ group bridges the 2' oxygen atom and the 4' carbon atom wherein n is 1 or 2. In some embodiments, HES-oligonucleotides comprise at least bicyclic sugar containing nucleotide such as an LNA, and modulate gene expression by strand invasion of chromosomal duplex DNA. In other embodiments, HES-oligonucleotides contain at least one bicyclic sugar oligonucleotide, such as an LNA, and alter mRNA splicing in a subject. In additional embodiments, HES-oligonucleotides comprise at least one bicyclic sugar oligonucleotide, such as an LNA, and act as an antisense.

Modified Sugar Moieties

In some embodiments, oligonucleotides compounds of the invention comprise one or more nucleosides having one or more modified sugar moieties which are structurally distinguishable from, yet functionally interchangeable with, naturally occurring or synthetic unmodified nucleobases. In further embodiments, the oligonucleotide in the HES-oligonucleotide complex comprises a modified sugar at each nucleoside (unit).

Examples of sugar modifications useful in the oligonucleotides of the invention include, but are not limited to, compounds comprising a sugar substituent group selected from: OH; F; O-, S-, or N-alkyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. Examples of 2'-sugar substituent groups useful in the oligonucleotides of the invention include, but are not limited to: OH; F; O-, S-, or N-alkyl; O-, S-, or N-alkenyl; allyl, amino; azido; thio; O-allyl; O(CH2)2SCH3; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In particular embodiments, the oligonucleotides contain at least one 2'-sugar substituent group selected from: O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides contain at least one 2'-sugar substituent group selected from: a $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligonucleotide compound, and other substituents having similar properties.

In particular embodiments, the oligonucleotides in the complexes of the invention comprise at least one 2'-substituted sugar having a 2'-methoxyethoxy (2'-O—CH$_2$CH$_2$OCH$_3$, aka 2'-MOE) substituent group.

In some embodiments the oligonucleotides in the complexes of the invention comprise at least one 2'-modified nucleoside selected from the group: 2'-allyl (2'-CH$_2$—CH—CH$_2$), 2'-O-allyl (2'-O—CH$_2$—CH—CH$_2$), 2'-aminopropoxy (2'-OCH$_2$CH$_2$CH$_2$NH$_2$), and 2'-acetamido (2'-O—CH$_2$C(—O)NR1R1 wherein each R1 is independently, H or C1-C1 alkyl.

In further embodiments, the oligonucleotides in the complexes of the invention comprise at least one 2'-substituted sugar having: a 2'-dimethylaminooxyethoxy (2'-O(CH$_2$)$_2$ON(CH$_3$)$_2$ group, also known as 2'-DMAOE) substituent group; a 2'-dimethylaminoethoxyethoxy (2'-O—CH$_2$—O—CH$_2$—N(CH$_2$)$_2$, also known as 2'-O-dimethylaminoethoxyethyl or 2'-DMAEOE) substituent group; or a 2'-O-methyl (2'-O—CH$_3$) substituent group. In further embodiments, an oligonucleotide in a complex of the invention comprises at least one 2'-substituted sugar having a 2'-fluoro (2'-F) substituent group.

In some embodiments, oligonucleotides in the complexes of the invention contain at least one bicyclic sugar. In specific embodiments, the oligonucleotides have at least one locked nucleic acid (LNA) in which the 2'-hydroxyl group is linked to the 3' or 4' carbon atom of the sugar ring. In a particular embodiment, the oligonucleotides comprise at least one locked nucleic acid (LNA) in which a methylene (—CH2-)$_n$ group bridges the 2' oxygen atom and the 4' carbon atom wherein n is 1 or 2. In another embodiment, the oligonucleotide contains at least one bicyclic modified nucleoside having a bridge between the 4' and the 2' ribosyl ring atoms wherein the bridge is selected from selected from 4'-(CH$_2$)—O-2' (LNA); 4'-(CH$_2$)—S-2; 4'-(CH$_2$)$_2$—O-2' (ENA); 4'-C(CH$_3$)$_2$—O-2; 4'-CH(CH$_3$)—O-2; 4'-CH (CH$_2$OCH$_3$)—O-2; 4'-CH$_2$—N(OCH$_3$)-2; 4'-CH$_2$—O—N (CH$_3$)-2; 4'-CH$_2$—N(R)—O-2; 4'-CH$_2$—CH(CH$_3$)-2' and 4'-CH$_2$—C(—CH$_2$)-2 wherein R is independently, H, a C1-C12 alkyl, or a protecting group. Oligonucleotides in the complexes of the invention may also have at least one of the foregoing sugar configurations and an additional motif such as, alpha-L-ribofuranose, beta-D-ribofuranose or alpha-L-methyleneoxy (4'-CH$_2$—O-2'). Further LNAs useful in of the oligonucleotides of the invention and their preparation are known in the art. See, e.g., U.S. Pat. Nos. 6,268,490, 6,670,461, 7,217,805, 7,314,923, and 7,399,845; WO 98/39352 and WO 99/14226; and Singh et al., Chem. Commun., 1998, 4, 455-456, the contents of each of which is herein incorporated by reference in its entirety.

In some embodiments, oligonucleotides in the complexes of the invention comprise a chemically modified furanosyl (e.g., ribofuranose) ring moiety. Examples of chemically modified ribofuranose rings include, but are not limited to, addition of substituent groups (including 5' and 2' substituent groups, and particularly the 2' position, bridging of non-geminal ring atoms to form bicyclic nucleic acids (BNA), replacement of the ribosyl ring oxygen atom with S, N(R), or C(R1)(R)2 (R—H, C1-C12 alkyl or a protecting group) and combinations thereof. Examples of chemically modified sugars include 2'-F-5'-methyl substituted nucleoside (see e.g., WO 2008/101157, for other disclosed 5',2'-bis substituted nucleosides) or replacement of the ribosyl ring oxygen atom with S with further substitution at the 2'-position (see e.g., US20050130923) or alternatively 5'-substitution of a BNA (WO 2007/134181 wherein LNA is substituted with for example, a 5'-methyl or a 5'-vinyl group).

Complexes containing oligonucleotides comprising at least one nucleotide having a similar modification to those described above, at the 3' position of the sugar on the 3' terminal nucleotide or in 2'-5' linked oligonucleotides and the 5' position of 5' terminal nucleotide are also encompassed by the invention. Representative U.S. patents that teach the preparation of 2'-modified nucleosides contained in the oligonucleotides of the invention include, but are not limited to, U.S. Pat. Nos. 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300;

5,627,053; 5,639,873; 5,646,265; 5,658,873; 5,670,633; 5,700,920; and 5,792,747, each of which is herein incorporated by reference in its entirety.

In some embodiments, the oligonucleotides in the complexes of the invention have at least one heterocyclic bicyclic nucleic acid. For example, in some embodiments, the oligonucleotides have at least one ENA motif (see, e.g., WO 01/49687, the contents of which are herein incorporated by reference in its entirety).

In additional embodiments, the oligonucleotides in the complexes of the invention have at least one replacement of a five-membered furanose ring by a six-membered ring. In at least one embodiment, the oligonucleotides have at least one cyclohexene nucleic acid (CeNAs). They form stable duplexes with complementary DNA or RNA and protect oligonucleotides against nucleolytic degradation.

In some embodiments, the oligonucleotides in the complexes of the invention have at least one tricyclo-DNA (tcDNA).

In particular embodiments, the oligonucleotides in the complexes of the invention contain phosphorothioate backbones and oligonucleosides with heteroatom backbones, such as —CH2-NH—O—CH2-, —CH2-N(CH3)-O—CH2- (also known as a methylene (methylimino) or MMI backbone), —CH2-O—N(CH3)-CH2-, —CH2-N(CH3)-N(CH3)—CH2- and —O—N(CH3)-CH2-CH2-, and an amide backbone (see, e.g., U.S. Pat. No. 5,602,240). In additional embodiments, the oligonucleotides in the complexes of the invention have a phosphorodiamidate backbone structure. In further embodiments, the oligonucleotides in the complexes of the invention have a phosphorodiamidate morpholino (i.e., PMO) backbone structure (see, e.g., U.S. Pat. No. 5,034,506, the contents of which are incorporated herein in their entirety.

Modified Nucleobases

Oligonucleotides in the complexes of the invention may also contain one or more nucleobase modifications which are structurally distinguishable from, yet functionally interchangeable with, naturally occurring or synthetic unmodified nucleobases.

The terms "unmodified" or "natural" nucleobases as used herein, include the purine bases adenine (A) and guanine (G), and the pyrimidine bases thymine (T), cytosine (C) and uracil (U). Modified nucleobases include synthetic and natural nucleobases such as, for example, 5-methylcytosine (5-me-C). In some embodiments, an oligonucleotide in a complex of the invention comprises at least one 5' methylcytosine or a C-5 propyne. In some embodiments, each cytosine in the oligonucleotide is a methylcytosine.

Modified nucleobases are also referred to herein as heterocyclic base moieties and include other synthetic and natural nucleobases such as xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—CC—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 3-deazaguanine and 3-deazaadenine.

Heterocyclic base moieties contained in the oligonucleotides of the invention may also include those in which the purine or pyrimidine base is replaced with other heterocycles such as, 7-deazaadenine, 7-deazaguanosine, 2-aminopyridine and 2-pyridone. Nucleobases that are particularly useful for increasing the binding affinity of the oligonucleotides of the invention include 5-substituted pp' midines, 6-azapyrimidines and N-2, N-6 and 0-6 substituted purines, including 2 aminopropyladenine, 5-propynyluracil and 5-propynylcytosine.

Additional modified nucleobases that are optionally included in the oligonucleotides of the invention, include, but are not limited to, tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), or guanidinium G-clamps and analogs. Representative guanidino substituent groups are disclosed in U.S. Pat. No. 6,593,466, which is hereby incorporated by reference in its entirety. Representative acetamido substituent groups are disclosed in U.S. Pat. No. 6,147,200, which is hereby incorporated by reference in its entirety.

Numerous modified nucleobases encompassed by the oligonucleotides contained in the complexes of the invention and their methods of synthesis are known in the art, and include, for example, the modified nucleobases disclosed in The Concise Encyclopedia Of Polymer Science And Engineering, pages 858-859, Kroschwitz, J. I., ed. John Wiley & Sons, 1990; Englisch et al., Angewandte Chemie, International Edition, 1991, 30, 613; Sanghvi, Y. S., Chapter 15, Antisense Research and Applications, pages 289-302; Crooke, S. T. and Lebleu, B., ed., CRC Press, 1993; and U.S. Pat. Nos. 3,687,808; 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,681,941; 5,750,692; 5,830,653; 5,763,588; 6,005,096; 6,028,183 and 6,007,992 and U.S. Appl. Publ. No. 20030158403, each of which herein incorporated by reference in its entirety.

Chimeric Oligonucleotides:

The oligonucleotides in the complexes of the invention preferably contain one or more modified internucleoside linkages, modified sugar moieties and/or modified nucleobases. In some embodiments, oligonucleotides are chimeric oligonucleotides (e.g., chimeric oligomeric compounds). The terms "chimeric oligonucleotides" or "chimeras" are oligonucleotides that contain at least 2 chemically distinct regions (i.e., patterns and/or orientations of motifs of chemically modified subunits arranged along the length of the oligonucleotide) each made up of at least one monomer unit, i.e., a nucleotide or nucleoside in the case of a nucleic acid based oligonucleotide compound. Chimeric oligonucleotides have also been referred to as for example, hybrids (e.g., fusions) and gapmers. Representative United States patents that teach the preparation of such chimeric oligonucleotide structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Chimeric antisense compounds typically contain at least one region modified so as to confer increased resistance to nuclease degradation, increased cellular uptake, increased binding affinity for the target nucleic acid, and/or increased inhibitory activity. By way of example, gapmers are chimeric oligonucleotides comprising a contiguous sequence of nucleosides that is divided into 3 regions, an central region (gap) flanked by two external regions (wings). Gapmer design typically includes a central region of about 5-10 contiguous 2'-deoxynucleotides which serves as a substrate for RNase H is typically flanked by one or two regions of 2'-modified oligonucleotides that provide enhanced target RNA binding affinity, but do not support RNAse H cleavage of the target RNA molecule. Consequently, comparable results can often be obtained with shorter oligonucleotides having substrate regions when chimeras are used, compared to for example, phosphorothioate deoxyoligonucleotides hybridizing to the same target region. Other chimeric oligonucleotides rely on regions conferring for example, altered levels of binding affinity over the length of an oligonucleotide for its target including regions of modified nucleosides which exhibit either increased or decreased affinity as compared to the other regions. So called, "MOE-gapmers" have 2'-MOE modifications in the wings, often contain full PS backbones, and frequently include 5'MeC modifications on all cytosines.

Alternatively, for those situations in which RNAse H activity may be undesirable, such as in the modulation of RNA processing, it may be preferable to use uniformly modified oligonucleotides, such as designs using modified oligonucleotides that do not support RNAse H activity at each nucleotide or nucleoside position. As used in the present invention the term "fully modified motif" is meant to include a contiguous sequence of sugar modified nucleosides wherein essentially each nucleoside is modified to have the same modified sugar moiety. Suitable sugar modified nucleosides for fully modified oligonucleotides of the invention include, but are not limited to, 2'-Fluoro (2'F), 2'-O(CH$_2$)$_2$OCH$_3$ (2'-MOE), 2'-OCH$_3$ (2'-O-methyl), and bicyclic sugar modified nucleosides. In one aspect the 3' and 5'-terminal nucleosides are left unmodified. In a preferred embodiment, the modified nucleosides are either 2'-MOE, 2'-F, 2'-O-Me or a bicyclic sugar modified nucleoside.

Oligonucleotides used in the compositions of the present invention can also be modified to have one or more stabilizing groups. In some embodiments, the stabilizing groups are attached to one or both termini of oligonucleotides to enhance properties such as, nuclease stability. In some embodiments, the stabilizing groups are cap structures. By "cap structure or terminal cap moiety" is meant chemical modifications, which have been incorporated at either terminus of oligonucleotides (see for example WO 97/26270, which is herein incorporated by reference in its entirety). These terminal modifications may serve to protect the oligonucleotides having terminal nucleic acid molecules from exonuclease degradation and/or may help in the delivery and/or localization of the oligonucleotide within a cell. The oligonucleotide may contain the cap at the 5'-terminus (5'-cap), the 3'-terminus (3'-cap), or both the 5'-terminus and the 3'-termini. In the case of double-stranded oligonucleotides, the cap may be present at either or both termini of either strand. Cap structures are known in the art and include, for example, inverted deoxy abasic caps. Further 3' and 5'-stabilizing groups that can be used to cap one or both ends of an oligonucleotide (e.g., antisense) compound to impart nuclease stability include those disclosed in WO 03/004602, which is herein incorporated by reference in its entirety.

In some embodiments, the 5'-cap of an oligonucleotide contained in an HES-oligonucleotide complex of the invention includes a structure that is an inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (see e.g., WO 97/26270, which is herein incorporated by reference in its entirety).

In some embodiments, the 3'-cap of an oligonucleotide contained in an HES-oligonucleotide complex of the invention includes for example a 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5',5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (see also the stabilizing groups disclosed in Beaucage et al., 1993, Tetrahedron 49:1925; which is herein incorporated by reference in its entirety).

In some embodiments, an oligonucleotide in a complex of the invention comprises one or more cationic tails. In further embodiments, the oligonucleotide is conjugated with at least 1, 2, 3, 4 or more positively-charged amino acids such as, lysine or arginine. In specific embodiments, the oligonucleotide is a PNA and one or more lysine or arginine residues are conjugated to the C-terminal end of the molecule. In a further preferred embodiment, the oligonucleotide is a PNA and comprises from 1 to 4 lysine and/or arginine residues are conjugated to each PNA linkage.

In one embodiment such modified oligonucleotides are prepared by covalently attaching conjugate groups to functional groups such as hydroxyl or amino groups. Useful conjugate groups include, but are not limited to, intercalators, reporter molecules, polyamines, polyamides, polyethylene glycols, polyethers, and groups that enhance the pharmacodynamic or pharmacokinetic properties of the oligonucleotides. Typical conjugate groups include cholesterols, carbohydrates, biotin, phenazine, folate, phenanthridine and anthraquinone. Representative conjugate groups are disclosed in WO/1993/007883 and U.S. Pat. No. 6,287,860, each of which is herein incorporated by reference in its entirety.

Conjugate groups can be attached to various positions of an oligonucleotide directly or via an optional linking group. The term linking group is intended to include all groups amenable to attachment of a conjugate group to an oligomeric compound. Linking groups are bivalent groups useful for attachment of chemical functional groups, conjugate groups, reporter groups and other groups to selective sites in a parent compound such as for example an oligomeric compound. In general a bifunctional linking moiety comprises a hydrocarbyl moiety having two functional groups.

One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in bifunctional linking moieties include., but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl. Further representative linking groups are disclosed for example in WO 94/01550 and WO 94/01550.

Representative United States patents that teach the preparation of such oligonucleotide conjugates include, but are not limited to, U.S. Pat. Nos. 4,828,979; 4,948,882; 5,109,124; 5,118,802; 5,218,105; 5,414,077; 5,486,603; 5,525,465; 5,541,313; 5,545,730; 5,552,538; 5,578,717; 5,580,731; 5,580,731; 5,591,584; 5,512,439; 5,578,718; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928, 5,688,941 and 6,114,513, and U.S. Publ. Nos. 2012/0095075; 2012/0101148; and 2012/0128760, the entire contents of each of which is herein incorporated by reference in its entirety.

In additional related embodiments, the present invention includes HES-oligonucleotide complexes and/or pharmaceutical compositions containing HES-oligonucleotide complexes that further comprise one or more active agents or therapeutic agents. In one embodiment the active agent or therapeutic agent is a nucleic acid. In various embodiments, the nucleic acid is a plasmid, an immunostimulatory oligonucleotide, a siRNA, a shRNA, a miRNA, ail anti-iniRNA, a dicer substrate, a decoy, an aptamer, an antisense oligonucleotide, or a ribozyme.

Oligonucleotide Synthesis

Oligonucleotides and phosphoramidites can be synthesized and/or modified by methods well established in the art. Oligomerization of modified and unmodified nucleosides is performed according to literature procedures for DNA-like compounds (Protocols for Oligonucleotides and Analogs, Ed. Agrawal (1993), Humana Press) and/or RNA-like compounds (Scaringe, Methods (2001), 23, 206-217. Gait et al., Applications of Chemically synthesized RNA in RNA: Protein Interactions, Ed. Smith (1998), 1-36. Gallo et al., Tetrahedron 57:5707-5713 (2001),) synthesis as appropriate. (see, also, Current Protocols in Nucleic Acid Chemistry, Beaucage, S. L. et al. (Edrs.), John Wiley & Sons, Inc., New York, N.Y., USA, which is herein incorporated herein by reference in its entirety). Oligonucleotides are preferably chemically synthesized using appropriately protected reagents and a commercially available oligonucleotide synthesizer. Suppliers of oligonucleotide synthesis reagents useful in manufacturing the oligonucleotides of the invention include, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Alternatively, oligomers may be purchased from various oligonucleotide synthesis companies such as, for example, Dharmacon Research Inc., (Lafayette, Colo.), Qiagen (Germantown, Md.), Proligo and Ambion.

In certain embodiments, the preparation of oligonucleotides as disclosed herein is performed according to literature procedures for DNA: Protocols for Oligonucleotides and Analogs, Agrawal, Ed., Humana Press, 1993, and/or RNA: Scaringe, Methods, 2001, 23, 206-217; Gait et al., Applications of Chemically synthesized RNA in RNA: Protein Interactions, Smith, Ed., 1998, 1-36; Gallo et al., Tetrahedron, 2001, 57, 5707-5713. Additional methods for solid-phase synthesis may be found U.S. Pat. Nos. 4,415,732; 4,458,066; 4,500,707; 4,668,777; 4,725,677; 4,973,679; and 5,132,418; and Re. 34,069.

Irrespective of the particular protocol used, the oligonucleotides used in accordance with this invention may be conveniently and routinely made through the well-known technique of solid phase synthesis. Equipment for such synthesis is sold by several vendors including, for example, Gene Forge (Redwood City, Calif.). Suitable solid phase techniques, including automated synthesis techniques, are described in Oligonucleotides and Analogues, a Practical Approach, F. Eckstein, Ed., Oxford University Press, New York, 1991. Any other means for such synthesis known in the art may additionally or alternatively be employed (including solution phase synthesis).

The synthesis and preparation of the bicyclic sugar modified monomers adenine, cytosine, guanine, 5-methyl-cytosine, thymine and uracil, along with their oligomerization, and nucleic acid recognition properties have been described (Koshkin et al., Tetrahedron, 54:3607-3630 (1998); WO 98/39352 and WO 99/14226), the contents of each of which is herein incorporated by reference in its entirety. Other bicyclic sugar modified nucleoside analogs such as the 4'-$CH_2$—S-2' analog have also been prepared (Kumar et al., Bioorg. Med. Chem. Lett., 1998, 8, 2219-2222). Preparation of other bicyclic sugar analogs containing oligodeoxyribonucleotide duplexes as substrates for nucleic acid polymerases has also been described (WO 98-DK393 19980914), the contents of each of which is herein incorporated by reference in its entirety Techniques for linking fluorophores to oligonucleotides such as those used according to the methods of the invention are well known in the art and can be used or routinely modified to prepare the HES-oligonucleotides of the invention. See, e.g., Connolly et al., Nucleic Acids Res. 13:4485-4502 (1985); Dreyer et al., Proc. Natl. Acad. Sci. 86:9752-9756 (1989); Nelson et al., Nucleic Acids Res. 17:7187-7194 (1989); Sproat et al., Nucleic Acids Res. 15, 6181-6196 (1987) and Zuckerman et al., Nucleic Acids Res. 15:5305-5321 (1987), the contents of each of which is herein incorporated by reference in its entirety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers.

The derivatization may be by a simple substitution of a group on the fluorophore itself, or may be by conjugation to a linker.

Fluorophores are optionally attached to the 5' and/or 3' terminal backbone phosphates and/or other bases of the oligonucleotide via a linker. Various suitable linkers are known to those of skill in the art and/or are discussed below. In some embodiments, the linker is a flexible aliphatic linker. In additional embodiments, the linker is a C1 to C30 linear or branched, saturated or unsaturated hydrocarbon chain. In some embodiments, the linker is a C2 to C6 linear or branched, saturated or unsaturated hydrocarbon chain. In additional embodiments the hydrocarbon chain linker is substituted by one or more heteroatoms, aryls; or lower alkyls, hydroxylalkyls or alkoxys.

In some embodiments, one or more fluorophores are incorporated into an oligonucleotide during automated synthesis using one or more fluoropophore-modified nucleosides, fluorophore and sugar/base/and/or linkage modified nucleosides, and/or deoxynucleoside phosphoramidites.

In some embodiments, one or more fluorophores are incorporated into an oligonucleotide in a post-synthesis labeling reaction. Appropriate post-synthesis labeling reactions are known in the art and can routinely be applied or modified to synthesize the HES-oligonucleotides of the invention. In one embodiment, one or more fluorophores are incorporated into an oligonucleotide in a post-synthesis labeling reaction in which an amine- or thiol-modified nucleotide or deoxynucleotide in the synthesized oligonucleotide is reacted with an amine- or thiol-reactive fluorophore such as, a succinimidyl ester fluorophore.

In further embodiments, one or more of the same fluorophores are integrated into the oligonucleotide in a single reaction that involves contacting a reactive form of the dye with an oligonucleotide containing a desired number of reactive groups capable of reacting with the fluorpohore in a suitable buffer under conditions and for an amount of time sufficient to accomplish the integration of the fluorphores into the oligonucleotide. The reactive groups can routinely be incorporated into the oligonucleotide during synthesis using standard techniques and reagents known in the art.

Formulations:

The HES-oligonucleotide complexes are optionally admixed with a suitable pharmaceutically acceptable diluent or carrier pharmaceutically acceptable active or inert substance for the preparation of pharmaceutical compositions. Thus, the invention also encompasses pharmaceutical compositions that include HES-oligonucleotide complexes. Compositions and methods for the formulation of pharmaceutical compositions are dependent upon a number of criteria, including, but not limited to, route of administration, extent of disease, or dose to be administered. Such considerations are well understood by those skilled in the art.

Subject doses of the HES-oligonucleotides for mucosal or local delivery typically range from about 0.1 ug to 50 mg per administration (e.g., in the case of exon skipping drugs such as AVI-4658 (morpholino) wherein trial doses include the administration of the drug at 30 mg/kg and 50 mg/kg wk IV) which depending on the application could be given daily, weekly, or monthly and any other amount of time there between. However, dosing may be at substantially higher or lower ranges. Determination of appropriate dosing ranges and frequency is well within the ability of those skilled in the art. The administration of a given dose can be carried out both by single administration in the form of an individual dose unit or else several smaller dose units.

Pharmaceutical compositions comprising HES-oligonucleotide complexes encompass any pharmaceutically acceptable salts, esters, or salts of such esters, or any other oligonucleotide which, upon administration to a subject such as a mouse, rat, rabbit or human, is capable of providing (directly or indirectly) the biologically active metabolite or residue thereof. Accordingly, for example, the disclosure is also drawn to physiologically and pharmaceutically acceptable salts (i.e., salts that retain the desired biological activity of the parent compound and do not impart undesired toxicological effects thereto) of HES-oligonucleotide complexes, prodrugs, physiologically and pharmaceutically acceptable salts of such prodrugs, and other bioequivalents. Suitable pharmaceutically acceptable salts include, but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Prodrugs include for example, the incorporation of additional nucleosides at one or both ends of an oligonucleotide which are cleaved by endogenous nucleases within the body, to form the active oligonucleotide.

In some embodiments, prodrug versions of the oligonucleotides of the invention are prepared as SATE [(S-acetyl-2-thioethyl)phosphate]derivatives according to the methods disclosed in WO 93/24510 and WO 94/26764.

In the context of the present invention, a pharmaceutically acceptable diluent includes phosphate-buffered saline (PBS). PBS is a diluent suitable for use in compositions to be Pharmaceutical compositions of the invention include, but are not limited to, solutions and formulations. These compositions may be generated from a variety of components that include, but are not limited to, preformed liquids.

The pharmaceutical compositions can conveniently be presented in unit dosage form and can be prepared according to conventional techniques well known in the pharmaceutical industry. Such techniques include the step of bringing into association the active ingredients with the pharmaceutical diluent(s) or carrier(s). In general the formulations are prepared by uniformly and intimately bringing into association the active ingredients with liquid carriers or finely divided solid carriers or both, and then, if necessary, shaping the product.

The pharmaceutical compositions can be formulated into any of many possible dosage forms including, but not limited to, tablets, capsules, liquid syrups, soft gels, suppositories, and enemas. The compositions can also be formulated as suspensions in aqueous or mixed media. Aqueous suspensions can further contain substances which increase the viscosity of the suspension including, for example, sodium carboxymethylcellulose, sorbitol and/or dextran. The suspension may additionally contain one or more stabilizers.

As used herein, the term "dose" refers to a specified quantity of a pharmaceutical agent provided in a single administration. In certain embodiments, a dose may be administered in one or more boluses, tablets, or injections.

For example, in certain embodiments, where subcutaneous administration is desired and the desired dose requires a volume not easily accommodated by a single injection, then two or more injections may be used to achieve the desired dose. In certain embodiments, a dose may be administered in two or more injections to minimize injection site reaction in an individual.

Administration

The present invention also includes pharmaceutical compositions and formulations which include the HES-oligonucleotide complexes of the invention. The methods of the invention can be practiced using any mode of administration that is medically acceptable, meaning any mode that produces a therapeutic effect without causing clinically unacceptable adverse effects (i.e., where undesired effects are to such an extent so as to prohibit administration of the HES-oligonucleotide complex). The pharmaceutical compositions of, the present invention may be administered in a number of ways depending upon whether local or systemic treatment is desired and upon the area to be treated. Thus, for use in therapy, an effective amount of the HES-oligonucleotide can be administered to a subject by any mode that delivers the nucleic acid to the desired surface, e.g., mucosal or systemic. Suitable routes of administration include, but are not limited, to topical oral, pulmonary, parenteral, intranasal, intratracheal, inhalation, ocular, vaginal, and rectal. Such formulations and their preparation are well known by those skilled in the art, as are considerations for optimal dosing routes Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), peroral or parenteral. Parenteral administration includes intravenous, intraarterial, subcutaneous, intraperitoneal or intramuscular injection or infusion; or intracranial, e.g., intrathecal or intraventricular, administration. HES-oligonucleotides with at least one 2'-O-methoxyethyl modification, including chimeric molecules or molecules which may have a 2'-O-methoxyethyl modification of every nucleotide sugar, are believed to be particularly useful for oral administration. Pharmaceutical compositions and formulations for topical administration may include transdermal patches, drops, suppositories, sprays, liquids and powders. Conventional pharmaceutical carriers, aqueous, powder or and the like may be necessary or desirable.

Compositions and formulations for oral administration include powders or granules, suspensions or solutions in water, capsules, sachets or tablets.

Compositions and formulations for parenteral, intrathecal or intraventricular administration may include sterile aqueous solutions which may also contain buffers, diluents and other suitable additives and pharmaceutically acceptable carriers or excipients known in the art.

In certain embodiments, parenteral administration is by infusion. Infusion can be chronic or continuous or short or intermittent. In certain embodiments, infused pharmaceutical agents are delivered via cannulae or catheters, in certain embodiments, infused pharmaceutical agents are delivered with a pump. In certain embodiments, the compounds and compositions as described herein are administered parenterally. In additional embodiments, parenteral administration is by injection. The injection can be delivered with a syringe or a pump. In certain embodiments, the injection is a bolus injection. In certain embodiments, the injection is administered directly to a tissue or organ. In additional embodiments, the parenteral administration comprises subcutaneous or intravenous administration.

In some embodiments, an HES-oligonucleotide complex can be administered to a subject via an oral route of administration. The subject may be a mammal, such as a mouse, a rat, a dog, a guinea pig, or a non-human primate. In some embodiments, the subject may be a human subject. In certain embodiments, the subject may be in need of modulation of the level or expression of one or more pri-miRNAs as discussed in more detail herein. In some embodiments, compositions for administration to a subject In the context of the present invention, a preferred means for delivery of an HES-oligonucleotide complex employs an infusion pump such as Medtronic SyncroMed® II pump.

The antisense oligonucleotides of the invention can be utilized for diagnostics, therapeutics, prophylaxis and as research reagents and kits. For therapeutics, a subject such as a mouse, rabbit or primate, preferably a human, suspected of having a disease or disorder which can be treated by modulating the behavior of a cell can be treated by administering an HES-oligonucleotide complex of the invention.

In some embodiments, the HES-oligonucleotide delivery system of the invention is combined with one or more additional oligonucleotide delivery systems to further facilitate HES-oligonucleotide complex delivery into a cell and/or targeted delivery of the oligonucleotide. Marcromolecular delivery systems that can be combined with the HES-oligonucleotide delivery system include, but are not limited to the use of dendrimers, biodegradable polymers. Additional, delivery systems that can be combined with the HES-oligonucleotide delivery system include, but are not limited to, conjugates with amino acids, sugars, or targeting nucleic acid motifs. In particular embodiments, an HES-oligonucleotide complex is conjugated with an aptamer, peptide, or antibody (or antibody fragment) that specifically hybridizes to a certain receptor or serum protein, which modulates the half-life of the complex, or which facilitates the uptake of the complex.

The HES-oligonucleotide delivery system can also be covalently attached to cholesterol molecules.

The HES-oligonucleotide complexes of the invention may be admixed, conjugated or otherwise associated with other molecules, molecule structures or mixtures of compounds, as for example, receptor targeted molecules, oral, rectal, topical or other formulations.

Exemplary Modes of Action

Antisense

In some embodiments, an oligonucleotide in an HES-oligonucleotide complex is an antisense oligonucleotide. The term "antisense oligonucleotide" or simply "antisense" is meant to include oligonucleotides corresponding to single strands of nucleic acids (e.g., DNA, RNA and nucleic acid mimetics such as PNAs morpholinos (e.g., PMOs), and compositions containing modified nucleosides and/or internucleoside linkages) that bind to their cognate mRNA in the cells of the treated subject and modulate RNA function by for example, altering the translocation of target RNA to the site of protein translation, translation of protein from the target RNA, altering splicing of the target RNA (e.g., promoting exon skipping) and altering catalytic activity which may be engaged in or facilitated by the target RNA, and targeting the mRNA for degradation by endogenous RNase H. In some embodiments, the antisense oligonucleotides alter cellular activity by hybridizing specifically with chromosomal DNA. The term antisense oligonucleotide also encompasses antisense oligonucleotides that may not be exactly complementary to the desired target gene. Thus, the invention can be utilized in instances where noxi-target specific-activities are found with antisense, or where an antisense sequence containing one or more mismatches with the target sequence is preferred for a particular use. The overall effect of such interference with target nucleic acid function is modulation of a targeted protein of interest. In the context of the present invention, "modulation" means either an increase (Stimulation) or a decrease (inhibition) in the expression of a gene or protein in the amount, or levels, of a small non-coding RNA, nucleic acid target, an RNA or protein associated with a small non-coding RNA, or a downstream target of the small non-coding RNA (e.g., a mRNA representing a protein-coding nucleic acid that is regulated by a small non-cooling RNA). Inhibition is a suitable form of modulation and small non-coding RNA is a suitable nucleic acid target. Small non-coding RNAs whose levels can be modulated include miRNA and miRNA precursors. In the context of the present disclosure, "modulation of function" means an alteration in the function or activity of the small non-coding RNA or an alteration in the function of any cellular component with which the small non-coding RNA has an association or downstream effect. In one embodiment, modulation of function is an inhibition of the activity of a small non-coding RNA.

Antisense oligonucleotides are preferably from about 8 to about 80 contiguous linked nucleosides in length. In some embodiments, the antisense oligonucleotides are from about 10 to about 50 nucleosides or from about 13 to about 30 nucleotides. Antisense oligonucleotides of the invention include ribozymes, antimiRNAs, external guide sequence (EGS) oligonucleotides (oligozymes), and other short catalytic RNAs or catalytic oligonucleotides which specifically hybridize to the target nucleic acid and modulate its expression.

The antisense oligonucleotides in accordance with this invention comprise from about 15 to about 30 nucleosides in length, (i.e., from 15 to 30 linked nucleosides) or alternatively, from about 17 to about 25 nucleosides in length. In particular embodiments, an antisense oligonucleotide is 8, 9, 10, 11, 12, 13, 14, 15, 16, 17, 18, 19, 20, 21, 22, 23, 24, 25, 26, 27, 28, 29, or 30 nucleosides in length. In additional embodiments, an antisense oligonucleotide is from about 10 to about 50 nucleotides, more preferably about 15 to about 30 nucleotides.

In additional embodiments, an oligonucleotide in a complex of the invention interferes with the transcription of a target RNA of interest. In some embodiments, the oligonucleotide interferes with transcription of an mRNA or miRNA of interest by strand displacement. In other embodiments, the oligonucleotide interferes with the transcription of an mRNA by forming a stable complex with a portion of a targeted gene by strand invasion or triplex formation (triplex forming oligonucleotides (THOs), such as those containing LNAs see, e.g., U.S. Appl. Publ. No. 2012/0122104, herein incorporated by reference in its entirety). In additional embodiments, the HES-oligonucleotides of the invention interfere with the transcription of a target RNA (e.g., mRNA or miRNA) by interfering with the transcription apparatus of the cell. In some embodiments, the HES-oligonucleotides are designed to specifically bind a region in the 5' end of an mRNA or the AUG start codon (e.g., within 30 nucleotides of the AUG start codon) and to reduce translation. In some embodiments, the HES-oligonucleotides are designed to specifically hybridize to an intron/exon junction in an RNA. In some embodiments, the HES-oligonucleotides are designed to specifically bind the 3' untranslated target sequence in an RNA (e.g., mRNA). In further embodiments, the HES-oligonucleotides are designed to specifically bind nucleotides 1-10 of a miRNA. In additional embodiments, the HES-oligonucleotides are designed to specifically bind a sequence in a precursor-miRNA (pre-miRNA) or primary-miRNA (pri-miRNA) that when bound by the oligonucleotide blocks miRNA processing.

In other embodiments, the HES-oligonucleotides target sites of critical RNA secondary structure or act as steric blockers that cause truncation of the translated polypeptide. In some embodiments, the HES-oligonucleotides (e.g., PNAs and PMOs) are designed to interfere with intron excision, by for example, binding at or near a splice junction of the targeted mRNA. In some embodiments, the HES-oligonucleotide are designed to interfere with intron excision or to increase the expression of an alternative splice variant.

RNase H is an endogenous enzyme that specifically cleaves the RNA moiety of an RNA:DNA duplex. In some embodiments, the antisense oligonucleotides elicit RNase H activity when bound to a target nucleic acid. In some embodiments, the oligonucleotides are DNA or nucleic acid mimetics. HES-oligonucleotides that elicit RNase H activity have particular advantages in for example, harnessing endogenous ribonucleases to reduces targeted RNA.

One antisense design for eliciting RNase H activity is the gapmer motif design in which a chimeric oligonucleotide with a central block composed of DNA, either with or without phosphorothioate modifications, and nuclease resistant 5' and 3' flanking blocks, usually 2'-O-methyl RNA but a wide range of 2' modifications have been used (see Crooke, 2004). Other gapmer designs are described herein or otherwise known in the art.

In additional embodiments, antisense oligonucleotides in the complexes of the invention are designed to avoid activation of RNase H in a cell. Oligonucleotides that do not elicit RNase H activity have particular advantages in for example, blocking transcriptional machinery (via a steric block mechanism) and altering splicing of the target RNA. In some embodiments, the oligonucleotides are designed to interfere with and/or alter intron excision, by for example, binding at or near a splice junction of the targeted mRNA. In additional embodiments, the oligonucleotides are designed to increase the expression of an alternative splice variant of a message. In one preferred embodiment, the antisense oligonucleotide of the invention is a morpholino (e.g., PMO). In another preferred embodiment, the antisense oligonucleotide of the invention is a PNA.

In particular embodiments, the antisense oligonucleotide is targeted to at least a portion of a region up to 50 nucleobases upstream of an intron/exon junction of a target mRNA. More preferably the antisense oligonucleotide is targeted to at least a portion of a region 20-24 or 30-50 nucleobases upstream of an intron/exon junction of a target mRNA and which preferably does not support RNAse H cleavage of the mRNA target upon binding. Preferably, the antisense compound contains at least one modification which increases binding affinity for the RNA target (e.g., mRNA and miRNA) and which increases nuclease resistance of the antisense compound.

In one embodiment, the antisense oligonucleotide comprises at least one nucleoside having a 2' modification of its sugar moiety. In a further embodiment, the antisense oligonucleotide comprises at least 2, 3, 4, 5, 6, 7, 8, 9, 10, 15, or 20 nucleoside having a 2' modification of its sugar moiety. In yet a further embodiment, every nucleoside of the antisense oligonucleotide has a 2' modification of its sugar moiety. Preferably, the 2' modification is 2'-fluoro, 2'-OME, 2'-methoxyethyl (2'-MOE) or a locked nucleic acid (LNA). In some embodiments, the modified nucleoside motif is an LNA or alpha LNA in which a methylene (—CH2-)$_n$ group bridges the 2' oxygen atom and the 4' carbon atom wherein n is 1 or 2. In further embodiments, the LNA or alpha LNA contains a methyl group at the 5' position. In some embodiments, the oligonucleotide contains a 2' modification and at least one internucleoside linkage. In particular embodiment, antisense oligonucleotide contains at least one phosphorothioate internucleoside linkage. In one embodiment, the internucleoside linkages of the oligonucleotide alternate between phosphodiester and phosphorothioate backbone linkages. In another embodiment, every internucleoside linkage of the oligonucleotide is a phosphorothioate linkages.

In additional preferred embodiments, the antisense oligonucleotide in the complexes of the invention comprises at least one 3'-methylene phosphonate, linkage, LNA, peptide nucleic acid (PNA) linkage or phosphorodiamidate morpholino linkage. In further embodiments, the antisense oligonucleotide contains at least one modified nucleobase. Preferably, the modified nucleobase is a C-5 propyne or 5-methyl C.

The antisense oligonucleotide compounds of the invention can routinely be synthesized using techniques known in the art.

RNAi—Post Transcriptional Gene Silencing

Short double-stranded RNA molecules and short hairpin RNAs (shRNAs), i.e. fold-back stem-loop structures that give rise to siRNA can induce RNA interference (RNAi). In some embodiments, an oligonucleotide in an HES-oligonucleotide complex of the invention induces RNAi. RNAi oligonucleotides in the complexes of the invention include, but are not limited to siRNAs, shRNAs and dsRNA DROSHA and/or Dicer substrates. The siRNAs, shRNAs, and one or both strands of the dsRNAs preferably contain one or more modified internucleoside linkages, modified sugar moieties and/or modified nucleobases described herein or otherwise known in the art. These RNAi oligonucleotides have applications including, but not limited to, disrupting the expression of a gene(s) or polynucleotide(s) of interest in a subject. Thus, in some embodiments, the oligonucleotides in the complexes of the invention are used to specifically inhibit the expression of target nucleic acid. In some embodiments, double-stranded RNA-mediated suppression of gene and/or nucleic acid expression is accomplished by administering a complex of the invention comprising a dsRNA DROSHA substrate, dsRNA Dicer substrate, siRNA or shRNA to a subject and/or cell. Double-stranded RNA-mediated suppression of gene and nucleic acid expression may be accomplished according to the invention by administering dsRNA, siRNA or shRNA into a subject. SiRNA may be double-stranded RNA, or a hybrid molecule comprising both RNA and DNA, e.g., one RNA strand and one DNA strand.

siRNAs of the invention are RNA:RNA hybrid, DNA sense:RNA antisense hybrids, RNA sense: DNA antisense hybrids, and DNA:DNA hybrid duplexes normally 21-30 nucleotides long that can associate with a cytoplasmic multi-protein complex known as RNAi-induced silencing complex (RISC). RISC loaded with siRNA mediates the degradation of homologous mRNA transcripts. The invention includes the use of RNAi molecules comprising any of these different types of double-stranded molecules. In addition, it is understood that RNAi molecules may be used and introduced to cells in a variety of forms. Accordingly, as used herein, RNAi molecules encompass any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

In some embodiments, dsRNA oligonucleotide contained in a complex of the invention is double-stranded and 16-30 or 18-25 nucleotides in length. In particular embodiments, the dsRNA is 21 nucleotides in length. In certain embodiments, the dsRNA 0-7 nucleotide 3' overhangs or 0-4 nucleotide 5' overhangs. In particular embodiments, the dsRNA has a two nucleotide 3' overhang. In a further embodiment, the dsRNA contains two complementary RNA strands of 21 nucleotides in length with two nucleotide 3' overhangs (i.e., contains a 19 nucleotide complementary region between the sense and antisense strands). In certain embodiments, the overhangs are UU or dTdT 3' overhangs.

In some embodiments, an siRNA oligonucleotide in a complex of the invention is completely complementary to the corresponding reverse complementary strand of a target RNA. In other embodiments, the siRNA contains 1 or 2 substitutions, deletions or insertions compared to the corresponding reverse complementary strand of a target RNA.

In additional embodiments, the complexes of the invention comprise an RNAi oligonucleotide that is a short hairpin RNA. shRNA is a form of hairpin RNA containing a fold-back stem-loop structure that give rise to siRNA and is thus, likewise capable of sequence-specifically reducing expression of a target gene. Short hairpin RNAs are generally more stable and less susceptible to degradation in the cellular environment than siRNAs. The stem loop structure of ShRNAs can vary in stem length, typically from 19 to 29 nucleotides in length. In certain embodiments, the complexes of the invention comprise an shRNA having a stem that is 19 to 21 or 27 to 29 nucleotides in length. In additional embodiments, the shRNA has a loop size of between 4 to 30 nucleotides in length. While complete complementarity between the portion of the stem that specifically hybridizes to the target mRNA (antisense strand) and the mRNA is preferred, the shRNA may optionally contain mismatches between the two strands of the shRNA hairpin stem. For example, in some embodiments, the shRNA includes one or several G-U pairings in the hairpin stem to stabilize hairpins during propagation in bacteria.

In one embodiment, the nucleic acid target of an RNAi oligonucleotide contained in a complex of the invention is selected by scanning the target RNA (e.g., mRNA or miRNA) for the occurrence of AA dinucleotide sequences. Each AA dinucleotide sequence in combination with the 3' adjacent approximately 19 nucleotides are potential siRNA target sites based off of which an RNAi oligonucleotide can routinely be designed. In some embodiments, the RNAi oligonucleotide target site is not located within the 5' and 3' untranslated regions (UTRs) or regions near the start codon (e.g., within approximately 75 bases of the start codon) of the target RNA in order to avoid potential interference of the binding of the siRNP endonuclease complex by proteins that bind regulatory regions of the target RNA.

RNAi oligonucleotide targeting specific polynucleotides can be readily prepared using or routinely modifying reagents and procedures known in the art. Structural characteristics of effective siRNA molecules have been identified. Elshabir et al. (2001) Nature 411:494-498 and Elshabir et al. (2001), EMBO 20:6877-6888. Accordingly, one of skill in the art would understand that a wide variety of different siRNA molecules may be used to target a specific gene or transcript.

Enzymatic Nucleic Acids

In some embodiments, the complexes of the invention comprise an enzymatic oligonucleotide. Two preferred features of enzymatic oligonucleotides used according to the invention are that they have a specific substrate binding site which is complementary to one or more of the target gene DNA or RNA regions, and that they have nucleotide sequences within or surrounding the substrate binding site which impart an RNA cleaving activity to the oligonucleotide. In some embodiments, the enzymatic oligonucleotide is a ribozyme. Ribozymes are RNA-protein complexes having specific catalytic domains that possess endonuclease activity. Exemplary ribozyme HES-oligonucleotides of the invention are formed in a hammerhead, hairpin, a hepatitis delta virus, group I intron or RNaseP RNA (in association with an RNA guide sequence) or a Neurospora VS RNA motif.

While the enzymatic oligonucleotides in the complexes of the invention may contain modified nucleotides described herein or otherwise known in the art, it is important that such modifications do not lead to conformational changes that abolish catalytic activity of the enzymatic oligonucleotide. Methods of designing, producing, testing and optimizing enzymatic oligonucleotides such as, ribozymes are known in the art and are encompassed by the invention (see, e.g., WO 91/03162; WO 92/07065; WO 93/15187; WO 93/23569; WO 94/02595, WO 94/13688; EP 92110298; and U.S. Pat. No. 5,334,711, each of which is herein incorporated by reference in its entirety).

Aptamers and Decoys

In some embodiments, the HES-oligonucleotides of the invention contain an aptamer and/or a decoy. As used herein, aptamers refer to a single-stranded nucleic acid molecule (such as DNA or RNA) that assumes a specific, sequence-dependent shape and specifically hybridizes to a target protein with high affinity and specificity. Aptamers in the compositions of the invention are generally fewer than 100 nucleotides, fewer than 75 nucleotides, or fewer than 50 nucleotides in length. The term "aptamer" as used herein, encompasses mirror-image aptamer(s) (high-affinity L-enantiomeric nucleic acids such as, L-ribose or L-2'-deoxyribose units) that confer resistance to enzymatic degradation compared to D-oligonucleotides. Methods for making and identifying aptamers are known in the art and can routinely be modified to identify aptamers having desirable diagnostic and/or therapeutic properties and to incorporate these aptamers into the HES-oligonucleotides of the invention. See, e.g., Wlotzka et al., Proc. Natl. Acad. Sci. 99(13): 8898-8902, 2002, which is herein incorporated by reference in its entirety.

As used herein, the term "decoy" refers to short double-stranded nucleic acids (including single-stranded nucleic acids designed to "fold back" on themselves) that mimic a site on a nucleic acid to which a factor, such as a protein, binds. Such decoys competitively inhibit and thereby decrease the activity and/or function Gf the factor. Methods for making and identifying decoys are known in the art and can routinely be modified to identify decoys having desirable diagnostic and/or therapeutic properties, and to incorporate these decoys into the HES-oligonucleotides of the invention. See, e.g., U.S. Pat. No. 5,716,780 to Edwards et al, which is herein incorporated by reference in its entirety.

Small Non-Coding RNA and Antagonists (e.g., miRNAs, and Anti-miRNAs

There is a need for agents that regulate gene expression via the mechanisms mediated by small non-coding RNAs. The present invention meets this and other needs.

As used herein, the term "small non-coding RNA" is used to encompass, without limitation, a polynucleotide molecule ranging from 17 to 29 nucleotides in length. In one embodiment, a small non-coding RNA is a miRNA (also known as miRNAs, Mirs, miRs, mirs, and mature miRNAs).

MicroRNAs (miRNAs), also known as "mature" miRNA") are small (approximately 21-24 nucleotides in length), non-coding RNA molecules that have been identified as key regulators of development, cell proliferation, apoptosis and differentiation. Examples of particular developmental processes in which miRNAs participate include stem cell differentiation, neurogenesis, angiogenesis, hematopoiesis, and exocytosis (reviewed by Alvarez-Garcia and Miska, Development, 2005, 132, 4653-4662). miRNA have been found to be aberrantly expressed in disease states, i.e., specific miRNAs are present at higher or lower levels in a diseased cell or tissue as compared to healthy cell or tissue.

miRNAs are believed to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670). One mechanism by which miRNAs regulate gene expression is through binding to the 3'-untranslated regions (3'-UTR) of specific mRNAs. miRNAs nucleotide (nt) RNA molecules that become incorporated into the RNA-induced silencing complex (RISC) mediate down-regulation of gene expression through translational inhibition, transcript cleavage, or both. RISC is also implicated in transcriptional silencing in the nucleus of a wide range of eukaryotes.

The present invention provides, inter alia, compositions and methods for modulating small non-coding RNA activity, including miRNA activity associated with disease states. Certain compositions of the invention are particularly suited for use in in vivo methods due to their improved delivery, potent activity and/or improved therapeutic index.

The invention provides compositions and methods for modulating small non-coding RNAs, including miRNA. In particular embodiments, the invention provides compositions and methods for modulating the levels, expression, processing or function of one or a plurality of small non-coding RNAs, such as miRNAs. Thus, in some embodiments, the invention encompasses compositions, such as pharmaceutical compositions, comprising an HES-oligonucleotide complex having at least one oligonucleotide specifically hybridizable with a small noncoding RNA, such as a miRNA.

In some embodiments, an oligonucleotide in an HES-oligonucleotide complex of the invention specifically hybridizes with or sterically interferes with nucleic acid molecules comprising or encoding one or more small non-coding RNAs, such as, miRNAs. In particular embodiments, the invention provides HES-oligonucleotide complexes and methods useful for modulating the levels, activity, or function of miRNAs, including those relying on antisense mechanisms and those that are independent of antisense mechanisms.

As used herein, the terms "target nucleic acid," "target RNA," "target RNA transcript" or "nucleic acid target" are used to encompass any nucleic acid capable of being targeted including, without limitation, RNA. In a one embodiment, the target nucleic acids are non-coding sequences including, but not limited to, miRNAs and miRNA precursors. In a preferred embodiment, the target nucleic acid is a miRNA, which may also be referred to as the miRNA. An oligonucleotide is "targeted to a miRNA" when an oligonucleotide comprises a sequence substantially, including 100% complementary to a miRNA.

As used herein, oligonucleotides are "substantially complementary" to for example, an RNA such as a small non-coding RNA, when they are capable of specifically hybridizing to the small non-coding RNA under physiologic conditions. In some embodiments, an oligonucleotide is "targeted to a miRNA" when an oligonucleotide comprises a sequence substantially, including 100% complementary to at least 8 contiguous nucleotides of a miRNA. In some embodiments, an oligonucleotide in a complex of the invention specifically hybridizes to an miRNA and ranges in length from about 8 to about 21 nucleotides, from about 8 to about 18 nucleotides, or from about 8 to about 14 nucleotides. In additional embodiments, the oligonucleotide specifically hybridizes to an miRNA and ranges in length from about 12 to about 21 nucleotides, from about 12 to about 18 nucleotides, or from about 12 to about 14 nucleotides. In particular embodiments, the oligonucleotides are 8, 9, 10, 11, 12, 13, 14, 15, 16, 17, 18, 19, 20 or 21 monomer subunits (nucleotides) in length. In certain embodiments, oligonucleotides, the oligonucleotides are 14, 15, 16, 17 or 18 monomer subunits (nucleotides) in length.

In particular embodiments, the oligonucleotide has full length complementarity to the miRNA, In other embodiments, the length complementarily between the oligonucleotide and the target nucleic acid as well as up to 3 "mismatches" between the oligonucleotide and the target miRNA such that the oligonucleotide is still capable of hybridizing with the target miRNA and the function of the oligonucleotide is not substantially impaired. In other embodiments, the oligonucleotide contains a truncation or expansion with respect to the length of target miRNA by up to 6 nucleosides, at either the 3' or 5' end, or at both the 3' and 5' end of the oligonucleotide. In certain embodiments, the oligonucleotide is truncated by 1 or 2 nucleosides compared with the length of the target miRNA. As a non-limiting example, if the target miRNA is 22 nucleotides in length, the oligonucleotide which has essentially full length complementarity may be 20 or 21 nucleotides in length. In a particular embodiment, the oligonucleotide is truncated by 1 nucleotide on either the 3' or 5' end compared to the miRNA.

In some embodiments, the invention provides a method of modulating a small non-coding RNA comprising contacting a cell with an HES-oligonucleotide complex, wherein an oligonucleotide of the HES-oligonucleotide complex comprises a sequence substantially complementary to the small non-coding RNA, a small non-coding RNA precursor (e.g., a miRNA precursor), or a nucleic acid encoding the small non-coding RNA. As used herein, the term "small non-coding RNA precursor miRNA precursor" is used to encompass any longer nucleic acid sequence from which a small (mature) non-coding RNA is derived and may include, without limitation, primary RNA transcripts, pri-small non-coding RNAs, and pre-small non-coding RNAs. For example, an "miRNA precursor" encompasses any longer nucleic acid sequence from which a miRNA is derived and may include, without limitation, primary RNA transcripts, pri-miRNAs, and pre-miRNAs.

The invention provides, inter alia, compositions such as pharmaceutical compositions, containing an HES-oligonucleotide complex containing an oligonucleotide which is targeted to nucleic acids comprising or encoding small a non-coding RNA, and which acts to modulate the levels of the small non-coding RNA, or modulate its function. In further embodiments, the invention provides, a composition such as a pharmaceutical composition, containing an HES-oligonucleotide complex comprising an oligonucleotide which is targeted to a miRNA and which acts to modulate the levels of the miRNA, or interfere with its processing or function.

In some embodiments, the HES-oligonucleotide complex contains an oligonucleotide that specifically hybridizes to nucleotides 1-10 of a miRNA (i.e., the seed region). In additional embodiments, the oligonucleotide specifically hybridizes to a sequence in a precursor-miRNA (pre-miRNA) or primary-miRNA (pri-miRNA) that when bound by the oligonucleotide blocks miRNA processing.

In some embodiments, the composition contains an HES-oligonucleotide complex contains an oligonucleotide which is targeted to nucleic acids comprising or encoding a small non-coding RNA and which acts to reduce the levels of the small non-coding RNA and/or interfere with its function in a cell.

In other embodiments, the composition contains an HES-oligonucleotide complex contains an oligonucleotide which comprises or encodes the small non-coding RNA or increases the endogenous expression, processing or function of the small non-coding RNA (e.g., by binding regulatory sequences in the gene encoding the non-coding RNA) and which acts to increase the level of the small non-coding RNA and/or increase its function in a cell.

Oligonucleotides contained in the HES-oligonucleotides of the invention can modulate the levels, expression or function of small non-coding RNAs by hybridizing to a nucleic acid comprising or encoding a small non-coding RNA nucleic acid target resulting in alteration of normal function. For example, non-limiting mechanisms by which the oligonucleotides might decrease the activity (including levels, expression or function) of a small non-coding RNA include facilitating the destruction of the small non-coding RNA through cleavage, sequestration, steric occlusion and by hybridizing to the small non-coding RNA and preventing it from hybridizing to, and regulating the activity of, its normal cellular target(s).

In an additional embodiment, the invention provides a method of inhibiting the activity of a small non-coding RNA, comprising contacting a cell with an HES-oligonucleotide complex comprising an oligonucleotide which is targeted to nucleic acids comprising or encoding a small non-coding RNA and which acts to reduce the levels of the small non-coding RNA and/or interfere with its function in the cell. In some embodiments, the oligonucleotide comprises a sequence substantially complementary nucleic acids comprising or encoding the non-coding RNA. In particular embodiments, the small non-coding RNA is a miRNA.

In another embodiment, the invention provides a method of inhibiting the activity of a small non-coding RNA, comprising administering to a subject an HES-oligonucleotide complex containing an oligonucleotide which is targeted to nucleic acids comprising or encoding a small non-coding RNA and which acts to reduce the levels of the small non-coding RNA and/or interfere with its function in the subject. In some embodiments, the oligonucleotide comprises a sequence substantially complementary nucleic acids comprising or encoding the non-coding RNA. In particular embodiments, the small non-coding RNA is a miRNA.

In an additional embodiment, the invention provides a method of increasing the activity of a small non-coding RNA, comprising contacting a cell with an HES-oligonucleotide complex containing an oligonucleotide which comprises or encodes the small non-coding RNA or increases the endogenous expression, processing or function of the small non-coding RNA (e.g., by binding regulatory sequences in the gene encoding the non-coding RNA) and which acts to increase the level of the small non-coding RNA and/or increase its function in the cell. In some embodiments, the oligonucleotide comprises a sequence substantially the same as nucleic acids comprising or encoding the non-coding RNA. In some embodiments, the oligonucleotide shares 100% identity with at least 15 contiguous nucleotides, at least 20 contiguous nucleotides or over the full-length of the small non-coding RNA sequence. In particular embodiments, the small non-coding RNA is a miRNA.

In another embodiment, the invention provides a method of increasing the activity of a small non-coding RNA, comprising administering to a subject an HES-oligonucleotide complex containing an oligonucleotide which comprises or encodes the small non-coding RNA or increases the endogenous expression, processing or function of the small non-coding RNA, and which acts to increase the level of the small non-coding RNA and/or increase its function in the subject. In some embodiments, the oligonucleotide comprises a sequence substantially the same as nucleic acids comprising or encoding the non-coding RNA. In some embodiments, the oligonucleotide shares 100% identity with at least 15 contiguous nucleotides, at least 20 contiguous nucleotides or over the tall-length of the small non-coding RNA sequence. In particular embodiments, the small non-coding RNA is a miRNA.

In additional embodiments, the HES-oligonucleotide comprises a sequence substantially the same as nucleic acids comprising or encoding the small non-coding RNA. In some embodiments, the HES-oligonucleotide is a miRNA mimic. In some embodiments the miRNA mimic is double stranded. In further embodiments, the HES-oligonucleotide contains an miRNA mimic that is double stranded and contains oligonucleotides of 18-23 units in length and is blunt ended or comprises one or more 3' overhangs of 1, 2, or 3 nucleotides. In additional embodiments, the HES-oligonucleotide contains a single stranded miRNA mimic that is 18-23 units in length. HES-oligonucleotides containing expression vectors that express these miRNA mimics are also encompassed by the invention. In some embodiments, the oligonucleotide shares 100% identity with at least 15 contiguous nucleotides, at least 20 contiguous nucleotides or over the full-length of the small non-coding RNA sequence. In particular embodiments, the small non-coding RNA is a miRNA.

The invention also encompasses a method of treating a disease or disorder characterized by the overexpression of a small-noncoding RNA in a subject, comprising administering to the subject an HES-oligonucleotide complex, containing an oligonucleotide which is targeted to nucleic acids comprising or encoding the small non-coding RNA and which acts to reduce the levels of the small non-coding RNA and/or interfere with its function in the subject. In some embodiments, the HES-oligonucleotide is an anti-miRNA (anti-miR) In additional embodiments the anti-miRNA is double stranded. In further embodiments, the HES-oligonucleotide contains an anti-miRNA that is double stranded and contains oligonucleotides of 18-23 units in length and is blunt ended or comprises one or more 3' overhangs of 1, 2, or 3 nucleotides. In additional embodiments, the HES-oligonucleotide contains a single stranded anti-miR that is 8-25 units in length. HES-oligonucleotides containing expression vectors that express these anti-MiRs are also encompassed by the invention. In some embodiments, the oligonucleotide comprises a sequence substantially complementary to the overexpressed small-noncoding RNA.

In further embodiments, the invention encompasses a method of treating a disease or disorder characterized by the overexpression of a miRNA in a subject comprising administering to the subject an HES-oligonucleotide complex containing an oligonucleotide which is targeted to nucleic acids comprising or encoding the miRNA and which acts to reduce the levels of the miRNA and/or interfere with its function in the subject. In some embodiments, the oligonucleotide comprises a sequence substantially complementary to the overexpressed miRNA.

a. Families of miRNAs can be characterized by nucleotide identity at positions 2-8 of the miRNA, a region known as the seed sequence. The members of a miRNA family are herein termed "related miRNAs". Each member of a miRNA family shares an identical seed sequence that plays an essential role in miRNA targeting and function. As used herein, the term "seed sequence" or "seed region" refers to nucleotides 2 to 9 from the 5'-end of a mature miRNA sequence. Examples of miRNA families are known in the art and include, but are not limited to, the let-7 family (having 9 miRNAs), the miR-15 family (comprising miR-15a, miR-15b, miR15-16, miR-16-1, and miR-195), and the miR-181 family (comprising miR-181a, miR-181b, and miR-181c). In some embodiments, an HES-oligonucleotide specifically hybridizes to the seed region of a miRNA and interferes with the processing or function of the miRNA. In some embodiments, the HES-oligonucleotide specifically hybridizes to the seed region of a miRNA and interferes with the processing or function of multiple miRNAs. In further embodiments, at least 2 of the multiple miRNAs have related seed sequences or are members of the miRNA superfamily.

The association of miRNA dysfunction with diseases such as cancer, fibrosis, metabolic disorders and inflammatory disorders and the ability of miRNAs to influence an entire network of genes involved in a common cellular process makes the selective modulation of miRNAs using anti-miRNAs and miRNA mimics particularly attractive disease modulating therapeutics. The invention also encompasses a method of treating a disease or disorder characterized by the overexpression of a protein in a subject, comprising administering to the subject an HES-oligonucleotide complex, containing an oligonucleotide which is targeted to nucleic acids comprising or encoding a small non-coding RNA that influences the increased production of the protein, wherein the oligonucleotide act to reduce the levels of the small non-coding RNA and/or interfere with its function in the subject. In some embodiments, the oligonucleotide comprises a sequence substantially complementary to the small-noncoding RNA.

The invention also encompasses a method of treating a disease or disorder characterized by the overexpression of a protein in a subject, comprising administering to the subject an HES-oligonucleotide complex, containing an oligonucleotide which is targeted to nucleic acids comprising or encoding a miRNA that influences the increased production of the protein, wherein the oligonucleotide acts to reduce the levels of the miRNA and/or interfere with its function in the subject. In some embodiments, the oligonucleotide comprises a sequence substantially complementary (specifically hybridizable) to the miRNA.

The invention also encompasses a method of treating a disease or disorder characterized by the under expression of a small-noncoding RNA in a subject, comprising administering to the subject an HES-oligonucleotide complex, containing an oligonucleotide which comprises or encodes the small non-coding RNA or increases the endogenous expression, processing or function of the small non-coding RNA, and which acts to increase the level of the small non-coding RNA and/or increase its function in the subject. In some embodiments, the oligonucleotide comprises a sequence substantially complementary specifically hybridizable) to the overexpressed small-noncoding RNA.

In further embodiments, the invention encompasses a method of treating a disease or disorder characterized by the overexpression of a miRNA in a subject, comprising administering to the subject an HES-oligonucleotide complex, containing an oligonucleotide which comprises or encodes the small non-coding RNA or increases the endogenous expression, processing or function of the small non-coding RNA, and which acts to increase the level of the small non-coding RNA and/or increase its function in the subject. In some embodiments, the oligonucleotide comprises a sequence substantially complementary to the overexpressed miRNA.

The invention also encompasses a method of treating a disease or disorder characterized by the overexpression of a protein in a subject, comprising administering to the subject an HES-oligonucleotide complex, containing an oligonucleotide which comprises or encodes the small non-coding RNA or increases the endogenous expression, processing or function of the small non-coding RNA, and which acts to increase the level of the small non-coding RNA and/or increase its function in the subject. In some embodiments, the oligonucleotide comprises a sequence substantially complementary to the small-noncoding RNA.

The invention also encompasses a method of treating a disease or disorder characterized by the overexpression of a protein in a subject, comprising administering to the subject an HES-oligonucleotide complex, containing an oligonucleotide which comprises or encodes the small non-coding RNA or increases the endogenous expression, processing or function of the small non-coding RNA, and which acts to increase the level of the small non-coding RNA and/or increase its function in the subject. In some embodiments, the oligonucleotide comprises a sequence substantially complementary (specifically hybridizable) to the miRNA.

In another embodiment, the invention provides a method of inhibiting miRNA activity comprising administering to subject an HES-oligonucleotide complex having anti-miRNA activity, such as those described herein.

In some embodiments, the HES-oligonucleotide complex contains an oligonucleotide selected from: a siRNA, a miRNA, a dicer substrate (e.g., dsRNA), a ribozyme, a decoy, an aptamer, an antisense oligonucleotide and a plasmid capable of expressing an siRNA, a miRNA, or an antisense oligonucleotide.

In some embodiments, the oligonucleotides are chimeric oligonucleotides comprising an internal region containing at least 1, at least 2, at least 3, at least 4, at least 5, or all 2'-F modified nucleotides and external regions comprising at least one stability enhancing modifications. In one embodiment, an oligonucleotide in the HES-oligonucleotide complex comprises an internal region having a first 2'-modified nucleotide and external regions each comprising a second 2'-modified nucleotide. In a further embodiment, the gap region comprises one or more 2'-fluoro modifications and the wing regions comprise one or more 2'-methoxyethyl modifications. In one embodiment, the oligonucleotide in the HES-oligonucleotide complex is ISIS 393206 or ISIS 327985.

Therapeutic
Diagnostics, Drug Discovery and Therapeutics

The oligonucleotides, complexes and other compositions of the invention have uses that include, but are not limited to, research, drug discovery, kits and diagnostics, and therapeutics. The complexes of the invention are particularly suited for use in in vivo methods due to their improved oligonucleotide delivery over conventional delivery techniques.

The invention provides compositions and methods for detecting a nucleic acid sequence in vitro or in vivo. Thus, in some embodiments, the invention provides compositions comprising an HES-oligonucleotide complex containing an oligonucleotide that specifically hybridizes with a target nucleic acid under physiologic conditions.

In some embodiments, an HES-oligonucleotide delivery vehicle of the invention is used to identify the presence of an infectious agent in a host organism such as a virus in a mammalian cell or a bacterium in a mammalian tissue. In this embodiment an HES-oligonucleotide which is composed of an HES, serves as an in vivo marker of binding to a complementary sequence. This identification is accomplished by the detection of changes in fluorescence when binding of the HES-oligonucleotide to a complementary foreign (e.g., infectious agent) nucleic acid sequence results in destruction or significant loss of the HES and results in a loss of fluorescence quenching. Thus, the invention encompasses methods for determining the presence of, and/or quantitating the levels of, a foreign nucleic acid in a host organism (subject). In some embodiments, the method is performed in vitro. In other embodiments, the method is performed in vivo.

In some embodiments, the invention provides a method for detecting the presence of an infectious agent in a subject in vitro or in vivo, comprising, contacting a cell, tissue or subject with an HES-oligonucleotide containing an oligonucleotide that specifically hybridizes with the nucleic acid of an infectious agent, determining the level of fluorescence in the cell, tissue or subject tissue, and comparing said level of fluorescence with that obtained for a control cell, tissue or subject not containing the infectious agent that has been contacted with the HES-oligonucleotide, wherein an increased fluorescence compared to the control indicates that the cell, tissue, or subject has the infectious agent.

In additional embodiments, an HES-oligonucleotide of the invention is used to identify an altered level of a nucleic acid that is a biomarker for a disease or disorder. In some embodiments, the invention provides a method for detecting the presence of an altered level of a nucleic acid biomarker for a disease or disorder in vitro comprising, contacting a cell or tissue with an HES-oligonucleotide containing an oligonucleotide that specifically hybridizes with the nucleic acid biomarker, determining the level of fluorescence in the cell or tissue and comparing said level of fluorescence with that obtained for a control cell or tissue that has been contacted with the HES-oligonucleotide, wherein an altered fluorescence compared to the control indicates that the cell or tissue has an altered level of the nucleic acid biomarker.

In further embodiments, the invention provides a method for detecting an altered level of a nucleic acid biomarker for a disease or disorder in vivo comprising, administerng to a subject an HES-oligonucleotide containing an oligonucleotide that specifically hybridizes with the nucleic acid biomarker, determining the level of fluorescence in the subject, and comparing said level of fluorescence with that obtained for a control subject that has been administered the HES-oligonucleotide, wherein an altered fluorescence compared to the control indicates that the subject has an altered level of the nucleic acid biomarker. This approach can also be used to quantitate the number of copies of an aberrant gene of host origin in vivo.

In vitro and in vivo fluorescence can be monitored using techniques known to those skilled in the art. For example, in some embodiments, fluorescence is monitored via fluorescence endoscopy. Fluorescence endoscopy can be performed using equipment such as, the Olympus EVIS ExERA-II CLV-80 system (Olympus Corp., Tokyo Japan) using the appropriate excitation wavelengths and the emission filters for the administered fluorphores. Fluorescence intensities can be determined using techniques and software known in the art such as, the Image-J software (NIH, Bethesda, Md.).

In some embodiments, the disease or disorder is: cancer, fibrosis, a proliferative disease or disorder, a neurological disease or disorder, and inflammatory disease or disorder, a disease or disorder of the immune system, a disease or disorder of the cardiovascular system, a metabolic disease or disorder, a disease or disorder of the skeletal system, or a disease or disorder of the skin or eyes. In additional embodiments, the disease or disorder is a disease or disorder of the kidneys, liver, lymph nodes, spleen or adipose tissue. In particular embodiments, the disease or disorder is not a disease or disorder of the kidneys, liver, lymph nodes, spleen or adipose tissue.

In further embodiments, the disease or disorder is a proliferative disorder such as, cancer. For example, the overexpression of numerous miRNA such, as mIR-10b, mIR17-92, mIR-21, mIR125b, mIR-155, mIR193a, mIR-205a and mIR-210, have been associated with various forms of cancer. In some embodiments, the biomarker is a miRNA selected from mIR-10b, mIR17-92, mIR-21, mIR125b, mIR-155, mIR193a, mIR-205a, and mIR-210, and an increased fluorescence of the cell, tissue, or subject relative to a control indicates that the subject has cancer or has a predisposition for cancer.

In additional embodiments, the methods of the invention are used to identify and/or distinguish between different diseases or disorders. The methods of the invention can likewise be used to determine among other things, altered nucleic acid (e.g., DNA and RNA) profiles that distinguish between normal and diseased (e.g., cancerous) tissue or cells, discriminate between different subtypes of diseased cells (e.g., between different cancers and subtypes of a particular cancer), to discriminate between mutations (e.g., oncogenic mutations) giving rise to or associated with different disease states, and to identify tissues of origin (e.g., in a metastasized tumor).

Moreover, in some embodiments, the oligonucleotides in the HES-oligonucleotides of the invention are therapeutic oligonucleotides, and the destruction or significant loss of HES that results in an increased fluorescence when the therapeutic HES oligonucleotides specifically hybridizes with target nucleic acids indicates that the therapeutic oligonucleotides have been delivered to, and have hybridized with the target nucleic acid. Thus, in some embodiments, the invention provides a method for monitoring and/or quantitating the delivery of a therapeutic oligonucleotide to a target nucleic acid in vivo, comprising administering to a subject, a HES oligonucleotides containing a therapeutic oligonucleotide that specifically hybridizes to the target nucleic acid, and determining the level of fluorescence in a cell or tissue of the subject, wherein an increased fluorescence in the cell or tissue compared to a control cell or tissue indicates that that the therapeutic oligonucleotide has been delivered to and hybridized with the target nucleic acid.

The delivery vehicles of the invention are based, in part, on the surprising discovery that the linking of one or more HES to a single or multiple strands of oligonucleotides significantly enhances the in vivo delivery of the HES-oligonucleotides inside a cell or tissue of a live organism. Thus, the HES-oligonucleotide vehicles of the invention have applications as therapeutic delivery vehicles for a broad range of therapeutic applications as well as in conjunction with assays and therapies to evaluate for example, the activity and/or number of copies of a specific gene or RNA in vivo.

For use in research and drug discovery, an HES-oligonucleotide of the invention can be used for example, to interfere with the normal function of the nucleic acid molecules to which they are targeted. Expression patterns within cells, tissues, or subjects treated with one or more HES-oligonucleotides of the invention are then compared to control cells, tissues or subjects not treated with the compounds and the patterns produced are then analyzed for differential levels of nucleic acid and/or protein expression and as they pertain, for example, to disease association, signaling pathway, cellular localization, expression level, size, structure or function of the genes examined. These analyses can be performed on stimulated or unstimulated cells and in the presence or absence of other compounds that affect expression patterns.

The invention also provides compositions and methods for modulating nucleic acids and protein encoded or regulated by these modulated nucleic acids. In particular embodiments, the invention provides compositions and methods for modulating the levels, expression, processing or function of a mRNA, small non-coding RNA (e.g., miRNA), a gene or a protein.

In some embodiments, the invention provides a method of delivering an oligonucleotide to a cell in vivo by administering to a subject an HES-oligonucleotide complex containing the oligonucleotide. In particular embodiments, the oligonucleotide is a therapeutic oligonucleotide.

Thus, in some embodiments, the invention encompasses compositions, such as pharmaceutical compositions, comprising an HES-oligonucleotide complex having at least one oligonucleotide hybridizable with a target nucleic, acid sequence under physiologic conditions.

In some embodiments, the invention provides a method of delivering an oligonucleotide to a subject In particular embodiments, the invention provides a method of delivering a therapeutic oligonucleotide to a subject comprising administering an HES-oligonucleotide complex to the subject, wherein the complex contains a therapeutically effective amount of an oligonucleotide sufficient to modulate a target RNA (e.g., mRNA and miRNA) or target gene.

According to one embodiment, the invention provides a method of modulating a target nucleic acid in a subject comprising administering an HES-oligonucleotide complex to the subject., wherein an oligonucleotide of the complex comprises a sequence substantially complementary to the target nucleic acid that specifically hybridizes to and modulates levels of the nucleic acid or interferes with its processing or function. In some embodiments, the target nucleic acid is RNA, in further embodiments the RNA is mRNA or miRNA. In further embodiments, the oligonucleotide reduces the level of a target RNA by at least 10%, at least 20%, at least 30%, at least 40% or at least 50% in one or more cells or tissues of the subject. In some embodiments, the target nucleic acid is a DNA.

According to one embodiment, the invention provides a method of modulating a protein in a subject comprising, administering an HES-oligonucleotide complex to the subject, wherein an oligonucleotide of the complex comprises a sequence substantially complementary to a nucleic acid that encodes the protein or influences the transcription, translation, production, processing or function of the protein. In some embodiments, the oligonucleotide specifically hybridizes to an RNA. In further embodiments the RNA is mRNA or miRNA. In additional embodiments, the oligonucleotide reduces the level of the protein or RNA by at least 10%, at least 20%, at least 30%, at least 40% or at least 50% in one or more cells or tissues of the subject. In some embodiments, the oligonucleotide specifically hybridizes to a DNA.

In particular embodiments, the oligonucleotide in the HES-oligonucleotide complex is selected from an siRNA, an shRNA, a miRNA, an anti-miRNA, a dicer substrate (e.g., dsRNA), an aptamer, a decoy, an antisense oligonucleotide, and a plasmid capable of expressing an siRNA, a miRNA, or an antisense oligonucleotide. In some embodiments, the oligonucleotide specifically hybridizes with an RNA or a sequence encoding an RNA. In other embodiments, the oligonucleotide specifcally hybridizes with DNA sequence encoding an RNA or the regulatory sequences thereof.

In additional embodiments, the expression of a nucleic acid or protein is modulated in a subject by contacting the subject with an HES-oligonucleotide complex containing an antisense oligonucleotide. In particular embodiments, the antisense oligonucleotide in the HES-oligonucleotide complex is a substrate for RNAse H when bound to a target RNA. In some embodiments, the antisense oligonucleotide is a gapmer. As used herein, a "gapmer" refers an antisense compound having a central region (also referred to as a "gap" or "gap segment") positioned between two external flanking regions (also referred to as "wings" or "wing segments"). The regions are differentiated by the types of sugar moieties comprising each distinct region. The types of sugar moieties that are used to differentiate the regions of a gapmer may in some embodiments include beta-D-ribonucleosides, beta-D-deoxyribonucleosides, 2'-modified nucleosides (such 2'-modified nucleosides may include 2'-MOE, 2'-fluoro and 2'-O—CH3, among others), and bicyclic sugar modified nucleosides (such bicyclic sugar modified nucleosides may include LNA™ or ENA™, among others).

In some embodiments, each wing of a gapmer oligonucleotides comprises the same number of subunits. In other embodiments, one wing of a gapmer oligonucleotide comprises a different number of subunits than the other wing of the gapmer. In one embodiment, the wings of gapmer oligonucleotides have, independently, from 1 to about 5 nucleosides of which, 1, 2 3 4 or 5 of the wing nucleosides are sugar modified nucleosides. In one embodiment, the central or gap region contains 8-25 beta-D-ribonucleosides or beta-D-deoxyribonucleosides (i.e., is 8, 9, 10, 11, 12, 13, 14, 15, 16, 17, 18, 19, 20, 21, 22, 24 or 25 nucleosides in length). In a further embodiment, the central or gap region contains 17-24 nucleotides (i.e., is 17, 18, 19, 20, 21, 22, 23 or 24 nucleosides in length). In some embodiments, the gapmer oligonucleotide comprises phosphodiester internucleotide linkages, phosphorothioate internucleotide linkages, or a combination of phosphodiester and phosphorothioate internucleotide linkages. In particular embodiments the central region of the gapmer oligonucleotide contains at least 2, 3, 4, 5 or 10 modified nucleosides, modified internucleoside linkages or combinations thereof. In particular embodiments the central region of the gapmer oligonucleotide contains at least 10 beta-D-2'-deoxy-2'-fluororibofuranosyl nucleosides. In some embodiments, each nucleoside in the central region of the oligonucleotide a beta-D-2'-deoxy-2'-fluororibofuranosyl nucleoside. In one embodiment, the gapmer oligonucleotides is fully complementary over the length complementarity with the target RNA. In one embodiment, one or both wings of the gapmer contains at least one 2' modified nucleoside. In one embodiment, one or both wings of the gapmer contains 1, 2 or 3 2'-MOE modified nucleosides. In one embodiment, one or both wings of the gapmer contains 1, 2 or 3 2'-OCH3 modified nucleosides. In another embodiment, one or both wings of the gapmer contains 1, 2 or 3 LNA or alpha-LNA nucleosides. In some embodiments, the LNA or alpha LNA in the wings of the gapmer contain one or more methyl groups in the (R) or (S) configuration at the 6' (2',4'-constrained-2'-O-ethyl BNA, S-cEt) or the 5'-position (-5'-Me-LNA or -5'-Me-alpha LNA) of LNA or alternatively contain a substituted carbon atom in place of the 2'-oxygen atom in the LNA or alpha LNA. In further embodiments, the LNA or alpha LNA in the gapmer contain a steric bulk moiety at the 5' position (e.g., a methyl group). In a further embodiment, the gap comprises at least one 2' fluoro modified nucleosides. In an additional embodiment, the wings are each 2 or 3 nucleosides in length and the gap region is 19 nucleotides in length. In additional embodiments, the gapmer has at least one 5-methylcytosine.

In another embodiment, the nucleosides of the central region (gap) contain uniform sugar moieties that are different than the sugar moieties in one or both of the external wing regions. In one non-limiting example, the gap is uniformly comprised of a first 2'-modified nucleoside and each of the wings is uniformly comprised of a second 2'-modified nucleoside. For example, in one embodiment, the central region contains 2'-F modified nucleotides flanked on each end by external regions each having two 2'-MOE modified nucleotides (2'-MOE/2'-F/2'-MOE). In particular embodiments, the gapmer is ISIS 393206. In another embodiment, the central region contains 2'-F modified nucleotides flanked on each end by external regions each having two 2'-MOE modified nucleotides (2'-MOE/2'-F/2 WOE). In particular embodiments, the external regions each having two LNA or alpha LNA modified nucleotides in the wings of the gapmer. In further embodiments, the LNA or alpha LNA modified nucleotides contain one or more methyl groups in the (R) or (S) configuration at the 6' (2',4'-constrained-2'-O-ethyl BNA, S-cEt) or the 5'-position (-5'-Me-LNA or -5'-Me-alpha LNA) of LNA or alternatively contain a substituted carbon atom in place of the 2'-oxygen atom in the LNA or alpha LNA.

In another embodiment, the invention provides for the use of an HES-oligonucleotide complex of the invention in the manufacture of a composition for the treatment of one or more of the conditions associated with a miRNA or an miRNA family.

According to one embodiment, the methods comprise the step of administering to or contacting the subject with an effective amount of an HES-oligonucleotide of the invention sufficient to modulate the target gene or RNA (e.g., mRNA and miRNA) expression and to thereby treat one or more conditions or symptoms associated with the disease or disorder. Exemplary compounds of the invention effectively modulate the expression, activity or function of the gene, mRNA or small-non-coding RNA target. In preferred embodiments, the small non-coding RNA target is a miRNA, a pre-miRNA, or a polycistronic or monocistronic pri-miRNA. In additional embodiments, the small non-coding RNA target is a single member of a miRNA family. In a further embodiment, two or more members of a miRNA family are selected for modulation.

In an additional embodiment, the invention provides a method of inhibiting the activity of a target nucleic acid in a subject, comprising administering to the subject an HES-oligonucleotide complex comprising an oligonucleotide which is targeted to nucleic acids comprising or encoding the nucleic acid and which acts to reduce the levels of the nucleic acid and/or interfere with its function in the cell. In particular embodiments, the target nucleic acid is a small-non coding RNA, such as, a miRNA. In some embodiments, the oligonucleotide comprises a sequence substantially complementary to the target nucleic acid.

In some embodiments, some embodiments, the invention provides a method of reducing expression of a target RNA in an subject in need of reducing expression of said target RNA, comprising administering to said subject an antisense HES-oligonucleotide complex. In particular embodiments, an oligonucleotide in the complex is a substrate for RNAse H when bound to said target mRNA. In some embodiments, the oligonucleotide is a gapmer.

In an additional embodiment of the present invention is a method of reducing expression of a target RNA in a subject in need of reducing expression of said target RNA, comprising administering to said subject a HES-oligonucleotide complex containing an antisense oligonucleotide to said subject wherein the antisense sequence specifically hybridizes to the target RNA. In particular embodiments, the antisense oligonucleotide in the HES-oligonucleotide complex is a substrate for RNAse H when bound to a target RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl) ribonucleotides.

In another embodiment, the antisense oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, each nucleoside of the oligonucleotide comprises a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide comprises at least one morpholino motif. In some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (e.g., PMO). In some embodiments, the oligonucleotide sequence is specifically hybridizable to a sequence within 30 nucleotides of the AUG start codon of the target RNA. In additional embodiments, the HES-oligonucleotide sequence is specifically hybridizable to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA (i.e., the miRNA 3'UTR target site in an mRNA). One such example is "miR-Mask" or "target protector," which are single-stranded 2'-O-methyl-modified (or other chemically modified) antisense oligonucleotide fully complementary to predicted miRNA binding sites in the 3'-UTR of a specific target mRNA, covering up the access of the miRNA to its binding site on the target mRNA (see, e.g., Choi et al (2007) Science 318:271; Wang (2011) Methods Mol. Biol. 676:43). In further embodiments, the HES-oligonucleotides are designed to mimic the 3' untranslated sequence in an mRNA that is bound by an miRNA. One such example is "miRNA sponges," competitive miRNA inhibitory transgene expressing multiple tandem binding sites for an endogenous miRNA, which stably interact with the corresponding miRNA and prevent the association of target miRNA with its endogenous target mRNAs. In additional embodiments, the nucleic acid is an mRNA and the oligonucleotide sequence is specifically hybridizable to a target region of a RNA selected from the group consisting of: an intron/exon junction of a target RNA, an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In another embodiment, the invention provides a method of inhibiting the production of a protein, comprising administering to a subject an HES-oligonucleotide complex containing an oligonucleotide which is targeted to nucleic acids encoding the protein or decreases the endogenous expression, processing or function of the protein in the subject. In some embodiments, the oligonucleotide comprises a sequence substantially complementary to a nucleic acid encoding the protein.

In some embodiments, the invention provides a method of decreasing the amount of a target cellular RNA or corresponding protein in a cell by contacting a cell expressing the target RNA with an HES-oligonucleotide complex having an oligonucleotide sequence that specifically hybridizes to the target RNA, wherein the amount of the target RNA or corresponding protein is reduced. In some embodiments, the RNA is an mRNA or a miRNA. In additional embodiments the oligonucleotide is selected from a siRNA, a shRNA, a miRNA, a anti-miRNA, a dicer substrate (e.g., dsRNA), a decoy, an aptamer, a decoy, an antisense oligonucleotide and a plasmid capable of expressing an siRNA, a miRNA, a anti-miRNA, a ribozyme or an antisense oligonucleotide.

In particular embodiments, the oligonucleotide in the HES-oligonucleotide is an antisense oligonucleotide. In one embodiment, the antisense oligonucleotide is a substrate for RNAse H when bound to a target RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides.

In another embodiment, the oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, each nucleoside of the oligonucleotide comprises a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide comprises at least one morpholino motif. In a further embodiment the oligonucleotide comprises at least one phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the target RNA is mRNA and the oligonucleotide sequence specifically hybridizes to a target region of the mRNA selected from the group consisting of an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In some embodiments, the oligonucleotide can induce RNA interference (RNAi). In some embodiments the oligonucleotide is siRNA, shRNA or a Dicer substrate. In some embodiments, the oligonucleotide is a siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

In additional embodiments, the invention provides a method of reducing the expression of a target RNA in a subject in need of such reduced expression of the target RNA, comprising administering to the subject an HES-oligonucleotide complex having an oligonucleotide sequence that specifically hybridizes to the target RNA, wherein the expression of the target RNA in a cell or tissue of the subject is reduced. In some embodiments, the RNA is an mRNA or a miRNA. In additional embodiments the oligonucleotide is selected from a siRNA, shRNA, miRNA, an anti-miRNA, a dicer substrate, an aptamer, a decoy, an antisense oligonucleotide, a plasmid capable of expressing a siRNA, a miRNA, a ribozyme and an antisense oligonucleotide.

In particular embodiments, the oligonucleotide in the HES-oligonucleotide is an antisense oligonucleotide. In one embodiment, the antisense oligonucleotide is a substrate for RNAse H when bound to the target RNA (e.g., mRNA and miRNA). In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides.

In another embodiment, the antisense oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, each of the nucleosides of the oligonucleotide comprise a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide contains at least one morpholino motif. En some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence specifically hybridizes to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the target RNA is mRNA and the oligonucleotide sequence specifically hybridizes to a target region of the target mRNA selected from the group consisting of: an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In some embodiments, the oligonucleotide can induce RNA interference (RNAi). In some embodiments the oligonucleotide is siRNA, shRNA or a Dicer substrate. In some embodiments, the oligonucleotide is a siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

In some embodiments, an HES-oligonucleotide complex is administered to a subject to deliver an oligonucleotide that specifically hybridizes to a target nucleic acid (e.g., gene, mRNA or miRNA), which provides a growth advantage for a tumor cell or enhances the replication of a microorganism. In other embodiments, an HES-oligonucleotide complex is administered to deliver an antisense, siRNA, shRNA, Dicer substrate or miRNA targeting an mRNA sequence coding for a protein (e.g., a protein variant) which has been implicated in a disease. Thus, in some embodiments, the invention provides an in vivo delivery system for transporting specific nucleic acid sequences into live cells to for example, silence genes in organisms afflicted with pathologic conditions due to aberrant gene expression.

In some embodiments, the invention provides a method of decreasing the amount of a polypeptide of interest in a cell, comprising: contacting a cell expressing a nucleic acid that encodes the polypeptide, or a complement thereof, with an HES-oligonucleotide complex having an oligonucleotide sequence specifically hybridizes to a DNA or mRNA encoding the polypeptide, such that the expression of the polypeptide of interest is reduced. In further embodiments the oligonucleotide is selected from a siRNA, shRNA, miRNA, an anti-miRNA, a dicer substrate, an antisense oligonucleotide, a plasmid capable of expressing a siRNA, a miRNA, a ribozyme and an antisense oligonucleotide, and wherein the oligonucleotide specifically hybridizes to a nucleic acid that encodes the polypeptide, or a complement thereof, such that the expression of the polypeptide is reduced. In particular embodiments, the oligonucleotide contains 12 to 30 linked nucleosides. In some embodiments, the complex contains a double-stranded RNA (dsRNA). In some embodiments, the oligonucleotide comprises at least one modified oligonucleotide. In further embodiments, the oligonucleotide comprises at least one modified oligonucleotide motif selected from a 2' modification (e.g., 2'-fluoro, 2'-OME and 2'-methoxyethyl (2'-MOE)) a locked nucleic acid (LNA and alpha LNA), a PNA motif, and morpholino motif.

In particular embodiments, the oligonucleotide in the HES-oligonucleotide complex is antisense sequence and is a substrate for RNAse H when bound to a target RNA. In additional embodiments, the antisense oligonucleotide is a gapmer. In some embodiments, the gapmer is an antisense oligonucleotide that is a chimeric oligonucleotide. In some embodiments, the chimeric oligonucleotide comprises a 2'-deoxynucleotide central gap region positioned between 5' and 3' wing segments. The wing segments contain nucleosides containing at least one 2'-modified sugar. The wing segments are contain nucleosides containing at least one 2' sugar moiety selected from a 2'-O-methoxyethyl sugar moiety or a bicyclic nucleic acid sugar moiety. In some embodiments, the gap segment may be ten 2'-deoxynucleotides in length and each of the wing segments may be five 2'-O-methoxyethyl nucleotides in length. The chimeric oligonucleotide may be uniformly comprised of phosphorothioate internucleoside linkages. Further, each cytosine of the chimeric oligonucleotide may be a 5'-methylcytosine.

In another embodiment, the antisense oligonucleotide is not a substrate for RNAse H when hybridized to the RNA. In some embodiments, each nucleoside of the oligonucleotide comprises a modified sugar moiety comprising a modification at the 2'-position. In some embodiments the oligonucleotide contains at least one PNA motif. In further embodiments, all the monomeric units of the oligonucleotide correspond to a PNA. In other embodiments the oligonucleotide contains at least one morpholino motif. In some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence specifically hybridizes to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the oligonucleotide sequence specifically hybridizes to a target region of a target mRNA selected from the group consisting of an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In further embodiments, the oligonucleotide can induce RNA interference (RNAi). In some embodiments the oligonucleotide is siRNA, shRNA or a Dicer substrate. in some embodiments, the oligonucleotide is an siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

In an additional embodiment, the invention provides a method of increasing the activity of a nucleic acid in a subject, comprising administering to the subject an HES-oligonucleotide complex containing an oligonucleotide which comprises or encodes the nucleic acid or increases the endogenous expression, processing or function of the nucleic acid (e.g., by binding regulatory sequences in the gene encoding the nucleic acid) and which acts to increase the level of the nucleic acid and/or increase its function in the cell. In some embodiments, the oligonucleotide comprises a sequence substantially the same as nucleic acids comprising or encoding the nucleic acid.

In another embodiment, the invention provides a method of increasing the production of a protein, comprising administering to a subject an HES-oligonucleotide complex containing an oligonucleotide which encodes the protein or increases the endogenous expression, processing or function of the protein in the subject. In some embodiments, the oligonucleotide comprises a sequence substantially the same as nucleic acids encoding the protein. In some embodiments, the oligonucleotide shares 100% identity with at least 15 contiguous nucleotides, at least 20 contiguous nucleotides or over the fall-length of an endogenous nucleic acid sequence encoding the protein.

The invention also encompasses a method of treating a disease or disorder characterized by the overexpression of a nucleic acid in a subject, comprising administering to the subject an HES-oligonucleotide complex containing an oligonucleotide which is targeted to a nucleic acid comprising or encoding the nucleic acid and which acts to reduce the levels of the nucleic acid and/or interfere with its function in the subject. In some embodiments, the nucleic acid is DNA, mRNA or miRNA. In additional embodiments the oligonucleotide is selected from an siRNA, an shRNA, a miRNA, an anti-miRNA, a dicer substrate, an antisense oligonucleotide, a plasmid capable of expressing an siRNA, a miRNA, a ribozyme and an antisense oligonucleotide.

In particular embodiments, the nucleic acid is RNA and the oligonucleotide in the HES-oligonucleotide is an antisense oligonucleotide. In one embodiment, the antisense oligonucleotide is a substrate for RNAse H when hybridized to the RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides. In some embodiments, the oligonucleotide comprises a sequence substantially complementary to the nucleic acid.

In another embodiment, the oligonucleotide is not a substrate for RNAse H when bound to the nucleic acid. In some embodiments, each nucleoside of the oligonucleotide comprises a modified sugar moiety comprising a modification at the 2'-position. In some embodiments the oligonucleotide contains at least one PNA motif. In further embodiments, all the monomeric units of the oligonucleotide correspond to a PNA. In other embodiments the oligonucleotide contains at least one morpholino motif. In some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence specifically hybridizes to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the nucleic acid is mRNA and the oligonucleotide sequence specifically hybridizes to a target region of the mRNA selected from the group consisting of: an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In further embodiments, the oligonucleotide can induce RNA interference (RNAi). In some embodiments the oligonucleotide is siRNA, shRNA or a Dicer substrate. In some embodiments, the oligonucleotide is an siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide $3^1$ overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

In further embodiments, the invention encompasses a method of treating a disease or disorder characterized by the overexpression of a protein in a subject, comprising administering to the subject an HES-oligonucleotide complex containing an oligonucleotide which is targeted to a nucleic acid encoding the protein or decreases the endogenous expression, processing or function of the protein in the subject. In some embodiments, the nucleic acid is DNA, mRNA or miRNA. In additional embodiments the oligonucleotide is selected from an siRNA, an shRNA, miRNA, an anti-miRNA, a dicer substrate, an aptamer, a decoy, an antisense oligonucleotide, a plasmid capaLle of expressing an siRNA, an miRNA, a ribozyme and an antisense oligonucleotide. In some embodiments, the oligonucleotide shares 100% identity with at least 15 contiguous nucleotides, at least 20 contiguous nucleotides or over the full-length of an endogenous nucleic acid sequence encoding the protein.

In particular embodiments, the targeted nucleic acid is RNA and the oligonucleotide in the HES-oligonucleotide is an antisense oligonucleotide. In one embodiment, the antisense oligonucleotide is a substrate for RNAse H when hybridized to the RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides. In some embodiments, the oligonucleotide comprises a sequence substantially complementary to the nucleic acid.

In another embodiment, the oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, each nucleoside of the oligonucleotide comprises a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide comprises at least one morpholino motif. In some embodiments, the morpholino is a phosphorodiamidate morpholino. Iii further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence is specifically hybridizable to a sequence in the 5' untranslated region of the target RNA. (e.g., within 30 nucleotides of the AUG start codon) and to reduce translation. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the nucleic acid is mRNA and the oligonucleotide sequence specifically hybridizes to a target region of an mRNA encoding the protein selected from the group consisting of: an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction. In further embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In further embodiments, the oligonucleotide can induce RNA interference (RNAi). In some embodiments the oligonucleotide is siRNA, shRNA or a Dicer substrate. In some embodiments, the oligonucleotide is an siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

The invention also encompasses a method of treating (e.g., alleviating) a disease or disorder characterized by the aberrant expression of a protein in a subject, comprising administering to the subject an HES-oligonucleotide complex, containing an oligonucleotide which specifically hybridizes to the mRNA encoding the protein and alter the splicing of the target RNA (e.g., promoting exon skipping). In some embodiments, each nucleoside of the oligonucleotide comprises at least one modified sugar moiety comprising a modification at the 2'-position. In particular embodiments, the modified oligonucleotide is a 2' OME or 2' allyl. In additional embodiments, the modified oligonucleotide is LNA, alpha LNA (e.g., an LNA or alpha LNA containing a steric bulk moiety at the 5' position (e.g., a methyl group). In some embodiments the oligonucleotide contains at least one PNA motif. In further embodiments, all the monomeric units of the oligonucleotide correspond to a PNA. In other embodiments the oligonucleotide contains at least one morpholino motif. In some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence specifically hybridizes to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, oligonucleotide sequence is specifically hybridizable to a target region of an mRNA selected from the group consisting of: an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction.

In particular embodiments, the disease or disorder is Duchenne Muscular Dystrophy (DMD). In some embodiments, the oligonucleotide specifically hybridizes to mRNA sequence that promotes message splicing to "skip over" exon 44, 45, 50, 51, 52, 53 or 55 of the dystrophin gene. In particular embodiments, the oligonucleotide specifically hybridizes to mRNA sequence that promotes message splicing to "skip over" exon 51 of the dystrophin gene. In particular embodiments, the oligonucleotide in the HES-oligonucleotide complex is AVI-4658 (AVI Biopharma). In other embodiments, the oligonucleotide in the HES-oligonucleotide complex is competes for dystrophin mRNA binding with AVI-4658.

A farther embodiment of the invention provides a method comprising, selecting a subject who has received a diagnosis of a disease or disorder, administering to the subject a therapeutically effective amount of a HES-oligonucleotide complex containing an oligonucleotide that specifically hybridizes to a nucleic acid sequence believed to be associated with or to encode a protein associated with the disease or disorder or a condition related thereto, and monitoring disease progression in the subject.

In some embodiments, the nucleic acid is DNA, mRNA or miRNA. In additional embodiments the oligonucleotide is selected from an siRNA, an shRNA, a miRNA, an anti-miRNA, a dicer substrate, an aptamer, a decoy, an antisense oligonucleotide, a plasmid capable of expressing an siRNA, a miRNA, a ribozyme and an antisense oligonucleotide. In some embodiments, the oligonucleotide shares 100% identity with at least 15 contiguous nucleotides, at least 20 contiguous nucleotides or over the full-length of the nucleic acid.

In particular embodiments, the nucleic acid is RNA and the oligonucleotide in the HES-oligonucleotide is an antisense oligonucleotide. In one embodiment, the antisense oligonucleotide is a substrate for RNAse H when hybridized to the RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a frst wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides. In some embodiments, the oligonucleotide comprises a sequence substantially complementary to the nucleic acid.

In another embodiment, the oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, all the nucleosides of the oligonucleotide comprise a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide comprises at least one morpholino motif. In some embodiments, the morpholino is a phosphorodiamidate morpholino. In additional embodiments, all the monomeric units of the oligonucleotide correspond to a morpholino. In farther embodiments all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence specifically hybridizes to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the oligonucleotide specifically hybridizes to a target region of the mRNA selected from the group consisting of: an intron exon junction of a target RNA, and an intron/exon junction and a region 1 to 50 nucleobases 5' of an intron/exon junction of the target RNA. In some embodiments, the target region is selected from the group consisting of a region 1 to 15 nucleobases 5' of an intron/exon junction, 20 to 24 nucleobases 5' of an intron/exon junction, and 30 to 50 nucleobases 5' of an intron/exon junction. In additional embodiments, the HES-oligonucleotide complex contains an oligonucleotide that specifically hybridizes to nucleotides 1-10 of a miRNA (i.e., the seed region) or that specifically hybridizes to a sequence in a precursor-miRNA (pre-miRNA) or primary-miRNA (pri-miRNA) that when bound by the oligonucleotide blocks miRNA processing.

In further embodiments, the oligonucleotide can induce RNA interference (RNAi). In some embodiments the oligonucleotide is siRNA, shRNA or a Dicer substrate. In some embodiments, the oligonucleotide is an siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof in some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

In another embodiment, the invention provides a method of slowing disease progression in a subject suffering from a disease or disorder correlated with the overexpression of a protein comprising, administering to the subject an HES-oligonucleotide complex containing an oligonucleotide that specifically hybridizes to a DNA or mRNA encoding the protein, such that the expression of the polypeptide is reduced. In additional embodiments the oligonucleotide is selected from an siRNA, an shRNA, a miRNA, an anti-miRNA, a dicer substrate, an antisense oligonucleotide, a plasmid capable of expressing an siRNA, a miRNA, a ribozyme and an antisense oligonucleotide. In some embodiments, the oligonucleotide shares 100% identity with at least 15 contiguous nucleotides, at least 20 contiguous nucleotides or over the full-length of the DNA or mRNA encoding the protein.

In particular embodiments, the nucleic acid is mRNA and the oligonucleotide in the HES-oligonucleotide is an antisense oligonucleotide. In one embodiment, the antisense oligonucleotide is a substrate for RNAse H when hybridized to the RNA. In additional embodiments, the antisense oligonucleotide is a gapmer. In some embodiments, the oligonucleotide is 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl)ribonucleotides. In particular embodiments, the oligonucleotide contains 12 to 30 linked nucleosides. In some embodiments, the oligonucleotide comprises a sequence substantially complementary to the nucleic acid.

In another embodiment, the oligonucleotide is not a substrate for RNAse H when bound to the target RNA (e.g., mRNA and miRNA). In some embodiments, the oligonucleotide comprises at least one modified sugar moiety comprising a modification at the 2'-position. In some embodiments, each nucleoside of the oligonucleotide comprises a modified sugar moiety comprising a modification at the 2'-position. In some embodiments the oligonucleotide comprises at least one PNA motif. In further embodiments, all the monomeric units of the oligonucleotide correspond to a PNA. In other embodiments the oligonucleotide comprises at least one morpholino motif. In some embodiments, the morpholino is a phosphorodiamidate morpholino. In further embodiments, all the monomeric units of the oligonucleotide correspond to a morpholino. In further embodiments, all the monomeric units of the oligonucleotide correspond to a phosphorodiamidate morpholino (PMO). In some embodiments, the oligonucleotide sequence specifically hybridizes to a sequence within 30 nucleotides of the AUG start codon of the target RNA. In additional embodiments, the oligonucleotide sequence is specifically hybridizable to a sequence in the 5' untranslated region of the target RNA. In some embodiments, the HES-oligonucleotides are designed to target the 3' untranslated sequence in an RNA (e.g., mRNA). In further embodiments, the HES-oligonucleotides are designed to target the 3' untranslated sequence in an RNA that is bound by an miRNA. In additional embodiments, the nucleic acid is an mRNA and the oligonucleotide sequence specifically hybridizes to a target region of the mRNA selected from the group consisting of: an intron/exon junction of a target RNA, and an intron/exon junction and a region 1 to 50 nucleobases 5' of an intron/exon junction of the target RNA. In some embodiments, the target region is selected from the group consisting of: a region 1 to 15 nucleobases 5' of an intron/exon junction, 20 to 24 nucleobases 5' of an intron/exon junction, and 30 to 50 nucleobases 5' of an intron/exon junction.

In further embodiments, the oligonucleotide can induce RNA interference (RNAi). In some embodiments the oligonucleotide is siRNA, shRNA or a Dicer substrate. In some embodiments, the oligonucleotide is an siRNA that is 18-35 nucleotides in length. In some embodiments, the oligonucleotide is an shRNA that has a stem of 19 to 29 nucleotides in length and a loop size of between 4-30 nucleotides. In further embodiments the siRNA or shRNA oligonucleotide contains one or more modified nucleosides, modified internucleoside linkages, or combinations thereof. In some embodiments, the oligonucleotide is a Dicer substrate and contains 2 nucleic acid strands that are each 18-25 nucleotides in length and contain a 2 nucleotide 3' overhang. In particular embodiments, the Dicer substrate is a double stranded nucleic acid containing 21 nucleotides in length and contains a two nucleotide 3' overhang. In further embodiments one or both strands of the Dicer substrate contains one or more modified nucleosides, modified internucleoside linkages, or combinations thereof.

Therapeutic Applications on miRNA-Related Pathologies

There currently exist several distinct groups of pathological conditions that are known to be regulated by an miRNA or a family of miRNA, which can be targeted using the HES-oligonucleotide complexes of the present invention.

In one embodiment, an oligonucleotide in an HES-oligonucleotide complex is an inhibitor or mimic of one or more miRNAs associated with an infectious disease. In one embodiment, an oligonucleotide in the HES-oligonucleotide complex of the invention inhibits miR-122. Miravirsen (SPC3649), an inhibitor of miR-122 developed by Santaris Pharma A/S. Mir-122 is a liver specific miRNA that the Hepatitis C virus requires for replication as a critical endogenous host factor. Clinical trial data for 4-week Miravirsen monotherapy has shown robust dose-dependent anti-viral activity. Regulus Therapeutics and GlaxoSmithKline (GSK) have likewise demonstrated in a preclinical study that miR-122 is essential in the replication of HCV and plan to advance an anti-miR-122 into clinical studies for the treatment of HCV infection.

In another embodiment, an oligonucleotide in an HES-oligonucleotide complex is an inhibitor or mimic of an miRNA associated with fibrosis. In one embodiment, an oligonucleotide in the HES-oligonucleotide complex of the invention inhibits miR-21. Preclinical studies by Regulus Pharmaceutical and Sanofi Aventis have shown that inhibition of miR-21, which is upregulated in human fibrotic tissues, can improve organ function in multiple models of fibrosis including heart and kidney. In another embodiment, an oligonucleotide in the HES-oligonucleotide complex of the invention corresponds to or mimics miR-29. MGN-4220, mimics or miRNA replacement therapy by Mirna Therapeutics, targets miR-29 implicated in cardiac fibrosis.

In another embodiment, an oligonucleotide in an HES-oligonucleotide complex is an inhibitor or mimic of an miRNA associated with a cardiovascular disease, including, but not limited to, stroke, heart disease, atherosclerosis, restenosis, thrombosis, anemia, leucopenia, neutropenia, thrombocytopenia, granuloctopenia, pancytoia and idiopathic thrombocytopenic purpura. In one embodiment, an oligonucleotide in the HES-oligonucleotide complex of the invention inhibits miR-33. Regulus Pharmaceutical and AstraZeneca has shown in preclinical studies that the inhibition of miR-33 reduces arterial plaque size and increase levels of HDL. In another embodiment, an oligonucleotide in the HES-oligonucleotide complex of the invention inhibits miR-92, miR-378, miR-206 and/or the miR-143/145 family. MGN-6114, MGN-5804, MGN-2677, MGN-8107, developed by Miragen Therapeutics, respectively targets miR-92 implicated in peripheral arterial disease, miR-378 implicated in cardiometablolic disease, miR-143/145 family implicated in vascular disease, and miR-206 implicated in amylotrophic lateral sclerosis. In a further embodiment, an oligonucleotide in the HES-oligonucleotide complex of the invention inhibits the miR-208/209 family and/or the miR-15/195 family. Miragen Therapeutics's MGN-9103 and MGN-1374 are miRNA inhibitors that respectively target miR-208/209 family for chronic heart failure and miR-15/195 family for post-myocardial infarction remodeling. In another embodiment, an oligonucleotide in the HES-oligonucleotide complex of the invention inhibits miR-126 and/or miR92a. miR-126 and miR-92a play central roles in the development of an atherosclerotic plaque.

In another embodiment, an oligonucleotide in the HES-oligonucleotide complex is an inhibitor of an miRNA associated with a neurological disease or conditions. In one embodiment, an oligonucleotide in the HES-oligonucleotide complex of the invention inhibits miR-206, miR-206 plays a crucial role in ALS and in neuromuscular synapse regeneration.

In another embodiment, an oligonucleotide in the HES-oligonucleotide complex is an inhibitor or mimic of an miRNAs associated with oncological conditions. In one embodiment, an oligonucleotide in the HES-oligonucleotide complex of the invention inhibits miR-21. miR-21 has been suggested by numerous scientific publications to play an important role in the initiation and progression of cancers including liver, kidney, breast, prostate, lung and brain. Anti-miR-21 in hepatocellular carcinoma (HCC) mouse model has shown delayed tumor progression in a preclinical study by Regulus Pharmaceutical and Sanofi Aventis. In another embodiment, an oligonucleotide in the HES-oligonucleotide complex of the invention inhibits miR-10b. Preclinical animal studies of anti-miR-10b by Regulus Pharmaceutical also showed therapeutic effect in GBM model. In an additional embodiment, an oligonucleotide in the HES-oligonucleotide complex of the invention corresponds to or mimics miR-34. Mimics or miRNA replacement therapy by Mirna Therapeutics of miR-34, which is lost or expressed at reduced levels in most solid and hematologic malignancies, showed inhibition of growth for various types of cancers in preclinical studies of MRX34.

In some embodiments, an oligonucleotide in the HES-oligonucleotide complex is an inhibitor of an miRNAs selected from: let-7a, miR-9, miR-10b, miR-15a-miR-16-1, miR-16, miR-21, miR-24, miR-26a, miR-34a, miR-103-107, miR-122, miR-133, miR-181, miR-192, miR-194, miR-200. These microRNAs are among those that have been reported to be associated with cancer.

In some embodiments, an oligonucleotide in the HES-oligonucleotide complex inhibits a miRNA selected from: let-7, let-7a, let-7f, miR-1, Mir-10b, miR-15a-miR-16-1, Mir-17-5p, Mir-17-92, miR-21, Mir-23-27, miR-25, miR-27b, miR-29, miR-30a, Mir-31, miR-34a, miR-92-1, miR-106a, miR-125, Mir-126, Mir-130a, Mir-132, miR-133b, Mir-155, miR-206, Mir-210, Mir-221/222, miR-223, Mir-296, miR-335, Mir-373, Mir-378, miR-380-5p, Mir-424, miR-451, miR-486-5p, and Mir-520c. These microRNAs are among those that have been reported to promote neo-vascularization, metastasis and/or the onset of cancer.

In some embodiments, an oligonucleotide in the HES-oligonucleotide complex inhibits a miRNA selected from: miR-15 family, miR-21, miR-23, miR-24, miR-27, miR-29, miR-33, miR-92a, miR-145, miR-155, miR-199b, miR-208a/b family, miR-320, miR-328, miR-499. These microRNAs are among those that have been reported to have various roles in cardiovascular functions.

In some embodiments, an oligonucleotide in the HES-oligonucleotide complex inhibits a miRNA selected from: let-7b, miR-9, miR106b-25 cluster, miR-124, miR-132, miR-137, miR-184. These microRNAs are among those that have been reported to have various roles in adult neurogenesis in neural stem cells (NSCs).

In some embodiments, an oligonucleotide in the HES-oligonucleotide complex is an inhibitor or mimic of an miRNAs selected from: let-7a, miR-21, mir-26, miR-125b, mir-145, miR-155, miR-191, miR-193a, miR-200 family, miR-205, miR-221, and miR-222. These microRNAs are among those that have been reported to function as diagnostic or prognostic biomarkers for various types of cancers. In particular embodiment, an oligonucleotide in the HES-oligonucleotide complex is an inhibitor of a miRNA selected from: miR-21, mir-26, miR-125b, miR-155, miR-193a, miR-200 family, miR-221, and miR-222. In particular embodiment, an oligonucleotide in the HES-oligonucleotide complex contains the sequence of, or mimics a miRNA selected from: let-7a, mir-145, miR-191, and miR-205.

In some embodiments, an oligonucleotide in the HES-oligonucleotide complex is an inhibitor of an miRNAs selected from: miR-138, mir-182, miR-21, mir-103/107, miR-29c. These microRNAs are among those that have been reported to have roles in arthritis, lupus, atherosclerosis, insulin sensitivity, and albuminuria, respectively.

In some embodiments, an oligonucleotide in the HES-oligonucleotide complex is an inhibitor or mimic of an miRNAs selected from: let-7, let-7-a3, lin-28, miR-1, miR-9-1, miR-15a, miR-16-1, miR-17-92 cluster, miR-21, miR-29 family, miR-34 family, miR-124, miR-127, and miR-290. These microRNAs are among those that have been reported to be dysregulated in various types of cancers due to abnormalities in genetic or epigenetic regulations responsible for miRNA expression. In particular embodiment, an oligonucleotide in the HES-oligonucleotide complex is an inhibitor of a miRNA selected from: let-7-a3, lin-28, miR-17-92 cluster, and miR-21. In particular embodiment, an oligonucleotide in the HES-oligonucleotide complex contains the sequence of, or mimics a miRNA selected from: let-7, miR-1, miR-15a, miR-16-1, miR-21, miR-29 family, miR-34 family, miR-124, miR-127, and miR-290.

In further embodiments, an oligonucleotide in the HES-oligonucleotide complex contains the sequence of, or mimics an miRNA selected from: Mir-20a, Mir-34, Mir-92a, Mir-200c, Mir-217 and Mir-503. These miRNAs are among those that have been reported to be antiangiogenic.

In an additional embodiment, an oligonucleotide in the HES-oligonucleotide complex of the invention contains the sequence of or mimics: miR-1, miR-2, miR-6, miR-7 or let-7. In particular embodiments, the oligonucleotides are miR-Rx07, miR-Rx06, miR-Rxlet-7, miR-Rx01, miR-Rx02 or miR-Rx03. In an additional embodiment, an oligonucleotide in the HES-oligonucleotide complex of the invention corresponds to or mimics miR-451, miR-451 has been demonstrated to regulate erythropoiesis in vivo (Patrick et al.; Genes & Dev., 2010) and thus to be implicated in diseases such as, polycythemia vera, red cell dyscrasias generally, or other hematopoietic malignancies. In particular embodiments, the oligonucleotide is MGN-4893.

In additional embodiments, pharmaceutical compositions comprising an antisense compound targeted to a nucleic acid of interest are used for the preparation of a composition for treating a patient suffering or susceptible to a disease or disorder associated with the nucleic acid.

Ex Vivo Delivery of miRNAs for Nuclear Reprogramming and Generation of iPSCs

In additional embodiments, the invention provides a method for cell nuclear reprograming. In some embodiments, an HES-oligonucleotides containing one or more mimics and/or inhibitor of a miRNA or a plurality of miRNAs are administered ex vivo into cells such as, human and mouse somatic cells to reprogram the cells to have one or more properties of induced pluripotent stem cells (iPSCs) or embryonic stem (ES)-like pluripotent cells (e.g., colony morphology of induced iPSC and embryoid body (EB), expression of stem cell marker genes in the reprogrammed stem cell lines shown by qRT-PCR, hematoxylin and eosin staining of teratomas derived from iPSC clones showing pluripotency of forming mesoderm, endoderm, and ectoderm, immunohistochemistry analysis of iPSC-derived teratoma tissues showing expression of germ layer-specific differentiation markers, teratoma formation upon transplantation into SCID mouse). The non-toxic and highly efficient HES-oligonucleotide delivery system of the invention provides a greatly increased efficiency of delivery method for reprogramming cells compared to conventional oligonucleotide delivery methods (see, e.g., U.S. Publ. Nos. 2010/0075421, US 2009/0246875, US 2009/0203141, and US 2008/0293143).

Examples of miRNAs or mimics of miRNAs that can be administered to somatic cells according to the methods of the present invention and thereby induce reprogramming of the somatic cells to display one or more properties of iPSC include a miRNA or miRNA mimic of a miRNA selected from: lin-28, miR-17-92 cluster, miR-93, miR-106b, miR-106b-25 cluster, miR-106a-363 cluster, miR-181a, miR-199b, miR-200c, miR-214, miR-302, miR-367, miR-302-367 cluster, miR-369, miR-371, miR-372, miR-373, and miR-520, as well as the family members and variants of these miRNAs (see, e.g., Anokye-Danso et al. (2011) Cell Stem Cell 8, 376; Miyoshi et al. (2011) Cell Stem Cell 8, 1; Subramanyam et al. (2011) Nature Biotechnology, 29:5; Li et al. (2011) The EMBO Journal 30:5; Lin et al. (2011) Nucleic Acids Research 39:3; Lakshmipathy et al (2010) Regenerative Medicine 5:4; Xu et al. (2009) Cell 137:647; Goff et al. (2009) PLoS One 4:9; Wilson et al. (2009) Stem Cells Dev. 18:5; Chin et al. (2009) Cell Stem Cell 5:1; Ren et al. (2009) Journal of Translational Medicine 7:20; Lin et al. (2008) RNA 14:2115, the contents of each of which is hereby incorporated by reference in its entirety). Examples of inhibitors of miRNAs that can be administered to somatic cells according to the methods of the present invention and thereby induce reprogramming of the somatic cells to display one or more properties of iPSC include an inhibitor of a miRNA selected from: let-7, miR-145, as well as the family members and variants of these miRNAs (see, e.g., Lakshmipathy et al (2010) Regenerative Medicine 5:4; Xu et al. (2009) Cell 137:647, the contents of each of which is hereby incorporated by reference in its entirety). In further embodiments, the invention encompasses a method of inducing the reprogramming of somatic cells comprising administering to the cells HES-oligonucleotides containing a miRNA, miRNA mimic or miRNA inhibitor of 1, 2, 3, 4, 5 or more of the above miRNAs. Methods for inducing the reprogramming of somatic cells that involve the administration of HES-oligonucleotides containing expression constructs encoding an miRNA, miRNA mimic or miRNA inhibitor of 1, 2, 3, 4, 5 or more of the above miRNAs are also encompassed by the invention.

Methods for inducing the reprogramming of somatic cells that involve the administration of HES-oligonucleotides containing expression constructs encoding an miRNA, miRNA mimic or miRNA inhibitor of 1, 2, 3, 4, 5 or more of the above miRNAs are also encompassed by the invention. "Expression construct" means any double-stranded DNA or double-stranded RNA designed to transcribe an RNA of interest, e.g., a construct that contains at least one promoter which is or may be operably linked to a downstream gene, coding region, or polynucleotide sequence of interest (e.g., a cDNA or genomic DNA fragment that encodes a polypeptide or protein, or an RNA effector molecule, e.g., an antisense RNA, triplex-forming RNA, ribozyme, an artificially selected high affinity RNA ligand (aptamer), a double-stranded RNA, e.g., an RNA molecule comprising a stem-loop or hairpin dsRNA, or a bi-finger or multi-finger dsRNA or a microRNA, or any RNA of interest). An "expression construct" includes a double-stranded DNA or RNA comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression construct into a recipient cell allows the cell to express an RNA effector molecule, polypeptide, or protein encoded by the expression construct. An expression construct may be a genetically engineered plasmid, virus, recombinant virus, or an artificial chromosome derived from, for example, a bacteriophage, adenovirus, adeno-associated virus, retrovirus, lentivirus, poxvirus, or herpesvirus, etc. An expression construct can be replicated in a living cell, or it can be made synthetically.

In particular embodiment, the HES-oligonucleotides contain or encode tandem copies of an miRNA, miRNA mimic and or miRNA inhibitor. For example, in some embodiments, the HES-oligonucleotide contains an expression construct that encodes one or more tandem copies of one or more miRNAs, miRNA mimics and/or miRNA inhibitors wherein the coded sequences are expressed in cis or trans from a single transcription unit or multiple polycistronic transcription units to generate a plurality (e.g., 2, 3, 4, or more) of the same or different, miRNAs, miRNA mimics and/or miRNA inhibitors within the cell (see, e.g., Chung et al. (2006) Nucleic Acids Research 34:7, U.S. Pat. No. 6,471,957, and U.S. Publ. Nos. US 2006/0228800 and US 2011/0105593, the contents of each of which is hereby incorporated by reference in its entirety.

Somatic cells that can be reprogramed according to the methods of the invention can be obtained from any source using techniques known to those of skill in the art, including from a subject to which the reprogramed cells are optionally readministered. Examples of human and mouse sources of somatic cells that can be used according to the methods of the invention, include, but are not limited to human foreskin fibroblasts, human dermal fibroblasts (HDFs), human adipose stromal cells (hASCs), various human cancer cell lines, mouse embryonic fibroblasts (MEFs), and mouse adipose stromal cells (mASCs).

In some embodiments, the methods of the invention involve the step of inducing the somatic reprogramed cells to differentiate into a progenitor or terminal cell lineage by administering to the cells one or more HES-oligonucleotides containing or encoding a miRNA, miRNA mimic or miRNA inhibitor that drives cell lineage specification, for example, to hematopietic cells, cardiomyocytes, hepatocytes, or neurons.

The ability of the HES-oligonucleotides of the invention to safely and efficiently delivery cell nuclear reprogramming oligonucleotides such as certain miRNAs and miRNAs into somatic cell populations additionally makes the methods of the invention amenable to a large-scale high-throughput generation of patient-specific iPSC-like cells from large patient populations for therapeutic uses, that to date, has been hampered by the low reprogramming efficiency and cell cytoxicity concerns presented by conventional nucleic acid delivery systems.

Exemplary Therapeutic Applications of HES-Oligonucleotides

As will be immediately apparent to a person of skill in the art, due in part to the surprising highly efficient in vivo delivery of oligonucleotides into cells, the HES-oligonucleotide complexes of the invention essentially have limitless applications in modulating target nucleic acid and protein levels and activity and are particularly useful in therapeutic applications.

Non limiting examples of diseases and disorder that may be treated with the HES-oligonucleotides of the invention include, a proliferative disorder (e.g., a cancer, such as hematological cancers (e.g., AML, CML, CLL and multiple myeloma) and solid tumors (e.g., melanoma, renal cancer, pancreatic cancer, prostate cancer, ovarian cancer, breast cancer, NSCLC), immune (e.g., ulcerative colitis, Crohn's disease, IBD, psoriasis, asthma, autoimmune diseases such as rheumatoid arthritis, multiple sclerosis, and SLE) and inflammatory diseases, neurologic diseases (e.g., diabetic retinopathy, Duchenne's muscular dystrophy, myotinic dystrophy, Huntington's disease and spinal muscular atrophy and other neurodegenerative diseases), metabolic diseases (e.g., type II diabetes, obesity), cardiovascular diseases (e.g., clotting disorders, thrombosis, coronary artery disease, restenosis, amyloidosis, hemophilia, anemia, hemoglobulinopathies, atherosclerosis, high cholesterol, high tryglycerides), endocrine related diseases and disorders (e.g., NASH, diabetes mellitus, diabetes insipidus, Addison's disease, Turner syndrome, Cushing's syndrome, osteoporosis,) and infectious disease. Thus, in one embodiment, the invention provides a method of treating a disease in a subject comprising administering to a subject that has been diagnosed with the disease, a therapeutically effective amount of an HES-oligonucleotide containing a therapeutic oligonucleotide specifically hybridizes to a nucleic acid associated with the disease or disorder or a symptom thereof.

In additional embodiments, the disease or disorder treated with an HES-oligonucleotide of the invention is a disease or disorder of the kidneys, liver, lymph nodes, spleen or adipose tissue.

The invention also provides a method of monitoring the delivery of a therapeutic oligonucleotide to a cell or tissue in a subject, comprising administering to the subject an HES-oligonucleotide complex containing a therapeutic oligonucleotide and monitoring the fluorescence of cells or tissue in the subject, wherein an increased fluorescence in the cells or tissue of the subject indicates that the therapeutic oligonucleotide has been delivered to the cells or tissue of the subject.

In particular embodiments, the invention provides a method of monitoring the delivery of a therapeutic oligonucleotide to a cell or tissue in a subject, comprising administering to the subject an HES-oligonucleotide complex containing a therapeutic oligonucleotide and monitoring the fluorescence of cells or tissue in the subject, wherein an increased fluorescence in the cells or tissue of the subject to a predetermined value indicates that a therapeutically effective amount of the oligonucleotide has been delivered to the cells or tissue of the subject. In particular embodiments, the predetermined value is determined by extrapolating from corresponding changes in fluorescence associated with delivery of a therapeutically effective amount of the therapeutic HES-oligonucleotide to cells in vitro or through quantitative fluorescence modeling analysis.

The invention also encompasses a method of treating a disease or disorder characterized by the under expression of a nucleic acid in a subject, comprising administering to the subject an HES-oligonucleotide complex containing an oligonucleotide which comprises or encodes the nucleic acid or increases the endogenous expression, processing or function of the nucleic acid (e.g., by binding regulatory sequences in the gene encoding the nucleic acid) and which acts to increase the level of the nucleic acid and/or increase its function in the cell. In some embodiments, the oligonucleotide comprises a sequence substantially the same as a nucleic acid comprising or encoding the nucleic acid.

The invention also encompasses a method of treating a disease or disorder characterized by the underexpression of a protein in a subject, comprising administering to the subject an HES-oligonucleotide complex, containing an oligonucleotide which encodes the protein or increases the endogenous expression, processing or function of the protein in the subject.

In another embodiment, the invention provides a method of treating cancer or one or more conditions associated with cancer by administering a therapeutically effective amount of an HES-oligonucleotide to a subject in need thereof. "Cancer," "tumor," or "malignancy" are used herein as synonymous terms and refer to any of a number of diseases that are characterized by uncontrolled, abnormal proliferation of cells, the ability of affected cells to spread locally or through the bloodstream and lymphatic system to other parts of the body (metastasize), as well as any of a number of known characteristic structural and/or molecular features. A "cancerous tumor" or "malignant cell" is understood as a cell having specific structural properties, lacking differentiation and being capable of invasion and metastasis. Examples of cancers that may be treated using HES-oligonucleotide complexes of the invention include solid tumors and hematologic cancers. Additional, examples of cancers that can be treated using HES-oligonucleotide complexes of the invention include, breast, lung, brain, bone, liver, kidney, colon, head and neck, ovarian, hematopoietic (e.g., leukemia), and prostate cancer. Further examples of cancer that can be treated using HES-oligonucleotide complexes include, but are not limited to, carcinoma, lymphoma, myeloma, blastoma, sarcoma, and leukemia. More particular examples of such cancers include, but are not limited to, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

In additional embodiments, a therapeutically effective amount of an HES-oligonucleotide is administered to treat a hematologic cancer. In further embodiments, the, HES-oligonucleotide is administered to treat a cancer selected from: lymphoma, leukemia, myeloma, lymphoid malignancy, cancer of the spleen, and cancer of the lymph nodes. In additional embodiments, a therapeutically effective amount of an HES-oligonucleotide complex is administered to treat a lymphoma selected from: Burkitt's lymphoma, diffuse large cell lymphoma, follicular lymphoma, Hodgkin's lymphoma, mantle cell lymphoma, marginal zone lymphoma, mucosa-associated-lymphoid tissue B cell lymphoma, non-Hodgkin's lymphoma, small lymphocytic lymphoma, and a T cell lymphoma. In additional embodiments, a therapeutically effective amount of an HES-oligonucleotide complex is administered to treat a leukemia selected from: chronic lymphocytic leukemia, B cell leukemia (CD5+ B lymphocytes), chronic myeloid leukemia, lymphoid leukemia, acute lymphoblastic leukemia, myelodysplasia, myeloid leukemia, acute myeloid leukemia, and secondary leukemia. In additional embodiments, a therapeutically effective amount of an HES-oligonucleotide complex is administered to treat multiple myeloma. Other types of cancer and tumors that can be treated using HES-oligonucleotides are described herein or otherwise known in the art.

In particular embodiments, the HES-oligonucleotide contains an oligonucleotide selected from: AVI-4557 (Cyp 3A4m; AVI Biopharma), ISIS-2372 (Survivin; ISIS); Gem-640 (XIAP; Hybridon), Atu027 (PKN3; Silence Therapeutics), CEQ508 (B catenin; Marina Biotech), GEM 231 (PKA R1α subunit; Idera), Affinitak (Aprinocarsen, ISIS 3521/LY900003; PKC-α; ISIS/Lilly); Aezea (OL(1)p53/EL-625; p53; Eleos Pharma); ISIS 2503 (H-ras; ISIS), EZN-2968 (Hif-1α; Enzon Pharmaceuticals); G4460/LR 3001 (c-Myb; Inex/Genta); LErafAON (c-Raf; NeoPharm), ISIS 5132 (c-Raf; ISIS), Genasense (Oblimersen/G3139; Bcl-2; Genta); SPC2996 (Bcl-2; Santaris Pharma), OGX-427 (Hsp27; ISIS/OncoGene X), LY2181308 (Surivin; Lilly), LY2275796 (EIF4E; Lilly), ISIS-STAT3 Rx (STATS; ISIS), OGX-011 (Custirsen; clusterin; Teva), Veglin (VEGF; VasGene Therapeutics, AP12009 (TGF-β2; Antisense Pharma), GTI-2501 (Ribonucleotide Reductase R1; Lorus Therapeutics), Gem-220 (VEGF; Hybridon); Gem-240 (MEM2; Hybridon), CALAA-19 (M2 subunit ribonucleotide reductase; Arrowhead Research Corporation), Trabedersen (AP 12009; TGFB2; Antisense), GTI-2040 (Ribonucleotide Reductase R2 Lorus Therapeutics), AEG 35156 (XIAP; Aegera Pharma), and MG 98 (DNA methyltransferase; MethylGene/ MGI Pharma/British Biotech). In particular embodiments, an oligonucleotide in an HES-oligonucleotide of the invention competes for target binding with one of the above oligonucleotides.

In additional embodiments, the HES-oligonucleotide contains an oligonucleotide that specifically hybridizes to a nucleic acid sequence that modulates apoptosis, cell survival, angiogenesis, metastasis, aberrant gene regulation, cell cycle, mitogenic pathways and/or growth signaling. In further embodiments, the HES-oligonucleotide contains an oligonucleotide that specifically hybridizes to a nucleic acid sequence that modulates the expression of a protein selected from: from: EGFR, HER-2/neu, ErbB3, cMet, p561ck, PDGFR, VEGF, VEGFR, FGF, FGFR, ANG1, ANG2, bFGF, TIE2, protein kinase C-alpha (PKC-alpha), p561ck PKA, TGF-beta, IGFIR, P12, MDM2, BRCA, IGF1, HGF, PDGF, IGFBP2, IGFIR, HIF1 alpha, ferritin, transferrin receptor, TMPRSS2, IRE, HSP27, HSP70, HSP90, MITF, clusterin, PARP1C-fos, C-myc, n-myc, C-raf, B-raf, A1, H-raf, Skp2, K-ras, N-ras, H-ras, farensyltransferase, c-Src, Jun, Fos, Bcr-Abl, c-Kit, EphA2, PDGFB, ARF, NOX1, NF1STAT3, E6/E7, APC, WNT, beta catenin, GSK3b, PI3k, mTOR, Akt, PDK-1, CDK, Mek1, ERK1, AP-1, p53, Rb, Syk, osteopontin, CD44, MEK, MAPK, NF kappa beta, E cadherin, cyclin D, cyclin E, Bcl-2, Bax, BXL-XL, BCL-W, MCL1, ER, MDR, telomerase, telomerase reverse transcriptase, a DNA methyltransferase, a histone deacetlyase (e.g., HDAC1 and HDAC2), an integrin, an IAP, an aurora kinase, a metalloprotease (e.g., MMP2, MMP3 and MMP9), a proteasome, and a metallothionein gene.

In another embodiment, the invention provides a method of treating cancer or one or more conditions associated with cancer by administering an HES-oligonucleotide in combination with one or more therapies currently being used, have been used, or are known to be useful in the treatment of cancer or conditions associated with cancer.

In some embodiments, the invention provides a method of treating an inflammatory or other disease or disorder of the immune system, or one or more conditions associated with an inflammatory or other disease or disorder of the immune system, said method comprising administering to a subject in need thereof (i.e., having or at risk of having an inflammatory or other immune system disease or disorder), a therapeutically effective amount of one or more HES-oligonucleotides of the invention. As immediately apparent to those skilled in the art, any type of immune or inflammatory disease or condition resulting from or associated with an immune system or inflammatory disease can be treated in accordance with the methods of the invention. In particular embodiments, the invention is directed to treating an immune system and/or inflammatory disease or disorder, or one or more conditions associated with such an immune disease or disorder.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders additionally include but are not limited to those affecting the blood vessels (polyarteritis, temporarl arteritis); joints (arthritis: crystalline, osteo-, psoriatic, reactive, rheumatoid, Reiter's); gastrointestinal tract (Disease); skin (dermatitis); or multiple organs and tissues (systemic lupus erythematosus). The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis. In particular embodiments, the inflammatory disorder is selected from the group consisting of asthma, allergic disorders, and rheumatoid arthritis.

In further embodiment, the disorder or disorder of the immune system is an autoimmune disease. Autoimmune diseases, disorders or conditions that may be treated using the HES-oligonucleotide complexes of the invention include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis, systemic lupus erythematous, discoid lupus, Goodpasture's syndrome, Pemphigus, Receptor autoimmunities for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drag resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders. In particular embodiments, the autoimmune disease or disorder is selected from Crohn's disease, Systemic lupus erythematous (SLE), inflammatory bowel disease, psoriasis, diabetes, ulcerative colitis, multiple sclerosis, and rheumatoid arthritis.

In some embodiment, the invention is directed to methods of treating an immune or cardiovascular disease comprising administering to a subject a therapeutically effective amount of an HES-oligonucleotide. In particular embodiments, the HES-oligonucleotide complex contains an oligonucleotide selected from: Alicaforsen (ICAM-1; ISIS 2302), QPI-1002 (p53; Silence Thera/Novartis/Quark), XEN701 (Isis/Xenon Pharmaceuticals), ISIS 104838 (TNF-α; ISIS/Orasense), EPI-2010 (RASON; Adenosine A1 receptor; Epigenesis/Genta), Plazomicin (Isis/Achaogen), ALN-PCS02 (PCSK9; Alnylam), ALN-AT3 (SERPINC1; Alnylam), ALN-HPN (TFR2; Alnylam), ALN-HPN (TMPRSS6; Alnylam), ASM8-003 (CCR3; Topigen Pharmaceuticals), ISIS CRP Rx (CRP; ISIS), Kynamro™ (ISIS 301012; Apo-B100; ISIS/Genzyme), ISIS-APOCIII Rx (ApoCIII; ISIS), ISIS-APO(a) (Apo(a); ISIS); ISIS-FVII rx Factor VII; ISIS), and ISIS-FXI (Factor XI; ISIS). In particular embodiments, an oligonucleotide in an HES-oligonucleotide complex of the invention competes with one of the above oligonucleotides for target binding.

In some embodiments, the invention provides a method of treating an infectious disease or one or more conditions associated with an infectious disease, said method comprising administering to a subject in need thereof (i.e., having or at risk of having an infectious disease), a therapeutically effective amount of one or more HES-oligonucleotides of the invention. In some embodiments the infectious disease is a viral infection, a bacterial infection, a fungal infection or a parasite infection.

In some embodiments, the invention provides a method of treating an infection or condition associated with a category A infectious agent or disease, said method comprising administering to a subject in need thereof (i.e., having or at risk of having an infectious disease), a therapeutically effective amount of one or more HES-oligonucleotides of the invention. In particular embodiments, the infectious agent is selected from *Bacillus anthracis, Clostridium botulinum* toxin, *yersina pestis, variola major* a filovirus (e.g., Ebola and Marburg) and an arenavirus (e.g., Lassa and Machupo). In particular embodiments, the condition treated according to the methods of the invention is selected from: anthrax, botulism, plague, smallpox, tularemia, and a viral hemorrhagic fever.

In some embodiments, the invention provides a method of treating an infection or condition associated with a category B infectious agent or disease, said method comprising administering to a subject in need thereof (i.e., having or at risk of having an infectious disease), a therapeutically effective amount of one or more HES-oligonucleotides of the invention. In particular embodiments, the infectious agent is selected from: a *Bacilla* species, *Clostridium perfringens*, a *Salmonella* species, *E. coli* O157:H7, *Shigella, Burkholderia pseudomallei, Chyamydia psittaci, Coxiella burnetii, Rickettsia prowazekii*, a viral encephalitis alphavirus (e.g., Venezuelan equine encephalitis, eastern equine encephalitis, western equine encephalitis), *Vibrio cholerae* and *Cryptosporidium parvum*. In particular embodiments, the condition treated according to the methods of the invention is selected from: Brucellosis, epsilon toxin of *Clostridium perfringens*, food poisoning, Glanders, Melioidosis, Psittacosis, Q fever, ricin toxin poisoning, typhus fever, viral encephalitis and dysentery.

In some embodiments, the invention provides a method of treating a viral infection or one or more conditions associated with a viral infection, said method comprising administering to a subject in need thereof (i.e., having or at risk of having a viral infection), a therapeutically effective amount of one or more HES-oligonucleotides of the invention. As immediately apparent to those skilled in the art, any type of viral infection or condition resulting from or associated with a viral infection (e.g., a respiratory condition) can be treated in accordance with the methods of the invention. In particular embodiments, the viral disease or disorder is an infection or condition associated with a member selected from: Ebola, Marburg, Junin, Denge West Nile, Lassa SARS Co-V, Japanese encephalitis, Venezuelan equine encephalitis, Saint Louis encephalitis, Manchupo, Yellow fever, and Influenza.

Examples of viruses which cause viral infections and conditions that can be treated with the HES-oligonucleotides of the invention include, but are not limited to, infections and conditions associated with retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenavirus (e.g., lassa fever virus), paramyxoviruses (e.g., morbillivirus virus, human respiratory syncytial virus, mumps, hMPV, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C and PIV), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus).

In additional embodiments, the invention provides a method of treating or alleviating conditions associated with viral respiratory infections associated with or that cause the common cold, viral pharyngitis, viral laryngitis, viral croup, viral bronchitis, influenza, parainfluenza viral diseases ("PIV") diseases (e.g., croup, bronchiolitis, bronchitis, pneumonia), respiratory syncytial virus ("RSV") diseases, metapneumavirus diseases, and adenovirus diseases (e.g., febrile respiratory disease, croup, bronchitis, and pneumonia).

In some embodiment, the HES-oligonucleotide contains an oligonucleotide selected from: AVI-4065 (HCV; AVI Biopharma), VRX496 (HIV; VIRxSYS corporation), Miravirsen (antimiR-122, Santaris), GEM 91 (Trecorvirsen)/92; Gag HIV; Hybridon), Vitravene (Fomivirsen; CMV; ISIS/Novartis), ALN-RSV01 (RSV; Alnylam), AVI-6002 (Ebola; AVI Biopharma), AVI-6003 (Ebola; AVI Biopharma), MBI-1121 (human papillomavirus; Hybridon), ARC-520 (HPV hepatitis; Arrowhead Research Corporation) and AVI-6001 (Influenza/avian flu; AVI Biopharma). In particular embodiments, an oligonucleotide in an HES-oligonucleotide of the invention competes for target binding with one of the above oligonucleotides.

In an additional embodiment, the invention provides a method of treating a viral infection or one or more conditions associated with a viral infection by administering a combination of at least 1, at least 2, at least 3, at least 4, or at least 5 HES-oligonucleotides of the invention. In some embodiments at least 2, at least 3, or at least 4 of the HES-oligonucleotides specifically hybridizes to the same target nucleic acid. In additional embodiments, at least 2, at least 3, or at least 4 or at least 5 of the HES-oligonucleotides bind to a different target nucleic acid.

In one embodiment, the invention provides a method of treating a filovirus (e.g., Ebola and Marbury) infection or one or more conditions associated with the infection by administering to a patient in need thereof, a therapeutically effective amount of HES-oligonucleotides that specifically hybridize to at least 1, at least 2, at least 3, at least 4, at least 5, at least 6, at least 7, at least 8, at least 9 or at least 10 RNA sequences of a filovirus. In particular embodiments, the HES-oligonucleotides bind VP35, VP24 and/or RNA polymerase L. In further embodiments one or more of the HES-oligonucleotides are PMOs or PPMOs. In additional embodiments one or more of the HES-oligonucleotides is an antisense, an siRNA or an shRNA.

In one embodiment, the invention provides a method of treating an Ebola virus infection or one or more conditions associated with the infection by administering to a patient in need thereof, HES-oligonucleotides that bind to at least 1, at least 2, at least 3, at least 4, at least 5, at, least 6, at least 7, at least 8, at least 9 or at least 10 Ebola RNA sequences. In particular embodiments, the HES-oligonucleotides bind VP24, VP35, and/or RNA polymerase L. In additional embodiments, the HES-oligonucleotides bind VP24, VP30, VP35, VP40, NP, GP and/or RNA polymerase L. In further embodiments one or more of the HES-oligonucleotides are PMOs or PPMOs. In additional embodiments one or more of the HES-oligonucleotides is an antisense, an siRNA or an shRNA.

In one embodiment, the invention provides a method of treating an Flaviviridae (e.g., West Nile, yellow fever, Japanese encephalitis, and dengue viruses) viral infection or one or more conditions associated with the infection by administering to a patient in need thereof, a therapeutically effective amount of HES-oligonucleotides that specifically hybridize to at least 1, at least 2, at least 3, at least 4, or at least 5 RNA sequences of a member of the family Flaviviridae. In particular embodiments, the HES-oligonucleotides bind the highly conserved non coding sequence in the 5' or 3' regions of the viral genome, or sequence corresponding to the envelope coding gene (E). In farther embodiments one or more of the HES-oligonucleotides are PMOs or PPMOs. In additional embodiments one or more of the HES-oligonucleotides is an antisense, an siRNA or an shRNA.

In one embodiment, the invention provides a method of treating an Arenavirideae (e.g., Lassa, Junin and Machupo viruses) family viral infection or one or more conditions associated with the infection by administering to a patient in need thereof, a therapeutically effective amount of HES-oligonucleotides that specifically hybridizes to at least 1, at least 2, at least 3, at least 4, or at least 5 RNA sequences of a member of the family Arenavirideae. In particular embodiments, the HES-oligonucleotides bind the highly conserved non coding sequence in the 5' or 3' viral mRNAs transcript coding for the Z protein (zinc-binding protein), L protein (viral polymerase), or the GPC (glycoprotein precursor) protein. In further embodiments one or more of the HES-oligonucleotides are PMOs or PPMOs. In additional embodiments one or more of the HES-oligonucleotides is an antisense, an siRNA or an shRNA.

In one embodiment, the invention provides a method of treating a SARS-associated coronavirus (SARS Co-V) infection or one or more conditions associated with the infection by administering to a patient in need thereof, a therapeutically effective amount of HES-oligonucleotides that specifically hybridize to at least 1, at least 2, at least 3, at least 4, or at least 5 family SARS Co-V nucleic acid sequences. In particular embodiments, the HES-oligonucleotides bind the replica se gene (orf 1a/1b), orf 1b ribosomal frameshift point, 5' untranslated region (UTR) of the transcription regulatory sequence (TRS), 3' UTR of the TRS sequence, spike protein-coding region and/or the NSP12 region. In further embodiments one or more of the HES-oligonucleotides are PMOs or PPMOs. In additional embodiments one or more of the HES-oligonucleotides is an antisense, an siRNA or an shRNA.

In one embodiment, the invention provides a method of treating a Retroviridae (e.g., HIV viruses) family viral infection or one or more conditions associated with the infection by administering to a patient in need thereof, a therapeutically effective amount of HES-oligonucleotides that specifically hybridize to at least 2, at least 3, at least 4, or at least 5 RNA sequences of a member of the family Retroviridae. In particular embodiments, the HES-oligonucleotide(s) bind the highly conserved regions of the gag, pol, int, and Vpu regions. In further embodiments one or more of the HES-oligonucleotides are PMOs or PPMOs. In additional embodiments one or more of the HES-oligonucleotides is an antisense, an siRNA or an shRNA.

In another embodiment, the invention provides a method of treating an influenza A (e.g., H1N1, H3N2 and H5N1) infection or one or more conditions associated with influenza by administering to a patient in need thereof, a therapeutically effective amount of HES-oligonucleotides that specifically hybridize to at least 2, at least 3, at least 4, or at least 5 influenza RNA sequences. In particular embodiments, the HES-oligonucleotides bind NP and PA nucleic acid sequence of the virus. In particular embodiments, the HES-oligonucleotides bind an NP, M2, and/or PB2 (e.g., targeting the AUG start codon of PA, PB1, PB2, and NP), or terminal region of NP), NS1 and/or PA nucleic acid sequence of the virus. In further embodiments one or more of the HES-oligonucleotides are PMOs or PPMOs. In additional embodiments one or more of the HES-oligonucleotides is an antisense, an siRNA or an shRNA.

In an additional embodiment, the invention provides a method of treating an alphavirus (equine encephalitis virus (VEEV)) infection or one or more conditions associated with an alphavirus infection by administering to a patient in need thereof, a therapeutically effective amount of HES-oligonucleotides that specifically hybridize to at least 2, at least 3, at least 4, or at least 5 alphavirus RNA sequences. In particular embodiments, the HES-oligonucleotides bind NP and PA nucleic acid sequence of the virus. In particular embodiments, the HES-oligonucleotides bind an nsp1, nsp4 and/or E1 RNA sequence of the virus. In further embodiments one or more of the HES-oligonucleotides are PMOs or PPMOs. In additional embodiments one or more of the HES-oligonucleotides is an antisense, an siRNA or an shRNA.

In some embodiments, the invention provides a method of treating a bacterial infection or one or more conditions associated with a bacterial infection, said method comprising administering to a subject in need thereof (i.e., having or at risk of having a bacterial infection), a therapeutically effective amount of one or more HES-oligonucleotides of the invention. Any type of bacterial infection or condition resulting from, or associated with a bacterial infection can be treated using the compositions and methods of the invention. In particular embodiments, the bacterial infection or condition treated according to the methods of the invention is associated with a member of a bacterial genus selected from: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus,*

Streptococcus, Legionella, Mycobacterium, Proteus, Campylobacter, Enterococcus, Acinetobacter, Morganella, Moraxella, Citrobacter, Rickettsia and Rochlimeae. In further embodiments, the bacterial infection or condition treated according to the methods of the invention is associated with a member of a bacterial genus selected from: P. aeruginosa; E, coli, P. cepacia, S. epidermis, E. faecalis, S. pneumonias, S. aureus, N. meningitidis, S. pyogenes, Pasteurella multocida, Treponema pallidum, and P. mirabilis. In some embodiments, the bacterial infection is an intracellular bacterial infection. In additional embodiments, the invention provides a method of treating an bacterial infection or one or more conditions associated with a bacterial infection by administering to a patient in need thereof, a therapeutically effective amount of HES-oligonucleotides that specifically hybridize to at least 1, at least 2, at least 3, at least 4, or at least 5 nucleic acid sequences of at least 1, at least 2, at least 3, at least 4, or at least 5 of the above bacteria.

In additional embodiments, the invention provides a method of treating a fungal infection or one or more conditions associated with a fungal infection, said method comprising administering to a subject in need thereof (i.e., having or at risk of having a fungal infection), a therapeutically effective amount of one or more HES-oligonucleotides of the invention. Any type of fungal infection or condition resulting from or associated with a fungal infection can be treated using the compositions and methods of the invention. In particular embodiments, the fungal infection or condition treated according to the methods of the invention is associated with a fungus selected from: *Cryptococcus neoformans; Blastomyces dermatitidis; Aiellomyces dermatitidis; Histoplasma capsulatum; Coccidioides immitis*; a *Candida* species, including *C. albicans, C. tropicalis, C. parapsilosis, C. guilliermondii* and *C. krusei*, an *Aspergillus* species, including *A. fumigatus, A. flavus* and *A. niger*; a *Rhizopus* species; a *Rhizomucor* species; a *Cunninghammella* species; a *Apophysomyces* species, including *A. saksenaea, A. mucor* and *A. absidia; Sporothrix schenckii, Paracoccidioides brasiliensis; Pseudalleseheria boydii, Torulopsis glabrata*; a *Trichophyton* species, a *Microsporum* species and a *Dermatophyres* species, or any other fungus (e.g., yeast) known or identified to be pathogenic. In additional embodiments, the invention provides a method of treating a fungal infection or condition associated with a fungi infection by administering to a patient in need thereof, a therapeutically effective amount of HES-oligonucleotides that specifically hybridize to at least 1, at least 2, at least 3, at least 4, or at least 5 nucleic acid sequences of at least 1, at least 2, at least 3, at least 4, or at least 5 of the above funghi.

In additional embodiments, the invention provides a method of treating a parasite infection or one or more conditions associated with a parasite infection, said method comprising administering to a subject in need thereof (i.e., having or at risk of having a parasite infection), a therapeutically effective amount of one or more HES-oligoliucleotides of the invention. Any type of parasite infection or condition resulting from or associated with a parasite infection can be treated using the compositions and methods of the invention. In particular embodiments, the parasite infection or condition treated according to the methods of the invention is associated with a parasite selected from: a member of the *Apicomplexa* phylum such as, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* or *Gregarina* spp.; *Pneumocystis carinii*; a member of the *Microspora* phylum such as, *Nosema, Enterocytozoon, Encephalitozoon, Septata, Mrazekia, Amblyospora, Arneson, Glugea, Pleistophora* and *Microsporidium* spp.; and a member of the *Ascetospora* phylum such as, *Haplosporidium* spp. In further embodiments, the parasite infection or condition treated according to the methods of the invention is associated with a parasite species selected from: *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium, Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia Bovis, B. divergens, B. microti, Isospora belli, L. hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirlus pubis*; and *Dermatobia hominis*, as well as any other parasite known or identified to be pathogenic. In additional embodiments, the invention provides a method of treating an parasite infection or one or more conditions associated with a parasite infection by administering to a patient in need thereof, a therapeutically effective amount of HES-oligonucleotides that specifically hybridize to at least 1, at least 2, at least 3, at least 4, or at least 5 nucleic acid sequences of at least 1, at least 2, at least 3, at least 4, or at least 5 of the above parasites.

In another embodiment, the invention provides a method of treating a viral infection or one or more conditions associated with a viral infection by administering an HES-oligonucleotide of the invention in combination with one or more therapies currently being used, have been used, or are known to be useful in the treatment of a viral infection or conditions associated with a viral infection, including but not limited to, anti-viral agents such as amantadine, oseltamivir, ribaviran, palivizumab, and anamivir. In certain embodiments, a therapeutically effective amount of one or more HES-oligonucleotides of the invention is administered in combination with one or more anti-viral agents such as, but not limited to, amantadine, rimantadine, oseltamivir, znamivir, ribaviran, RSV-IVIG (i.e., intravenous immune globulin infusion) (RESPIGAM™), and palivizumab.

In some embodiments, the invention provides a method of treating an respiratory disease or one or more conditions associated with a respiratory disease, said method comprising administering to a subject in need thereof (i.e., having or at risk of having an respiratory disease), a therapeutically effective amount of one or more HES-oligonucleotides of the invention. The term "respiratory disease," as used herein, refers to a disease affecting organs involved in breathing, such as the nose, throat, larynx, trachea, bronchi, and lungs. Respiratory diseases that can be treated according to the methods of the invention include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In some embodiments, the invention provides a method of treating an neurological condition or disorder, said method comprising administering to a subject in need thereof (i.e., having or at risk of having a neurological condition or disorder), a therapeutically effective amount of one or more HES-oligonucleotides of the invention. The term "neurological condition or disorder" is used herein to refer to conditions that include neurodegenerative conditions, neuronal cell or tissue injuries characterized by dysfunction of the central or peripheral nervous system or by necrosis and/or apoptosis of neuronal cells or tissue, and neuronal cell or tissue damage associated with trophic factor deprivation. Examples of neurodegenerative diseases that can be treated using the HES-oligonucleotide of the invention include, but are not limited to, familial and sporadic amyotrophic lateral sclerosis (FALS and ALS, respectively), familial and sporadic Parkinson's disease, Huntington's disease (Huntington's chorea), familial and sporadic Alzheimer's disease, Spinal Muscular Atrophy (SMA), optical neuropathies such as glaucoma or associated disease involving retinal degeneration, diabetic neuropathy, or macular degeneration, hearing loss due to degeneration of inner ear sensory cells or neurons, epilepsy, Bell's palsy, frontotemporal dementia with parkinsonism linked to chromosome 17 (FTDP-17), multiple sclerosis, diffuse cerebral cortical atrophy, Lewy-body dementia, Pick disease, trinucleotide repeat disease, prion disorder, and Shy-Drager syndrome. Examples of neuronal cell or tissue injuries that can be treating using HES-oligonucleotides of the invention include, but are not limited to, acute and non-acute injury found after blunt or surgical trauma (including post-surgical cognitive dysfunction and spinal cord or brain stem injury) and ischemic conditions restricting (temporarily or permanently) blood flow such as that associated with global and focal cerebral ischemia (stroke); incisions or cuts for instance to cerebral tissue or spinal cord; lesions or placques in neuronal tissues; deprivation of trophic factor(s) needed for growth and survival of cells; and exposure to neurotoxins such as chemotherapeutic agents; as well as incidental to other disease states such as chronic metabolic diseases such as diabetes and renal dysfunction.

In some embodiment, the invention is directed to methods of treating a neurological condition or disorder comprising administering to a subject a therapeutically effective amount of an HES-oligonucleotide. In particular embodiments, the HES-oligonucleotide complex contains an oligonucleotide selected from: AVI-4658 (Dystrophin (exon-skipping); AVI Biopharma), ISIS-SMN Rx (SMN; ISIS/Biogen Idec), AVI-5126 (CABG; AVI Biopharma) and ATL1102 (VLA-4 (CD49d); ISIS/Antisense Therapeutics Ltd). In particular embodiments, an oligonucleotide in an HES-oligonucleotide complex of the invention competes with one of the above oligonucleotides for target binding.

In some embodiment, the invention is directed to methods of treating a metabolic disorder comprising administering to a subject a therapeutically effective amount of an HES-oligonucleotide. In particular embodiments, the HES-oligonucleotide complex contains an oligonucleotide selected from: ISIS-FGFR4 (FGFR4; ISIS), ISIS-GCCR RX (GCC; ISIS), ISIS-GCGR RX (GCG; ISIS), ISIS-PTP1B (PTP1VB; ISIS), iCo-007 (c-Raf; Isis/iCo Therapeutics Inc) ISIS-DGATRX (DGAT; ISIS), PF-04523655 (DME, Silence Thera/Pfizer/Quark), ISIS-TTR Rx (TTR: ISIS/GSI); ISIS-AAT Rx (AAT: ISIS/GSK), ALN-TTRsc (Transerythrin; Alnylam), ALN-TTR01 (Transerythrin; Alnylam), and ALN-TTR02 (Transerythrin; Alnylam). In particular embodiments, an oligonucleotide in an HES-oligonucleotide complex of the invention competes with one of the above oligonucleotides for target binding.

In some embodiment, the invention is directed to methods of treating a disease comprising administering to a subject a therapeutically effective amount of an HES-oligonucleotide. In particular embodiments, the HES-oligonucleotide complex contains an oligonucleotide selected from: ATL1103-GHr Rx (GHr; ISIS/Antisense Therapeutics Ltd), EXC 001 (CTGF; ISIS/Excaliard), and Atu111 (PKN3; Silence Thera). In particular embodiments, an oligonucleotide in an HES-oligonucleotide complex of the invention competes with one of the above oligonucleotides for target binding.

In addition to those described above, HES-oligonucleotides of the invention have applications including but not limited to; treating metabolic diseases or disorders (e.g., mellitus, obesity, high cholesterol, high triglycerides), in treating diseases and disorder of the skeletal system (e.g., osteoporosis and osteoarthritis), in treating diseases and disorders of the cardiovascular system (e.g., stroke, heart disease, atherosclerosis, restenosis, thrombosis, anemia, leucopenia, neutropenia, thrombocytopenia, granuloctopenia, pancytoia or idiopathic thrombocytopenic purpura); in treating diseases and disorders of the kidneys (e.g., nephropathy), pancreas (e.g., pancreatitis), skin and eyes (e.g., conjunctivitis, retinitis, scleritis, uveitis, allergic conjuctivitis, vernal conjunctivitis, pappillary conjunctivitis glaucoma, retinopathy, and ocular ischemic conditions including anterior ischemic optic neuropathy, age-related macular degeneration (AMD), Ischemic Optic Neuropathy (ION), dry eye syndrome); in preventing organ transplantation rejection (e.g., lung, liver, heart, pancreas, and kidney transplantation) and uses in regenerative medicine (e.g., in counteracting aging, in promoting wound healing and stimulating bone, collagen, tissue and organ growth and repair).

In various embodiments, the invention provides compositions for use in modulating a target nucleic acid or protein in a cell, in vivo in a subject, or ex vivo. The HES-oligonucleotide compostions of the invention have applications in for example, treating a disease or disorder characterized by an overexpression, underexpression and/or aberrant expression of a nucleic acid or protein in a subject in vivo or ex vivo. Uses of the compositions of the invention in treating exemplary diseases or disorders selected from: an infectious disease, cancer, a proliferative disease or disorder, a neurological disease or disorder, and inflammatory disease or disorder, a disease or disorder of the immune system, a disease or disorder of the cardiovascular system, a metabolic disease or disorder, a disease or disorder of the skeletal system, and a disease or disorder of the skin or eyes are also encompassed by the invention.

As one of skill in the art will immediately appreciate, the therapeutic and companion diagnostic uses of the HES-oligonucleotides of the invention are essentially limitless. Provided herein are exemplary diagnostic and therapeutic uses of the compositions of the HES-oligonucleotides of the invention. However, the description herein is not meant to be limiting and it is envisioned that the HES-oligonucleotides have uses in any situations where it is desirable to detect a nucleic acid sequence or to modulate levels of one or more nucleic acids or related proteins in a cell and/or organism.

Plurality of HES-Oligonucleotides

In some embodiments, the pharmaceutical compositions of the invention comprise a combination of at least 2, at least 3, at least 4, at least 5, or at least 10 different HES-oligonucleotide complexes having different oligonucleotide sequences. In some embodiments, the pharmaceutical compositions contain between 2-15, 2-10, or 2-5 different HES-oligonucleotide complexes. In some embodiments, at least 2 or at least 3 of the different oligonucleotides in the complex specifically hybridize to a DNA and/or mRNA corresponding to the same polypeptide. In some embodiments, at least 2, at least 3, at least 4, at least 5, or at least 10 of the different oligonucleotides in the complex specifically hybridizes to a DNA and/or mRNA corresponding to different polypeptides. In some embodiments, the pharmaceutical compositions contain between 2-15, 2-10, or 2-5 oligonucleotides that specifically hybridize to different polypeptides. In some embodiments, one or more of the different HES-oligonucleotides are administered to a subject concurrently. In other embodiments, one or more of the different HES-oligonucleotides are administered to a subject separately.

In certain embodiments, an HES-oligonucleotide complex of the invention is co-administered with one or more additional agents. In certain embodiments, such additional agents are designed to treat a different disease, disorder, or condition as the HES-oligonucleotide complex. In some embodiments, the additional agent is co-administered with the HES-oligonucleotide complex to treat an undesired effect of the complex. In additional embodiments, the additional agent is co-administered with the HES-oligonucleotide complex to produce a combinational effect. In further embodiments, the additional agent is co-administered with the HES-oligonucleotide complex to produce a synergistic effect. In certain embodiments, the additional agent is administered to treat an undesired side effect of an HES-oligonucleotide complex of the invention. In some embodiments, the HES-oligonucleotide complex is administered at the same time as the additional agent. In some embodiments, the HES-oligonucleotide and additional agent are prepared together in a single pharmaceutical formulation. In other embodiments, the HES-oligonucleotide and additional agent are prepared separately. In further embodiments, the additional agent is administered at a different time from the HES-oligonucleotide complex.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. In addition, the term 'cell' can be construed as a cell population, which can be either heterogeneous or homogeneous in nature, and can also refer to an aggregate of cells. Moreover, each of the limitations of the invention can encompass various embodiments of the invention. It is, therefore, envisioned that each of the limitations of the invention involving any one element or combinations of elements can be included in each embodiment of the invention.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention.

The disclosure of U.S. Appl. No. 61/630,446 is herein incorporated by reference in its entirety. Moreover, all publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The following examples which are offered to illustrate, but not to limit, the claimed invention, clearly show: (1) the presence of an HES allows delivery of oligonucleotides inside live cells without toxicity in a living organism (2) the formation of an HES in a double-stranded RNA (3) the absence of inhibition by an HES of processing of a double-stranded RNA (dsRNA) by the endonuclease Dicer and (4) the knockdown of a gene by a dsRNA containing an H-type excitonic structure.

Example 1

In Vivo Delivery of an Oligonucleotide Containing an H-Type Excitonic Structure

In order to show that oligonucleotides can be delivered inside live cells without toxicity in a live organism, a strand of DNA containing a sequence of 24 nucleic acids complementary to β-actin (CCC GGC GAT ATC ATC ATC CAT AAC (SEQ ID NO:1) (Sokol et al. Proc. Natl. Acad. Sci. USA 95:11538-43 (1998)) was synthesized and covalently labeled on opposite ends of the strand with the fluorophore (N-Ethyl-N'-[5-(N"-succinimidyloxycarbonyl)pentyl]-3,3, 3',3',-tetramethyl-2,2'-indodicarbocyanine chloride). The labeled oligonucleotide was purified by reverse phase high pressure liquid chromatography (hplc) and then lyophilized. The presence of an intramolecular HES in the oligonucleotide was confirmed by absorbance spectrometry and fluorometry. All measurements were carried out in phosphate buffered saline (PBS) in which the labeled oligonucleotide was readily solubilized.

A volume of two hundred microliters of the labeled oligonucleotide at a concentration of 5 micromolar in PBS was injected into the tail vein of a six week old C57BL/6 mouse (464 micrograms/kilogram). After 18 hours, the mouse was sacrificed by cervical dislocation; blood was immediately withdrawn from the heart and the spleen was removed. The blood was diluted with PBS, placed over Hypaque-Ficoll, and centrifuged at 1300 rpm for 30 minutes. Cells at the interface between the Hypaque-Ficoll and PBS were collected, washed with PBS, placed on a #0 borosilicate glass surface in a Mattek glass bottom microwell dish (P35G-0-10-C), allowed to settle (ca. 10 minutes), and then imaged with a Leica DMIRE2 confocal microscope. In parallel a single cell suspension from the spleen was made by applying the end of a syringe to the resected organ and then triturating the suspension. The splenocytes in PBS were then exposed to an equal volume of ACK lysis buffer for 3 minutes, diluted further with PBS, and centrifuged. Cells in the pellet were then resuspended in PBS, placed in a Mattek glass bottom microwell dish (P35G-0-10-C), allowed to settle (ca. 10 minutes), and finally imaged with a confocal microscope.

Imaging of the blood and splenocyte samples was carried out by acquiring a series of stacks of 1 micron sections in both the fluorescence and brightfield (differential interference contrast (DIC)) channels. Images were reconstructed by overlaying the sections of each channel to produce a condensed stack then overlaying the condensed images from fluorescence and DIC channels.

Images showed the fluorescence channels overlayed on the DIC images indicated all splenocytes and blood cells took up the HES-containing oligonucleotide. The presence of oligonucleotide inside live cells was confirmed by examination of each 1 micron section. As was also evident, particularly from the DIC images, cells from both blood and spleen were healthy, a point further substantiated by the lack of uptake of trypan blue or propidium iodide by cells in these same samples.

Example 2

Quantitation of In Vivo Delivery of an Oligonucleotide Containing an H-Type Excitonic Structure In order to quantitate the in vivo delivery of oligonucleotides inside live cells without toxicity in a live organism, a Dicer substrate was prepared as described in Example 3. The sequence for the Dicer substrate, i.e., the sense strand and antisense strand for eGFP (Kim et al. Nature Biotech. 22:321-5 (2004)), was chosen so that no complementary pairing in the subject mice (standard, nontransfected BALB/C strain) could take place. The double-labeled lyophilized dsRNA was solubilized in phosphate buffered saline (PBS). The presence of an intramolecular HES in the oligonucleotide was confirmed by absorbance spectrometry and fluorometry.

Figure 1B:
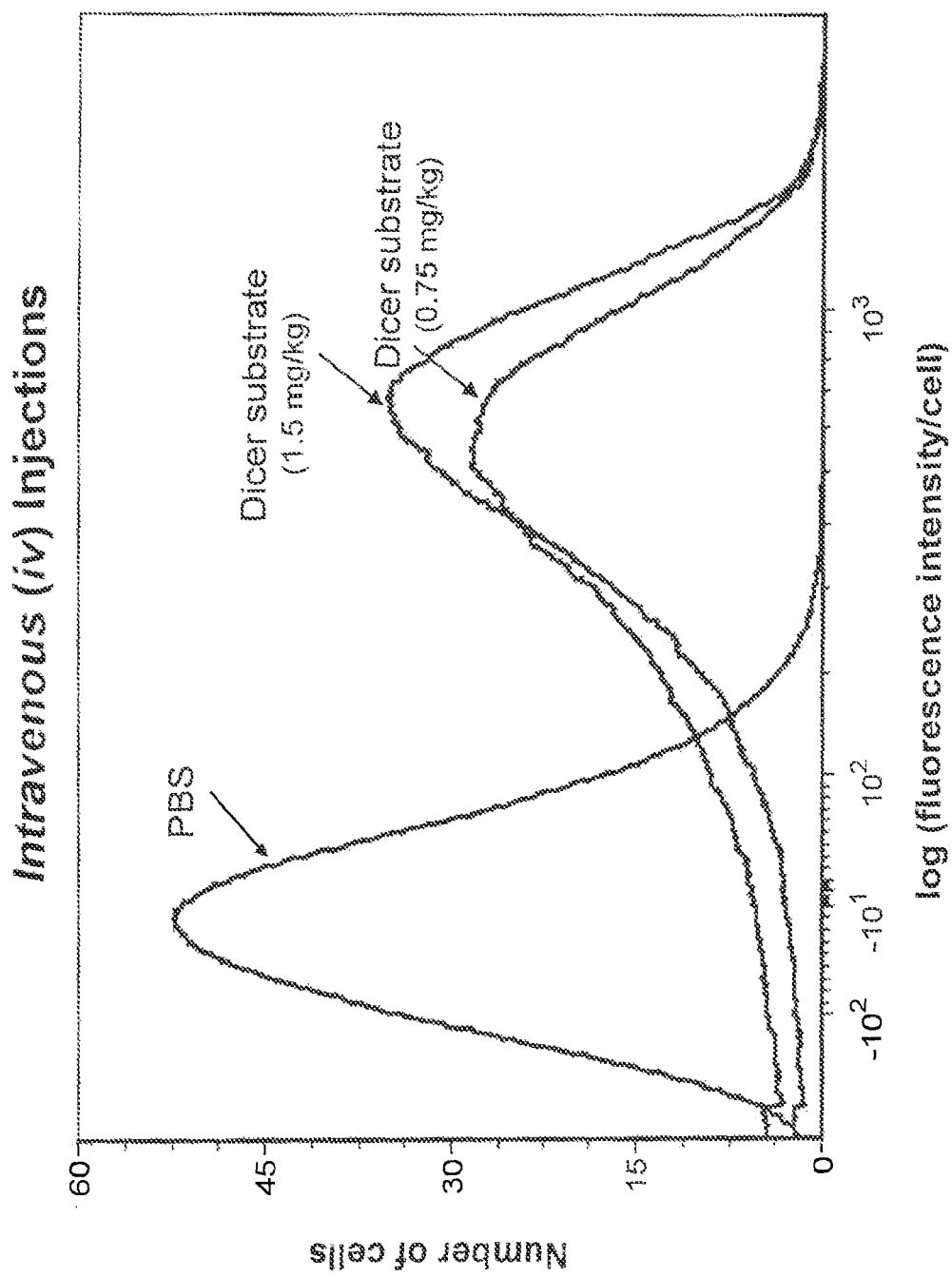

A volume of two hundred microliters of the labeled oligonucleotide at a concentration of 5 micromolar or 10 micromolar in PBS was injected into the tail vein or the peritoneum of each 10-12 week old BALB/C mouse (0.75 or 1.5 milligrams/kilogram). After 3 hours, blood was drawn in the presence of heparin from the heart of each mouse. The blood was diluted with PBS, placed over Hypaque-Ficoll and centrifuged at 1300 rpm for 30 minutes. Cells at the interface between the Hypaque-Ficoll and PBS were collected; the fluorescence of individual cells was measured with a Cytek-modified Becton-Dickinson Caliber flow cytometer, FIG. 1 shows histograms of blood cells isolated from mice three hours after an injection of 200 microliters of buffer (PBS) or a Dicer substrate. In Panel a, fluorescence from cells which were isolated after a single ip injection of PBS or the Dicer substrate (1.5 mg/kg) is shown in histogram format. The increase in fluorescence intensity of ca. 2 logs in the cells exposed to the Dicer substrate relative to those from the animal that had received an injection of PBS indicates significant uptake of the Dicer substrate. Moreover, the light scattering properties of both groups indicated highly viable cells. In Panel b, histograms show the fluorescence of cells isolated after an iv injection of PBS, the Dicer substrate at a concentration of 1.5 mg/kg, or the Dicer substrate at a concentration of 0.75 mg/kg. As with the ip route, cells from iv-injected animals that had received the Dicer substrate at either dose also showed ca. a two log increase in fluorescence intensity per cell relative to those from the PBS animal with the higher concentration resulting in a slightly higher average intensity per cell. And, again, no signs of toxicity were observed.

Example 3

Formation of an Intramolecular HES in Real-Time

The formation of an HES is associated with quenching of fluorescence;

specifically, the fluorescence of the dimer is reduced relative to that of the individual components. Therefore, in order to illustrate the process of HES formation, two complementary strands of RNA, i.e., the sense strand and antisense strand (Kim et al. Nature Biotech. 22:321-5 (2004)), were each labeled with N-Ethyl-N'-[5-(N"-succinimidyloxycarbonyl)pentyl]-3,3,3',3',-tetramethyl-2,2'-indodicarbocyanine chloride and then added together; the fluorescence intensity of the latter solution was then compared with those of the components, i.e., the single strands alone.

Figure 2:
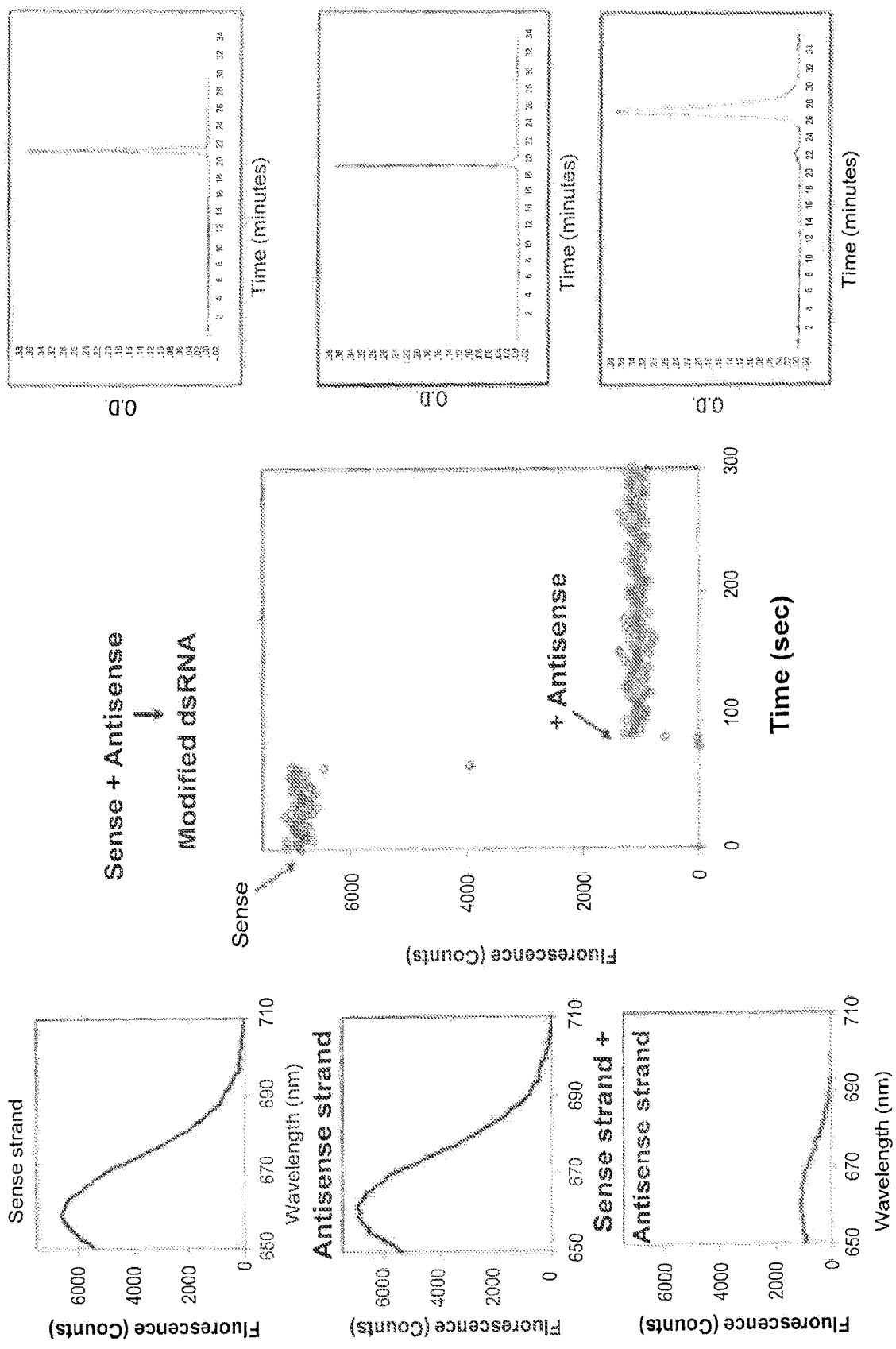

The fluorescence spectra of the two singly-labeled strands are shown in the top two panels on the left side of FIG. 2. The purity of each strand as measured by reverse phase hplc is also shown in the corresponding panels on the right side of FIG. 2.

With a data acquisition rate of 1 datum/sec. the center section shows, first, the fluorescence intensity of the sense solution as a function of time (from 0 to ca. 80 sec.) to be ca. 7000 Counts. When the shutter is closed at 80 sec. in order to add the antisense solution, the intensity drops to the zero. Upon re-opening the shutter, the intensity is recorded at ca. 1100 Counts and remains steady at this level due to the tight complex formed between the sense and antisense strands.

The lowest panels on the right and left sides show the emission spectrum and hplc chromatogram of the sense-antisense complex, respectively.

Example 4

Recognition of the a Double-Stranded Sense-Antisense RNA Complex by Dicer

Dicer is an endonuclease that cleaves double-stranded RNA (dsRNA) and preMiRNA (MiRNA) into short double-stranded RNA fragments called small interfering siRNA. Since one of the embodiments of this invention is the delivery of oligonucleotides for silencing RNA, it is essential that an HES-containing dsRNA be recognizable and cleavable by Dicer. Therefore, the dsRNA described in Example 3 which contains an HES on the end of the duplex was exposed to a recombinant Dicer (Recombinant Turbo Dicer Cat (# T520002) from Genlantis). Using the digestion conditions in the instructions from the reagent supplier the fluorescence of the dsRNA-containing solution was measured after addition of this endonuclease.

Two Dicer substrates derivatized with an HES were synthesized: one was comprised of two strands of unmodified ribonucleotides (25 and 27 bases) and a second with the same two strands but with the 25 nucleotide chain extended with two O-methylated nucleotides on the end. Terminal O-methylation has been shown to protect oligonucleotides from exonucleases present in plasma. As shown in FIG. 3, the fluorescence of the solutions of both dsRNAs increased as a function of time after addition of Dicer, thus confirming the absence of inhibition of the HES for processing by this endonuclease. Additionally, the dsRNA with the O-methylation showed a slightly slower rate of digestion, consistent with the protective effect of this modification.

Example 5

Knockdown of a Gene by a dsRNA Containing an H-Type Excitonic Structure

In order to show the functionality of an oligonucleotide linked to an H-type excitonic structure, the fluorescence per cell from blood cells of mice transgenic for expression of eGFP was measured after exposure to a double-stranded RNA (dsRNA) derivatized with an H-type excitonic structure, as described in FIG. 2, and containing the sense and antisense strands coding for eGFP (Kim et al, Nature Biotech. 22:321-5 (2004)). Measurements were made by flow cytometry from the blood of mice after separation of mononuclear cells.

FIG. 4 shows the superimposed histograms of both the control and Dicer-treated populations. The control cells show two populations: ca. 67% of cells with >$10^2$ fluorescence units per cell than a second nonfluorescent population. Treatment with the Dicer substrate results in a single population with an average fluorescence just slightly above that of the nonfluorescent control cells.

3. The method of claim 1, wherein the therapeutic oligonucleotide can induce RNA interference (RNAi).

4. The method of claim 1, wherein the therapeutic oligonucleotide is a member selected from: siRNA, shRNA, miRNA, a Dicer substrate, and an antisense.

5. The method of claim 1, wherein the therapeutic oligonucleotide is a Dicer substrate.

6. The method of claim 5, wherein the Dicer substrate comprises a nucleic acid strand 18-35 nucleotides in length.

7. The method of claim 5, wherein the Dicer substrate comprises a nucleic acid strand 18-25 nucleotides in length.

8. The method of claim 5, wherein the Dicer substrate comprises 2 complementary nucleic acid strands that are each 18-35 nucleotides in length and wherein the complementary nucleic acid strands form a 2 nucleotide 3' overhang.

9. The method of claim 5, wherein the Dicer substrate comprises 2 complementary nucleic acid strands that are each 18-25 nucleotides in length and wherein the complementary nucleic acid strands form a 2 nucleotide 3' overhang.

10. The method of claim 1, wherein the therapeutic oligonucleotide contains one or more modified nucleoside motifs selected from: locked nucleic add (LNA), alpha LNA, 2'-Fluoro (2'F), 2'-O(CH$_2$)$_2$OCH$_3$(2'-MOE), 2'-OCH$_3$ (2'-O-methyl) (2'OME), PNA, and morpholino.

11. The method of claim 1, wherein the therapeutic oligonucleotide contains one or more modifications selected from: phosphorothioate, phosphorodithioate, phosphoramide, 3'-methylene phosphonate, O-methylphosphoroamidiate, PNA, morpholino, C-5 propyne, and 5-methyl C.

What is claimed is:

1. A method for modulating a target nucleic acid or protein in a subject, said method comprising administering to the subject an effective amount of an H-type excitonic structure (HES)-oligonucleotide containing a therapeutic oligonucleotide that specifically hybridizes to a target nucleic acid sequence in vivo and thereby modulates the level of a protein encoded or regulated by the nucleic acid.

2. A method for treating a disease or disorder in a subject, said method comprising administering to a subject in need thereof, an effective amount of an H-type excitonic structure (HES)-oligonucleotide containing a therapeutic oligonucleotide that specifically hybridizes to a nucleic acid sequence in vivo and modulates the level of a protein encoded or regulated by the nucleic acid; wherein the disease or disorder is characterized by
   (a) overexpression or underexpression of the target a nucleic acid in the subject, or
   (b) overexpression or underexpression of a protein encoded by the target nucleic in the subject.

12. The method of claim 2, wherein the therapeutic oligonucleotide can induce RNA interference (RNAi).

13. The method of claim 2, wherein the therapeutic oligonucleotide is a member selected from: siRNA, shRNA, miRNA, a Dicer substrate, and an antisense.

14. The method of claim 2, wherein the therapeutic oligonucleotide is a Dicer substrate.

15. The method of claim 14, wherein the Dicer substrate comprises a nucleic acid strand 18-35 nucleotides in length.

16. The method of claim 14, wherein the Dicer substrate comprises a nucleic acid strand 18-25 nucleotides in length.

17. The method of claim 14, wherein the Dicer substrate comprises 2 complementary nucleic acid strands that are each 18-35 nucleotides in length and wherein the complementary nucleic acid strands form a 2 nucleotide 3' overhang.

18. The method of claim 14, wherein the Dicer substrate comprises 2 complementary nucleic add strands that are each 18-25 nucleotides in length and wherein the complimentary nucleic acid strands form a 2 nucleotide 3' overhang.

19. The method of claim 10, wherein the therapeutic oligonucleotide contains one or more modified nucleoside motifs selected from: locked nucleic add (LNA), alpha LNA, 2-Fluoro (2'F), 2'-O(CH$_2$)$_2$OCH$_3$(2'-MOE), 2'-OCH$_3$ (2'-O-methyl) (2'OME), PNA and morpholino.

20. The method of claim 2, wherein the therapeutic oligonucleotide contains one or more modifications selected from: phosphorothioate, phosphorodithioate, phosphoramide, 3'-methylene phosphonate, O-methylphosphor-oamidiate, PNA, morpholino, C-5 propyne, and 5-methyl C.

21. The method of claim 1, wherein the therapeutic oligonucleotide contains 1 or 2 substitutions, deletions or insertions compared to the corresponding reverse complementary strand of a target RNA.

\* \* \* \* \*

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: synthesized complement of Beta-actin

<400> SEQUENCE: 1
cccggcgata tcatcatcca taac                                          24